US009957328B2

(12) United States Patent
Ellis et al.

(10) Patent No.: US 9,957,328 B2
(45) Date of Patent: *May 1, 2018

(54) BACTERIAL HOST STRAIN EXPRESSING RECOMBINANT DSBC

(71) Applicant: UCB PHARMA, S.A., Brussels (BE)

(72) Inventors: Mark Ellis, Slough (GB); David Paul Humphreys, Slough (GB)

(73) Assignee: UCB PHARMA, S.A., Slough, Berkshire (GB)

(*) Notice: Subject to any disclaimer, the term of this patent is extended or adjusted under 35 U.S.C. 154(b) by 0 days. days.

This patent is subject to a terminal disclaimer.

(21) Appl. No.: 15/667,649

(22) Filed: Aug. 3, 2017

(65) Prior Publication Data

US 2017/0335003 A1 Nov. 23, 2017

Related U.S. Application Data

(63) Continuation of application No. 14/131,994, filed as application No. PCT/EP2012/002945 on Jul. 13, 2012, now Pat. No. 9,725,516.

(30) Foreign Application Priority Data

Jul. 13, 2011 (EP) .................................... 11173880

(51) Int. Cl.
*C12N 1/20* (2006.01)
*C07K 16/28* (2006.01)
*C12N 9/90* (2006.01)

(52) U.S. Cl.
CPC .......... *C07K 16/2875* (2013.01); *C12N 9/90* (2013.01); *C07K 2317/14* (2013.01); *C07K 2317/55* (2013.01)

(58) Field of Classification Search
None
See application file for complete search history.

(56) References Cited

U.S. PATENT DOCUMENTS

| | | | |
|---|---|---|---|
| 5,264,365 A | 11/1993 | Georgiou et al. | |
| 5,508,192 A | 4/1996 | Georgiou et al. | |
| 5,665,866 A | 9/1997 | Weir et al. | |
| 6,027,888 A | 2/2000 | Georgiou et al. | |
| 6,083,715 A | 7/2000 | Georgiou et al. | |
| 6,306,619 B1 | 10/2001 | Jones et al. | |
| 7,012,135 B2 | 3/2006 | Athwal et al. | |
| 7,041,479 B2 | 5/2006 | Swartz et al. | |
| 7,419,659 B2 | 9/2008 | Popplewell | |
| 7,662,587 B1 | 2/2010 | Cheng et al. | |
| 8,293,237 B2 | 10/2012 | Burkly et al. | |
| 8,470,552 B2 | 6/2013 | Crougan et al. | |
| 8,784,823 B2 | 7/2014 | Burkly et al. | |
| 8,969,037 B2 | 3/2015 | Ellis et al. | |
| 8,969,038 B2 | 3/2015 | Ellis et al. | |
| 8,969,039 B2 | 3/2015 | Ellis et al. | |
| 9,109,216 B2 | 8/2015 | Ellis et al. | |
| 9,315,770 B2 | 4/2016 | Ellis et al. | |
| 9,493,558 B2 | 11/2016 | Ellis et al. | |
| 9,493,559 B2 | 11/2016 | Ellis et al. | |
| 9,550,973 B2 | 1/2017 | Ellis et al. | |
| 2005/0048572 A1 | 3/2005 | Reilly et al. | |
| 2006/0204493 A1 | 9/2006 | Huang et al. | |
| 2009/0252743 A1 | 10/2009 | Heavner et al. | |
| 2010/0104573 A1 | 4/2010 | Burkly et al. | |
| 2011/0111408 A1 | 5/2011 | Marrichi et al. | |
| 2012/0258492 A1 | 10/2012 | Ellis et al. | |
| 2012/0288894 A1 | 11/2012 | Ellis et al. | |
| 2012/0295309 A1 | 11/2012 | Ellis et al. | |
| 2012/0301920 A1 | 11/2012 | Ellis et al. | |
| 2013/0045219 A1 | 2/2013 | Burkly et al. | |
| 2013/0060009 A1 | 3/2013 | Bilgischer et al. | |
| 2013/0178607 A1 | 7/2013 | Wild | |
| 2014/0141468 A1* | 5/2014 | Ellis ................... | C07K 16/2875 435/69.6 |
| 2014/0302016 A1 | 10/2014 | Burkly et al. | |
| 2015/0111249 A1 | 4/2015 | Bassett et al. | |
| 2015/0132828 A1 | 5/2015 | Ellis et al. | |
| 2015/0166651 A1 | 6/2015 | Ellis et al. | |
| 2015/0166652 A1 | 6/2015 | Ellis et al. | |
| 2015/0344840 A1 | 12/2015 | Ellis et al. | |

FOREIGN PATENT DOCUMENTS

| | | |
|---|---|---|
| CN | 1549821 A | 11/2004 |
| EA | 007905 | 2/2007 |
| EP | 2 546 267 | 1/2013 |
| JP | 2002-504826 | 2/2002 |
| WO | WO 98/56930 | 12/1998 |

(Continued)

OTHER PUBLICATIONS

Casset, F. et al. "A peptide mimetic of an anti-CD4 monoclonal antibody by rational design" *Biochemical and Biophysical Research Communications*, 2003, pp. 198-205, vol. 307.
Smith-Gill, S. J. et al. "Contributions of Immunoglobulin Heavy and Light Chains to Antibody Specificity for Lysozyme and Two Haptens" *Journal of Immunology*, Dec. 15, 1987, pp. 4135-4144, vol. 139.
Song, M.-K. et al. "Light Chain of Natural Antibody Plays a Dominant Role in Protein Antigen Binding" *Biochemical and Biophysical Research Communications*, 2000, pp. 390-394, vol. 268.
Chen, Y. et al. "Selection and Analysis of an Optimized Anti-VEGF Antibody: Crystal Structure of an Affinity-matured Fab in Complex with Antigen" *J. Mol. Biol.*, 1999, pp. 865-881, vol. 293.
Ward, E. et al. "Binding activities of a repertoire of single immunoglobulin variable domains secreted from *Escherichia coli*" *Nature*, Oct. 12, 1989, pp. 544-546, vol. 341.
Kobayashi, H. et al. "Tryptophan H33 plays an important role in pyrimidine (6-4) pyrimidone photoproduct binding by a high-affinity antibody" *Protein Engineering*, 1999, pp. 879-884, vol. 12, No. 10.
Kumar, S. et al. "Molecular Cloning and Expression of the Fabs of Human Autoantibodies in *Escherichia coli*" *Journal of Biological Chemistry*, Nov. 10, 2000, pp. 35129-35136, vol. 275, No, 45.
Maccallum, R. M. et al. "Antibody-antigen Interactions: Contact Analysis and Binding Site Topography" *J. Mol. Biol.*, 1998, pp. 732-745, vol. 262.

(Continued)

*Primary Examiner* — Michael Burkhart
(74) *Attorney, Agent, or Firm* — Saliwanchik, Lloyd & Eisenschenk

(57) ABSTRACT

The present invention provides a recombinant gram-negative bacterial cell comprising an expression vector comprising a recombinant polynucleotide encoding DsbC and one or more polynucleotides encoding an antibody or an antigen-binding fragment thereof specifically binding to CD154.

27 Claims, 11 Drawing Sheets

(56) References Cited

FOREIGN PATENT DOCUMENTS

| WO | WO 01/68860 | 9/2001 |
|---|---|---|
| WO | WO 02/18445 | 3/2002 |
| WO | WO 02/18446 | 3/2002 |
| WO | WO 02/48376 | 6/2002 |
| WO | WO 2002/061090 | 8/2002 |
| WO | WO 03/018771 | 3/2003 |
| WO | WO 03/031475 | 4/2003 |
| WO | WO 03/48306 | 6/2003 |
| WO | WO 2003/048208 | 6/2003 |
| WO | WO 2004/003019 | 1/2004 |
| WO | WO 2004/051268 | 6/2004 |
| WO | WO 2004/072116 | 8/2004 |
| WO | WO 2005/003175 | 1/2005 |
| WO | WO 2005/011376 | 2/2005 |
| WO | WO 2005/035572 | 4/2005 |
| WO | WO 2006/030220 | 3/2006 |
| WO | WO 2006/033702 | 3/2006 |
| WO | WO 2006/054063 | 5/2006 |
| WO | WO 2008/118356 | 10/2008 |
| WO | WO 2011/036454 | 3/2011 |
| WO | WO 2011/057120 | 5/2011 |
| WO | WO 2011/086136 | 7/2011 |
| WO | WO 2011/086138 | 7/2011 |
| WO | WO 2011/086139 | 7/2011 |
| WO | WO 2011/086141 | 7/2011 |
| WO | WO 2011/095506 | 8/2011 |
| WO | WO 2012/013930 | 2/2012 |
| WO | WO 2013/171156 | 11/2013 |

OTHER PUBLICATIONS

Vajdos, F. F. et al. "Comprehensive Functional Maps of the Antigen-binding Site of an Anti-ErbB2 Antibody Obtained with Shotgun Scanning Mutagenesis" *J. Mol. Biol.*, 2002, pp. 415-428, vol. 320.

Colman, P. M. "Effects of amino acid sequence changes on antibody-antigen interactions" *Research in Immunology*, 1994, pp. 33-36, vol. 145.

Holm, P. et al. "Functional mapping and single chain construction of the anti-cytokeratin 8 monoclonal antibody TS1" *Molecular Immunology*, 2007, pp. 1075-1084, vol. 44.

Jang, Y.-J. et al. "The structural basis for DNA binding by an anti-DNA autoantibody" *Molecular immunology*, 1998, pp. 1207-1217, vol. 35.

Wu, H. et al. "Humanization of a Murine Monoclonal Antibody by Simultaneous Optimization of Framework and CDR Residues" *J. Mol. Biol.*, 1999, pp. 151-162, vol. 294.

De Pascalis, R. et al. "Grafting of "Abbreviated" Complementarity-Determining Regions Containing Specificity-Determining Residues Essential for Ligand Contact to Engineer a Less Immunogenic Humanized Monoclonal Antibody" *Journal of Immunology*, 2002, pp. 3076-3084, vol. 169.

Burks, E. A. et al. "In vitro scanning saturation mutagenesis of an antibody binding pocket" *Proc. Natl. Acad. Sci. USA*, Jan. 1997, pp. 412-417, vol. 94.

Brummell, D. A. et al. "Probing the combining site of an anti-carbohydrate antibody by saturation-mutagenesis: role of the heavy-chain CDR3 residues" *Biochemistry*, Feb. 2, 1993, pp. 1180-1187, vol. 32, No. 4.

Brorson, K. et al. "Mutational Analysis of Avidity and Fine Specificity of Anti-Levan Antibodies" *Journal of Immunology*, 1999, pp. 6694-6701, vol. 163.

Rudikoff, S. et al. "Single amino acid substitution altering antigen-binding specificity" *Proc. Natl. Acad. Sci. USA*, Mar. 1982, pp. 1979-1983, vol. 79.

Brams, P. et al. "A humanized anti-human CD154 monoclonal antibody blocks CD154-CD40 mediated human B cell activation" *International immunopharmacology*, 2001, pp. 277-294, vol. 1.

Boumpas, D.T. et al. "A Short Course of BG9588 (Anti-CD40 Ligand Antibody) Improves Serologic Activity and Decreases Hematuria in Patients With Proliferative Lupus Glomerulonephritis" *Arthritis & Rheumatism*, Mar. 2003, vol. 48, No. 3, pp. 719-727.

Durie, F.H. et al. "Prevention of Collagen-Induced Arthritis with an Antibody to gp39, the Ligand for CD40" *Science*, Sep. 3, 1993, vol. 261, pp. 1328-1330.

Ferrant, J.L. et al. "The contribution of Fc effector mechanisms in the efficacy of anti-CD154 immunotherapy depends on the nature of the immune challenge" *International Immunology*, Oct. 5, 2004, vol. 16, No. 11, pp. 1583-1594.

Kuwana, M. et al. "Effect of a single injection of humanized anti-CD154 monoclonal antibody on the platelet-specific autoimmune response in patients with immune thrombocytopenic purpura" *Blood*, Feb. 15, 2004, vol. 103, No. 4, pp. 1229-1236.

Quezada, S.A. et al. "Distinct Mechanisms of Action of Anti-CD154 in Early Versus Late Treatment of Murine Lupus Nephritis" *Arthritis & Rheumatism*, Sep. 2003, vol. 48, No. 9, pp. 2541-2554.

Kalled, S. L. et al. "Apoptosis and Altered Dendritic Cell Homeostasis in Lupus Nephritis Are Limited by Anti-CD154 Treatment" *The Journal of Immunology*, 2001, pp. 1740-1747, vol. 167.

Cordeiro, A. C. et al. "Novel Therapies in Lupus—Focus on Nephritis" *Acta Reumatol Port.* 2008, pp. 157-169, vol. 33, No. 2.

Toubi, E. et al. "The Role of CD40-CD 154 Interactions in Autoimmunity and the Benefit of Distrupting this Pathway" *Immunity*, 2004, pp. 457-464, vol. 37, Nos. 6-7. Abstract Only.

Peters, A. et al. "CD40 and Autoimmunity: The Dark Side of a Great Activator" *Semin Immunol.*, Oct. 2009, pp. 293-300, vol. 21, No. 5.

Baneyx, F. et al. "Construction and Characterization of *Escherichia coli* Strains Deficient in Multiple Secreted Proteases: Protease III Degrades High-Molecular-Weight Substrates In Vivo" *Journal of Bacteriology*, Apr. 1991, pp. 2696-2703, vol. 173, No. 8.

Spiess, C. et al. "A Temperature-Dependent Switch from Chaperone to Protease in a Widely Conserved Heat Shock Protein" *Cell*, Apr. 30, 1999, p. 339-347, vol. 97.

Skorko-Glonek, J. et al. "The proteolytic activity of the HtrA (DegP) protein from *Escherichia coli* at low temperatures" *Microbiology*, 2008, pp. 3649-3658, vol. 154.

Meerman, H. J. et al. "Construction and Characterization of a Set of *E. coli* Strains Deficient in All Known Loci Affecting the Proteolytic Stability of Secreted Recombinant Proteins" *Bio/Technology*, Nov. 1994, pp. 1107-1110, vol. 12.

Written Opinion in International Application No. PCT/GB2010/001790, dated Feb. 3, 2011, pp. 1-9.

Silber, K. R. et al. "Deletion of the prc (tsp) gene provides evidence for additional tail-specific proteolytic activity in *Escherichia coli* K-12" *Mol. Gen Genet*, 1994, vol. 242, pp. 237-240.

Chen, C. et al. "High-Level Accumulation of a Recombinant Antibody Fragment in the Periplasm of *Escherichia coli* Requires a Triple-Mutant (degP prc spr) Host Strain" *Biotechnology and Bioengineering*, Mar. 5, 2004, pp. 463-474, vol. 85, No. 5.

Database UniProt [Online] EBI Accession No. UNIPROT:B7UFJ2, Subname: Full=Predicted peptidase, outer membrane lipoprotein, Feb. 10, 2009, XP-002630316, p. 1.

Baba, T. et al. "Construction of *Escherichia coli* K-12 in-frame, single-gene knockout mutants: the Keio collection" *Molecular Systems Biology*, 2006, pp. 1-11.

Database UniProt [Online] EBI Accession No. UNIPROT:B7LAJ9, Subname: Full=Putative peptidase, outer membrane lipoprotein, Feb. 10, 2009, XP-002630317, p. 1.

Database UniProt [Online] EBI Accession No. UNIPROT:B7LJR7, Subname: Full=Putative peptidase, outer membrane lipoprotein, Feb. 10, 2009, XP-002630318, p. 1.

Database UniProt [Online] EBI Accession No. UNIPROT:C1M6L5, Subname: Full=Putative uncharacterized protein, May 26, 2009, XP-002630319, p. 1.

Hara, H. et al. "Overproduction of Penicillin-Binding Protein 7 Suppresses Thermosensitive Growth Defect at Low Osmolarity due to an spr Mutation of *Escherichia coil*" *Microbial Drug Resistance*, Jan. 1, 1996, pp. 63-72, vol. 2, No. 1.

Aramini, J. et al. "Solution NMR Structure of the NIpC/P60 Domain of Lipoprotein Spr from *Escherichia coil*: Structural Evidence for a Novel Cysteine Peptidase Catalytic Triad" *Biochemistry*, Sep. 1, 2008, pp. 9715-9717, vol. 47.

Tadokoro, A. et al. "Interaction of the *Escherichia coli* Lipoprotein NIpI with Periplasmic Prc (Tsp) Protease" *Journal of Biochemistry*, 2004, pp. 185-191, vol. 135.

(56) References Cited

OTHER PUBLICATIONS

Written Opinion in International Application No. PCT/EP2011/050415, dated Jun. 20, 2011, pp. 1-15.
Hu, X. et al. "Optimisation of production of a domoic acid-binding scFv antibody fragment in *Escherichia coli* using molecular chaperones and functional immobilisation on a mesoporous silicate support" *Protein Expression and Purification,* Jan. 8, 2007, pp. 194-201, vol. 52.
O'Dwyer, R. et al. "Microarray-based analysis of recombinant protein production in *E. coil*" *Microbial Cell Factories,* 2006, pp. 1-2 vol. 5, Supp 1.
Maskos, K. et al. "DsbA and DsbC-catalyzed Oxidative Folding of Proteins with Complex Disulfide Bridge Patterns In Vitro and In Vivo" *Journal of Molecular Biology,* Jan. 17, 2003, pp. 495-513, vol. 325.
Written Opinion in International Application No. PCT/EP2011/050416, dated Apr. 26, 2011, pp. 1-7.
Written Opinion in International Application No. PCT/EP2011/050413, dated Apr. 8, 2011, pp. 1-7.
Pan, K.-L. et al. "Roles of DegP in Prevention of Protein Misfolding in the Periplasm upon Overexpression of Penicillin Acylase in *Escherichia coil*" *Journal of Bacteriology,* May 2003, pp. 3020-3030, vol. 185, No. 10.
Pending claims from U.S. Appl. No. 14/827,408, 2015, pp. 1-4.
Written Opinion in International Application No. PCT/EP2012/002945, dated Oct. 24, 2012, pp. 1-9.
Arbabi-Ghahroudi, M., et al., "Prokaryotic expression of antibodies," *Cancer and Metastasis Reviews,* Dec. 1, 2005, vol. 24, No. 4, pp. 501-519.
Gehring, C.K. et al. "Functional and nutritional characteristics of proteins and lipids recovered by isoelectric processing of fish by-products and low-value fish: A review" *Food Chemistry,* 2011, pp. 422-431, vol. 124.

Georgiou, G., et al., "Preparative expression of secreted proteins in bacteria: status report and future prospects," *Current Opinion in Biotechnology,* Oct. 1, 2005, vol. 16, No. 5, pp. 538-545.
Getman, K. et al. "Pharmacokinetic Effects of 4C9, an Anti-FcRn Antibody, in Rats: Implications for the use of FcRn Inhibitors for the Treatment of Humoral Autoimmune and Alloimmune Conditions" *J. Pharm.* 2005, pp. 718-729, vol. 94., No. 4.
Hu, X. et al. "Cloning, expression and characterisation of a single-chain Fv antibody fragment against domoic acid in *Escherichia coli*" *Journal of Biotechnology,* 2005, pp. 38-45, vol. 120.
Liu, Z. et al., "The Influence of Coexpression of TrxA and DsbC to the Expression of Heterogenous Protein with Multiple Disulfide Bonds" *Chinese Journal of Biochemistry and Molecular Biology,* Aug. 30, 2002, pp. 486-489, vol. 18, No. 4.
Ponniah, K., et al., "The production of soluble and correctly folded recombinant bovine β-lactoglobulin variants A and B in *Escherichia coli* for NMR studies," *Protein Expression and Purification,* 2010, vol. 70, No. 2, pp. 283-289.
Skorko-Glonek, J. et al. "Site-directed mutagenesis of the HtrA(DegP) serine protease, whose proteolytic activity is indispensable for *Escherichia coli* survival at elevated temperatures" *Gene,* 1995, vol. 163, pp. 47-52.
Want, A. et al. "Studies Related to Antibody Fragment (Fab) Production in *Escherichia coli* W3110 Fed-Batch Fermentation Processes Using Multiparameter Flow Cytometry" *Cytometry Part A,* Feb. 2009, pp. 148-154, vol. 75, No. 2.
Written Opinion in International Application No. PCT/EP2013/059803, dated Aug. 14, 2013, pp. 1-5.
Wunderlich, M. et al. "Bacterial Protein Disulfide Isomerase: Efficient Catalysis of Oxidative Protein Folding at Acidic pH" *Biochemistry,* 1993, pp. 12251-12256, vol. 32.
Kolaj, O. et al. "Use of folding modulators to improve heterologous protein production in *Escherichia coli*" *Microbial Cell Factories,* 2009, pp. 1-18, vol. 8, No. 9.

* cited by examiner

Figure 9

Wild type ptr (protease III) 5'.

```
     *   M   P   R   S   T   W   F   K   A   L   L   L   L   V
    TGA ATG CCC CGC AGC ACC TGG TTC AAA GCA TTA TTG TTG TTA GTT

A   L   W   A   P   L   S
    GCC CTT TGG GCA CCC TTA AGT
```

Mutated Δ ptr (protease III) 5'.

```
                                                    EcoRI
                                                  ~~~~~~~~
     *   I   P   R   S   T   W   F   K   A   L   L   L   L   V
    TGA ATT CCC CGC AGC ACC TGG TTC AAA GCA TTA TTG TTG TTA GTT

AseI
                          ~~~~~~~~
     A   L   W   A   H   *   C
    GCC CTT TGG GCA CAT TAA TGT
```

Figure 10

Wild type Tsp 5'.

```
      M   N   M   F   F   R   L   T   A   L   A   G   L   L   A
     ATG AAC ATG TTT TTT AGG CTT ACC GCG TTA GCT GGC CTG CTT GCA

I   A   G   Q   T   F   A
     ATA GCA GGC CAG ACC TTC GCT
```

Mutated Δ Tsp 5'.

```
           EcoR I
      M   N   S   F   L   G   L   P   R   *   L   A   C   L   Q
     ATG AAT TCG TTT TTA GGC TTA CCG CGT TAG CTG GCC TGC TTG CAA

Ase I
      *   Q   A   R   H   *   L
     TAG CAG GCC AGA CAT TAA TTG
```

Figure 11

Wild type DegP

```
202    D   A   A   I   N   R   G   N   S   G   G
949    GAT GCA GCG ATC AAC CGT GGT AAC TCC GGT GGT
```

Mutated DegP S210A

```
                            Ase I
                         ―――――――――
202    D   A   A   I   N   R   G   N   A   G   G
949    GAT GCA GCG ATT AAT CGT GGT AAC GCC GGT GGT
```

BACTERIAL HOST STRAIN EXPRESSING RECOMBINANT DSBC

CROSS-REFERENCE TO RELATED APPLICATIONS

This application is a continuation of U.S. application Ser. No. 14/131,994, filed Jan. 10, 2014, now U.S. Pat. No. 9,725,516, which is the U.S. national stage application of International Patent Application No. PCT/EP2012/002945, filed Jul. 13, 2012.

The Sequence Listing for this application is labeled "Seq-List-replace.txt" which was created on Dec. 13, 2017 and is 159 KB. The entire content of the sequence listing is incorporated herein by reference in its entirety.

The invention relates to a recombinant bacterial host strain, particularly *E. coli*. The invention also relates to a method for producing a protein of interest in such a cell.

BACKGROUND OF THE INVENTION

Bacterial cells, such as *E. coli*, are commonly used for producing recombinant proteins that do not require glycosylation. There are many advantages to using bacterial cells, such as *E. coli*, for producing recombinant proteins, particularly due to the versatile nature of bacterial cells as host cells, allowing gene insertion via plasmids. *E. coli* has been used to produce many recombinant proteins including human insulin.

Despite the many advantages to using bacterial cells to produce recombinant proteins, there are still significant limitations, including poor cell health phenotype.

Accordingly, there is still a need to provide new bacterial strains which provide advantageous means for producing recombinant proteins.

The generation of humoral and cell-mediated immunity is orchestrated by the interaction of activated helper T cells with antigen-presenting cells ("APCs") and effector T cells. Activation of the helper T cells is not only dependent on the interaction of the antigen-specific T-cell receptor ("TCR") with its cognate peptide-MHC ligand, but also requires coordinate binding and activation by a number of cell adhesion and costimulatory molecules.

The natural receptor binding to CD40 is CD40 ligand (CD40-L=CD154), a critical costimulatory molecule that is expressed on the surface of CD4+ T cells in an activation-dependent, temporally-restricted manner. CD154 is also expressed, following activation, on a subset of CD8+ T cells, basophils, mast cells, eosinophils, natural killer cells, B cells, macrophages, dendritic cells and platelets. CD40 is constitutively and widely expressed on the surface of many cell types, including B cells and other antigen-presenting cells.

Signaling through CD40 after engagement with CD154 initiates a cascade of cellular events that results in the activation of the CD40 receptor-bearing cells and optimal CD4+ T cell priming. More specifically, the binding of CD154 to CD40 promotes the differentiation of B cells into antibody-secreting cells and memory B cells.

The pivotal role of CD154 in regulating the function of both the humoral and cell-mediated immune response has provoked great interest in the use of inhibitors of this pathway for therapeutic immunomodulation. As such, anti-CD154 antibodies have been shown to be beneficial in a wide variety of models of immune response to other therapeutic proteins or gene therapy, allergens, autoimmunity and transplantation (see, e.g., U.S. Pat. No. 5,474,771 and WO 2008/118356, which are incorporated herein by reference in their entirety).

There is a need in the art to efficiently and cost-effectively produce high amounts of antibodies or antibody fragments interfering with the interaction of CD40 and CD154 suitable for therapeutic applications.

SUMMARY OF THE INVENTION

The present invention provides a recombinant gram-negative bacterial cell comprising:
  a) a recombinant polynucleotide encoding DsbC; and
  b) one or more polynucleotides encoding an antibody or an antigen-binding fragment thereof specifically binding to CD154.

More specifically the present invention provides a recombinant gram-negative bacterial cell, characterized in that the cell:
  a) comprises a recombinant polynucleotide encoding DsbC;
  b) has reduced Tsp protein activity compared to a wild-type cell, and
  c) has one or more polynucleotides encoding an antibody or an antigen-binding fragment thereof specifically binding to CD154.

In one embodiment the cell comprises a wild-type spr gene or a mutated spr gene, for example capable of suppressing the reduced activity Tsp phenotype.

The gram-negative bacterial cell according to the present invention shows advantageous growth and protein production phenotypes.

More specifically the present invention provides a recombinant gram-negative bacterial cell comprising a recombinant polynucleotide encoding a DsbC polypeptide comprising a histidine (His)-tag, preferably wherein the DsbC polypeptide comprises the sequence his-his-his-his-his-his (6× histidine).

More specifically the present invention provides a recombinant gram-negative bacterial cell comprising a recombinant polynucleotide comprising a polynucleotide with the sequence according to SEQ ID NO: 45 or SEQ ID NO: 51.

The present invention also provides an expression vector comprising a recombinant polynucleotide encoding DsbC and an antibody or an antigen-binding fragment thereof specifically binding to CD154.

More specifically the present invention provides an expression vector comprising a recombinant polynucleotide encoding a DsbC polypeptide comprising a histidine (His)-tag, preferably wherein the DsbC polypeptide comprises the sequence his-his-his-his-his-his (6× histidine).

More specifically the present invention provides an expression vector comprising a recombinant polynucleotide comprising a polynucleotide with the sequence according to SEQ ID NO: 45 or SEQ ID NO: 51.

The present invention also provides a method for producing an antibody or an antigen-binding fragment thereof specifically binding to CD154 comprising:
  a) culturing a recombinant gram-negative bacterial cell as defined above in a culture medium under conditions effective to express the antibody or the antigen-binding fragment thereof specifically binding to CD154 and the recombinant polynucleotide encoding DsbC; and
  b) recovering the antibody or an antigen-binding fragment thereof specifically binding to CD154 from the periplasm of the recombinant gram-negative bacterial cell and/or the culture medium.

BRIEF DESCRIPTION OF THE DRAWINGS

FIG. 9 shows polynucleotide and amino acid sequences of a region within the ptr gene that was mutated (SEQ ID NO: 53, wild type ptr (protease III); SEQ ID NO: 54, mutated Δptr (protease III).

FIG. 10 shows polynucleotide and amino acid sequences of a region within the Tsp gene that was mutated (SEQ ID NO: 55, wild type Tsp; SEQ ID NO: 56, mutated ΔTsp).

FIG. 11 shows polynucleotide and amino acid sequences of a region within the DegP gene that was mutated (SEQ ID NO: 57, wild type DegP; SEQ ID NO: 58, mutated DegP S210A).

BRIEF DESCRIPTION OF THE SEQUENCES

Figure 1:
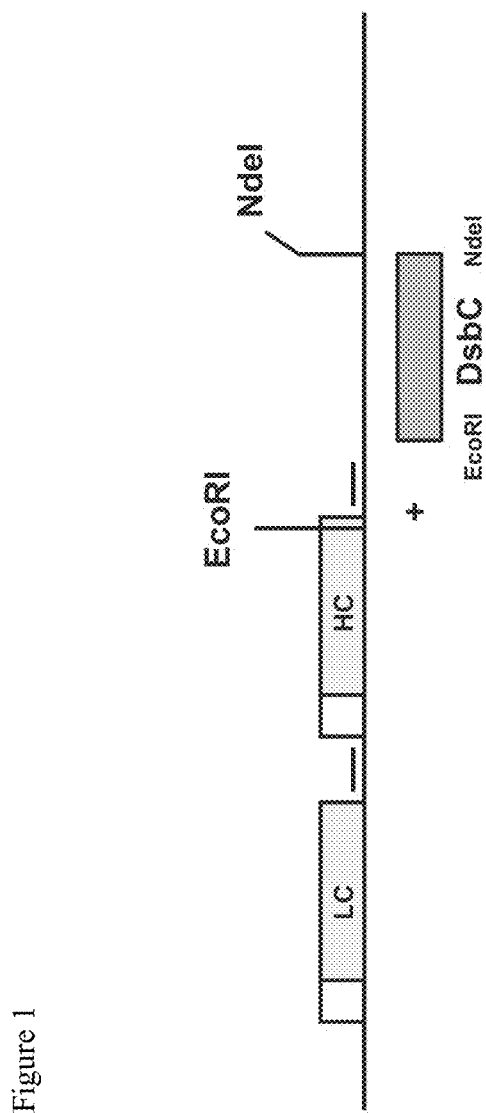
FIG. 1 shows the construction of a vector for use in producing a cell according to an embodiment of the present invention.

SEQ ID NO: 1 shows the amino acid sequence of CDRH1 of an anti-CD154 antibody.
SEQ ID NO: 2 shows the amino acid sequence of CDRH2 of an anti-CD154 antibody.
SEQ ID NO: 3 shows the amino acid sequence of CDRH3 of an anti-CD154 antibody.
SEQ ID NO: 4 shows the amino acid sequence of CDRL1 of an anti-CD154 antibody.
SEQ ID NO: 5 shows the amino acid sequence of CDRL2 of an anti-CD154 antibody.
SEQ ID NO: 6 shows the amino acid sequence of CDRL3 of an anti-CD154 antibody.
SEQ ID NO: 7 shows the polynucleotide and amino acid sequence of the variable light chain (gL4) of an anti-CD154 antibody (342).
SEQ ID NO: 8 shows the amino acid sequence of the variable light chain (gL4) of an anti-CD154 antibody (342).
SEQ ID NO: 9 shows the polynucleotide and amino acid sequence of the variable heavy chain (gH1) of an anti-CD154 antibody (342).
SEQ ID NO: 10 shows the amino acid sequence of the variable heavy chain (gH1) of an anti-CD154 antibody (342).
SEQ ID NO: 11 shows the polynucleotide and amino acid sequence comprising the variable and constant region of the light chain (gL4) of an anti-CD154 antibody fragment.
SEQ ID NO: 12 shows the amino acid sequence comprising the variable and constant region of the light chain (gL4) of an anti-CD154 antibody fragment.
SEQ ID NO: 13 shows the polynucleotide and amino acid sequence of a heavy chain fragment of an anti-CD154 antibody comprising the variable and the CH1 region with deletions in the hinge region.
SEQ ID NO: 14 shows the amino acid sequence of a heavy chain fragment of an anti-CD154 antibody comprising the variable and the CH1 region with deletions in the hinge region.
SEQ ID NO: 15 shows the polynucleotide and amino acid sequence of a heavy chain fragment of an anti-CD154 antibody comprising the variable, the CH1 and the hinge region.
SEQ ID NO: 16 shows the amino acid sequence of a heavy chain fragment of an anti-CD154 antibody comprising the variable, the CH1 and the hinge region.
SEQ ID NO: 17 shows the polynucleotide and amino acid sequence of a kappa light chain of an anti-CD154 antibody (342) including the signal peptide (amino acids 1-22).
SEQ ID NO: 18 shows the amino acid sequence of a kappa light chain of an anti-CD154 antibody (342) including the signal peptide (amino acids 1-22).
SEQ ID NO: 19 shows the polynucleotide and amino acid sequence of the entire heavy chain of an aglycosylated IgG$_4$ anti-CD154 antibody.
SEQ ID NO: 20 shows the amino acid sequence of the entire heavy chain of an aglycosylated IgG$_4$ anti-CD154 antibody.
SEQ ID NO: 21 shows the polynucleotide sequence coding for gL4 and gH1 (no hinge). SEQ ID NO: 22 shows the polynucleotide sequence coding for gL4 and gH1.
SEQ ID NO: 23 shows the polynucleotide and amino acid sequence for wild-type *E. coli* spr (GenBank accession no. D86610).
SEQ ID NO: 24 shows the amino acid sequence for wild-type *E. coli* spr (GenBank accession no. D86610).

SEQ ID NO: 25 shows the polynucleotide and amino acid sequence for wild-type *E. coli* Tsp with the signal sequence (GenBank accession no. M75634).

SEQ ID NO: 26 shows the amino acid sequence for wild-type *E. coli* Tsp with the signal peptide (GenBank accession no. M75634).

SEQ ID NO: 27 shows the amino acid sequence for wild-type *E. coli* DsbC (NCBI Reference Sequence AP_003452).

SEQ ID NO: 28 shows the polynucleotide sequence for knockout mutated Tsp gene.

SEQ ID NO: 29 shows the polynucleotide and amino acid sequence for wild-type *E. coli* DegP.

SEQ ID NO: 30 shows the amino acid sequence for wild-type *E. coli* DegP.

SEQ ID NO: 31 shows the polynucleotide and amino acid sequence for DegP comprising the point mutation S210A and an Ase I restriction marker.

SEQ ID NO: 32 shows the amino acid sequence for DegP comprising the point mutation S210A and an Ase I restriction marker.

SEQ ID NO: 33 to 36 show dicistronic intergenic sequences (IGS) IGS1, IGS2, IGS3 and IGS4, respectively.

SEQ ID NO: 37 shows the polynucleotide and amino acid sequence for wild-type *E. coli* OmpT.

SEQ ID NO: 38 shows the amino acid sequence for wild-type *E. coli* OmpT.

SEQ ID NO: 39 shows the polynucleotide and amino acid sequence for knockout mutated *E. coli* OmpT.

SEQ ID NO: 40 shows the amino acid sequence for knockout mutated *E. coli* OmpT.

SEQ ID NO: 41 shows the polynucleotide and amino acid sequence of the mutated *E. coli* OmpT comprising the point mutations D210A and H212A.

SEQ ID NO: 42 shows the amino acid sequence of the *E. coli* OmpT comprising the point mutations D210A and H212A.

SEQ ID NO: 43 shows the polynucleotide and amino acid sequence of wild-type *E. coli* DsbC.

SEQ ID NO: 44 shows the amino acid sequence of wild-type *E. coli* DsbC.

SEQ ID NO: 45 shows the polynucleotide and amino acid sequence of *E. coli* DsbC lacking an EcoRI restriction site with a His-tag.

SEQ ID NO: 46 shows the amino acid sequence of *E. coli* DsbC lacking an EcoRI restriction site with a His-tag.

SEQ ID NO: 47 shows the a polynucleotide sequence of primer 6283 Tsp 3'.

SEQ ID NO: 48 shows the a polynucleotide sequence of primer 6283 Tsp 5'.

SEQ ID NO: 49 shows the polynucleotide and amino acid sequence of wild-type *E. coli* ptr (protease III according to GenBank accession number X06227).

SEQ ID NO: 50 shows the amino acid sequence of wild-type *E. coli* ptr (protease III according to GenBank accession number X06227).

SEQ ID NO: 51 shows the polynucleotide and amino acid sequence of wild-type *E. coli* DsbC with a His-tag.

SEQ ID NO: 52 shows the amino acid sequence of wild-type *E. coli* DsbC with a His-tag.

DETAILED DESCRIPTION OF THE INVENTION

Tsp (also known as Prc) is a 60 kDa periplasmic protease. The first known substrate of Tsp was Penicillin-binding protein-3 (PBP3) (Determination of the cleavage site involved in C-terminal processing of penicillin-binding protein 3 of *Escherichia coli* (Hara et al. 4799-813; Nagasawa et al. 5890-93)) but it was later discovered that the Tsp was also able to cleave phage tail proteins and, therefore, it was renamed as Tail Specific Protease (Tsp). Silber, Keiler, and Sauer (295-99) and Silber and Sauer (237-40) describe a prc deletion strain (KS1000) wherein the mutation was created by replacing a segment of the prc gene with a fragment comprising a Kan$^r$ marker.

The reduction of Tsp (prc) activity is desirable to reduce the proteolysis of proteins of interest. Fab proteolysis may manifest itself as the presence of impurities such as a fragment which can be referred to as the light chain impurity.

However, it was found that cells lacking protease prc show thermosensitive growth at low osmolarity. Hara et al. isolated thermoresistant revertants containing extragenic suppressor (spr) mutations (Hara et al. 63-72). Spr is an 18 kDa membrane-bound periplasmic protease and the substrates of spr are Tsp and peptidoglycans in the outer membrane involved in cell wall hydrolysis during cell division. The spr gene is designated as UniProtKB/Swiss-Prot P0AFV4 (SPR_ECOLI).

Protein disulfide isomerase is an enzyme that catalyzes the formation and breakage of disulfide bonds between cysteine residues within proteins as they fold. It is known to co-express proteins which catalyze the formation of disulfide bonds to improve protein expression in a host cell. WO 98/56930 discloses a method for producing heterologous disulfide bond-containing polypeptides in bacterial cells wherein a prokaryotic disulfide isomerase, such as DsbC or DsbG, is co-expressed with a eukaryotic polypeptide. U.S. Pat. No. 6,673,569 discloses an artificial operon comprising polynucleotides encoding each of DsbA, DsbB, DsbC and DsbD for use in producing a foreign protein. EP0786009 discloses a process for producing a heterologous polypeptide in bacteria wherein the expression of nucleic acid encoding DsbA or DsbC is induced prior to the induction of expression of nucleic acid encoding the heterologous polypeptide.

DsbC is a prokaryotic protein found in the periplasm of *E. coli* which catalyzes the formation of disulfide bonds in *E. coli*. DsbC has an amino acid sequence length of 236 (including the signal peptide) and a molecular weight of 25.6 KDa (UniProt No. P0AEG6). DsbC was first identified in 1994 (Missiakas, Georgopoulos, and Raina 2013-20; Shevchik, Condemine, and Robert-Baudouy 2007-12).

It has been surprisingly found that the over-expression of DsbC in a gram-negative bacterial cell reduces lysis during cultivation of cells lacking protease Tsp. Accordingly, the present inventors have provided a new strain having advantageous properties for producing a protein of interest.

The gram-negative bacterial cell having the above specific combination of genetic modifications shows advantageous growth and protein production phenotypes.

In one embodiment the cell's genome is preferably isogenic to a wild-type bacterial cell except for the modification required to reduce Tsp protein activity compared to a wild-type cell.

In a further embodiment the cell according to the present invention has reduced Tsp protein activity compared to a wild-type cell and comprises a recombinant polynucleotide encoding DsbC and an altered spr protein. In this embodiment the cell's genome is preferably isogenic to a wild-type bacterial cell except for the mutated spr gene and a modification leading to reduced or absent expression of the Tsp protein compared to a wild-type cell.

The terms "protein" and "polypeptide" are used interchangeably herein, unless the context indicates otherwise. "Peptide" is intended to refer to 20 or fewer amino acids.

The term "polynucleotide" includes a gene, DNA, cDNA, RNA, mRNA, and analogues thereof, including, but not limited to, locked nucleic acid (LNA), peptide nucleic acid (PNA), morpholino nucleic acid, glycol nucleic acid (GNA), threose nucleic acid (TNA), etc., unless the context indicates otherwise.

As used herein, the term "comprising" in context of the present specification should be interpreted as "including".

The non-mutated cell or control cell in the context of the present invention means a cell of the same type as the recombinant gram-negative cell of the invention wherein the cell has not been modified to carry the recombinant polynucleotide encoding DsbC and one or more polynucleotides encoding an antibody or an antigen-binding fragment thereof specifically binding to CD154. For example, a non-mutated cell may be a wild-type cell and may be derived from the same population of host cells as the cells of the invention before modification to introduce any recombinant polynucleotide(s).

The expressions "cell", "cell line", "cell culture" and "strain" are used interchangeably.

The term "isogenic" in the context of the present invention means that the cell comprises the same or substantially the same nucleic acid sequence(s) compared to a wild-type cell except for the elements incorporated therein that characterize the invention, for example the recombinant polynucleotide encoding DsbC and the one or more polynucleotides encoding an antibody or an antigen-binding fragment thereof specifically binding to CD154, and optionally a modification leading to reduced or absent expression of the Tsp protein, and optionally a mutated spr gene. In this embodiment the cell according to the present invention comprises no further non-naturally occurring or genetically engineered changes to its genome.

In one embodiment wherein the polynucleotide encoding DsbC and/or the one or more polynucleotides encoding the antibody or antigen-binding fragment thereof are inserted into the cell's genome, the cell according to the present invention may have substantially the same genomic sequence compared to the wild-type cell except for the polynucleotide encoding DsbC and/or the one or more polynucleotides encoding the antibody or antigen-binding fragment thereof, and optionally a modification resulting in a reduced or absent expression of the Tsp protein or the expression of a Tsp protein with reduced protease activity, and optionally a mutated spr gene coding for a protein with reduced activity as compared to the wild-type, taking into account any naturally occurring mutations which may occur. In one embodiment, wherein the polynucleotide encoding DsbC and/or the one or more polynucleotides encoding the antibody or antigen-binding fragment thereof are inserted into the cell's genome, the cell according to the present invention may have exactly the same genomic sequence compared to the wild-type cell except for the polynucleotide encoding DsbC and/or the one or more polynucleotides encoding the antibody or antigen-binding fragment thereof.

The polynucleotide encoding DsbC may be present on a suitable expression vector transformed into the cell and/or integrated into the host cell's genome. In the embodiment where the polynucleotide encoding DsbC is inserted into the host cell's genome, the cell of the present invention differs from a wild-type cell due to the inserted polynucleotide encoding the DsbC. In this embodiment, the host cell's genome may be isogenic compared to a wild-type cell genome except for the recombinant polynucleotide encoding DsbC.

Preferably the polynucleotide encoding DsbC is in an expression vector in the cell, thereby causing minimal disruption to the host cell's genome.

The one or more polynucleotides encoding the antibody or an antigen-binding fragment thereof specifically binding to CD154 may be contained within a suitable expression vector transformed into the cell and/or integrated into the host cell's genome. In the embodiment where the polynucleotide encoding the antibody or antigen-binding fragment thereof specifically binding to CD154 is inserted into the host's genome, the cell of the present invention differs from a wild-type cell due to the inserted polynucleotide(s) encoding the antibody or antigen-binding fragment thereof. In this embodiment, the host cell's genome may be isogenic compared to a wild-type cell genome except for the polynucleotide(s) encoding the antibody or antigen-binding fragment thereof. Preferably the polynucleotide encoding the protein of interest is in an expression vector in the cell, thereby causing minimal disruption to the host cell's genome.

In one embodiment the recombinant polynucleotide encoding DsbC and the polynucleotide encoding the antibody or antigen-binding fragment thereof specifically binding to CD154 are inserted into the host's genome. In this embodiment, the cell of the present invention differs from a wild-type cell due to the inserted recombinant polynucleotide encoding DsbC and the one or more polynucleotide encoding the antibody or antigen-binding fragment thereof, and optionally a modification resulting in a reduced or absent expression of the Tsp protein or the expression of a Tsp protein with reduced protease activity, and optionally a mutated spr gene coding for a protein with reduced activity as compared to the wild-type. In this embodiment, the host cell's genome may be isogenic compared to a wild-type cell genome except for the recombinant polynucleotide encoding DsbC and the one or more polynucleotides encoding the antibody or antigen-binding fragment thereof.

In a preferred embodiment the recombinant polynucleotide encoding DsbC and the polynucleotide encoding the antibody or antigen-binding fragment thereof specifically binding to CD154 are present in the same or different expression vectors in the cell, thereby causing minimal disruption to the host cell's genome. In this embodiment the cell's genome may be substantially the same or exactly the same compared to the genome of a wild-type cell.

In one embodiment there is provided a recombinant *E. coli* cell that has reduced Tsp activity and optionally an spr gene or a mutant thereof, wherein modifications to the Tsp activity and any mutation in the spr gene are effected through changes in the cell's genome.

The cell according to this embodiment may be transformed with a vector such as a plasmid encoding DsbC and the antibody or a binding fragment thereof specifically binding to CD154. In one embodiment the vector or plasmid is not integrated into the genome of the cell.

The term "wild-type" in the context of the present invention means a strain of a gram-negative bacterial cell as it may occur in nature or may be isolated from the environment, which does not carry any recombinant polynucleotide or genetically engineered mutations. An example of a wild-type strain of *E. coli* is the K-12 strain and its pedigree strain W3110. *E. coli* strain K-12 has been in cultivation for 90 years now (Bachmann 525-57). *E. coli* strain K-12 and its pedigree strains such as W3110 are well-known in the art.

Strain W3110 is available for example from the American Tissue Culture Collection (ATCC) under catalog no. 27325. W3110 has the genotype: F−, λ−, IN(rrnD-rrnE)1, rph-1.

The present inventors have provided a recombinant gram-negative bacterial cell suitable for expressing an antibody or an antigen-binding fragment thereof specifically binding to CD154 which comprises a recombinant polynucleotide encoding DsbC.

The cells according to the present invention comprise a recombinant polynucleotide encoding DsbC. As used herein, a "recombinant polypeptide" refers to a protein that is constructed or produced using recombinant DNA technology. The polynucleotide encoding DsbC may be identical to the endogenous polynucleotide encoding DsbC found in wild-type bacterial cells. Alternatively, the recombinant polynucleotide encoding DsbC is a mutated version of the wild-type DsbC polynucleotide, for example being altered such that the restriction site, such as an EcoRI site, is removed from the DsbC protein and/or the his-tag. An example of a modified DsbC polynucleotide for use in the present invention is shown in SEQ ID NO: 45, which encodes the his-tagged DsbC sequence shown in SEQ ID NO: 46.

DsbC is characterized by the presence of an active site comprising amino acids—CXXC— wherein XX represents the amino acids GY. Variants of DsbC include wherein each X represents an amino acid independently selected (with the proviso that XX does not represent GY). Examples of XX include NY, SF, TF, MF, GF, HH, VH, SH, RF, FA, GA, MA, GI or AV.

In one embodiment the host cell of the invention comprises a variant of DsbC, for example where the active site is altered, in particular as described above.

In one embodiment the variant of DsbC has at least the biological activity of the wild-type protein, for example as measured in an in vitro assay.

In one embodiment the variant of DsbC has a greater biological activity than the wild-type protein, for example as measured in an in vitro assay.

In one embodiment the variant of DsbC has an alteration in the active site—CXXC—wherein XX represents NY, SF, TF, MF, GF, HH, VH, or SH.

In one embodiment the DsbC is wild-type.

The present inventors have identified that the selection of the expression of recombinant polynucleotide encoding DsbC in a bacterial cell provides an improved host cell for expressing an antibody or an antigen-binding fragment thereof specifically binding to CD154. The cells provided by the present invention have improved cell health and growth phenotype compared to wild-type bacterial cells.

Improved cell health as employed herein is intended to refer to one or more improved properties in comparison to cells which do not carry the features according to the present invention, for example a lower propensity for cell lysis at the growth phase or after induction of expression of a heterologous protein in the cell or other beneficial property as known to the skilled artisan.

The cells according to the present invention exhibit improved protein, such as antibody or antibody fragment, production yield compared to wild-type bacterial cells. The improved protein yield may be the rate of protein production and/or the duration of protein production from the cell. The improved protein yield may be the periplasmic protein yield and/or the supernatant protein yield. The recombinant bacterial cells may be capable of a faster rate of production of the protein, such as an antibody or fragment thereof, and, therefore, the same quantity of a protein of interest may be produced in a shorter time compared to a non-mutated bacterial cell. The faster rate of production of a protein of interest may be especially significant over the initial period of growth of the cell, for example over the first 5, 10, 20 or 30 hours post induction of protein expression.

The cells according to the present invention preferably express a yield in the periplasm and/or media of approximately 1.0 g/L, 1.5 g/L, 1.8 g/L, 2.0 g/L, 2.4 g/L, 2.5 g/L, 3.0 g/L, 3.5 g/L or 4.0 g/L of the antibody.

Figure 5:
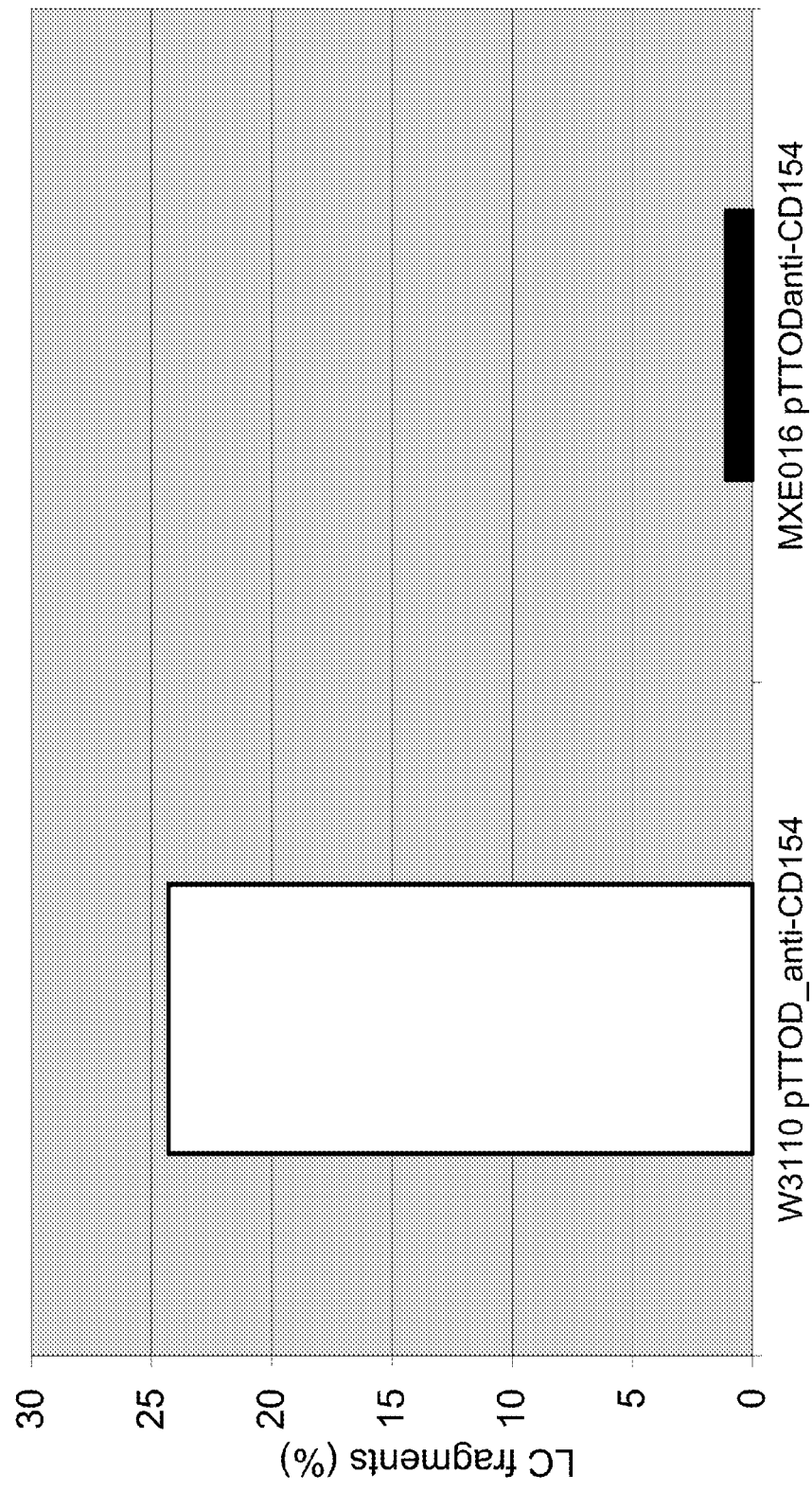
FIG. 5 shows the results of a reverse phase HPLC analysis of fermentation extractions. The wild-type strain W3110 expressing anti-CD154 Fab' exhibits a high level of degraded Kappa light chains (light chain [LC] fragments). In contrast, strain MXE016 (W3110 ΔTsp, spr C94A) expressing recombinant DsbC and anti-CD154 Fab' exhibits hardly any light chain fragments due to the absence of Tsp protease activity.
Figure 6:
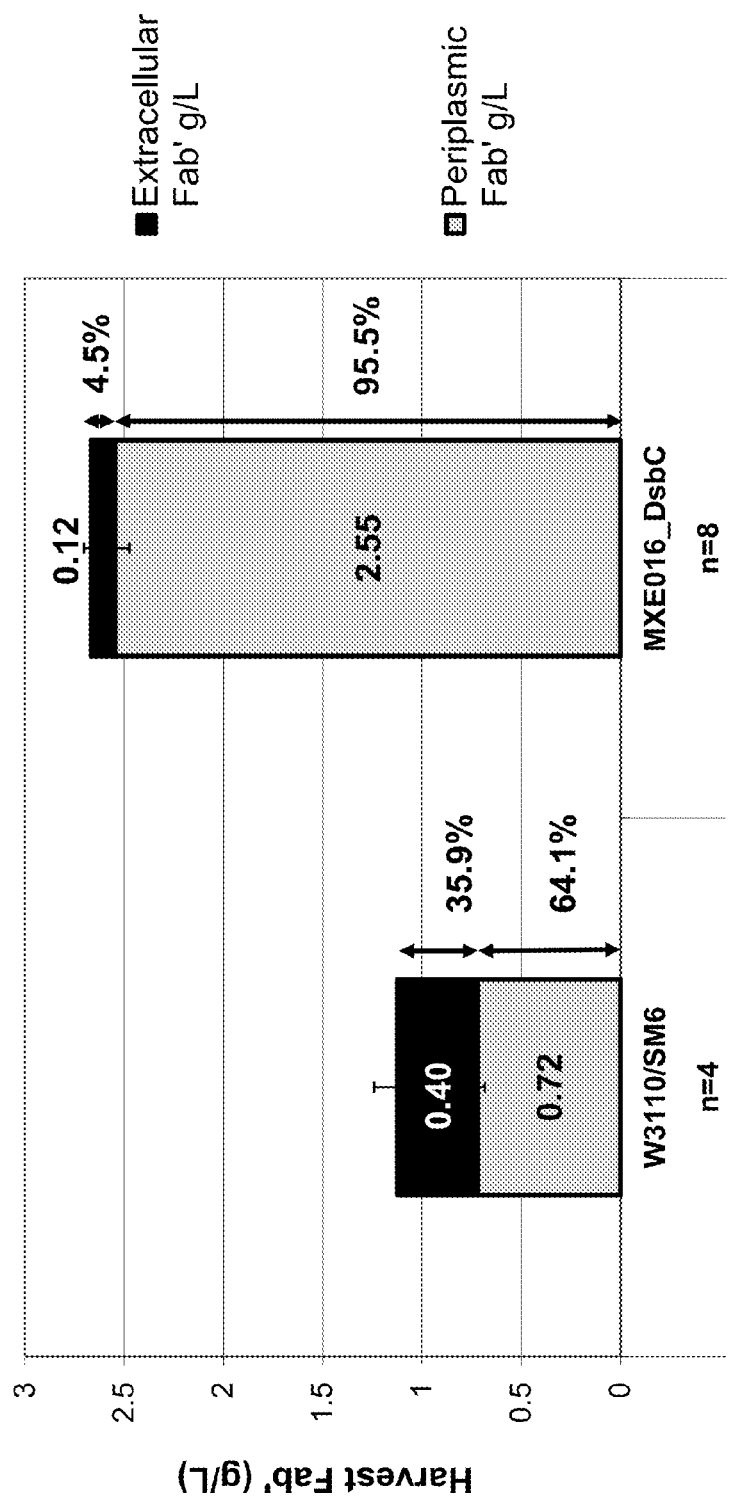
FIG. 6 shows the harvest of anti-CD154 Fab' (g/L) from fermentations in strain W3110 and in strain MXE016 (W3110 ΔTsp, spr C94A) expressing recombinant DsbC. The harvest from strain MXE016 (W3110 ΔTsp, spr C94A) expressing recombinant DsbC is substantially higher and exhibits substantially less extracellular Fab', which is beneficial as extracellular Fab' is a marker of cell lysis risk and the extracellular Fab is not easily recovered using the same process as used for periplasmic Fab'.
Figure 7:
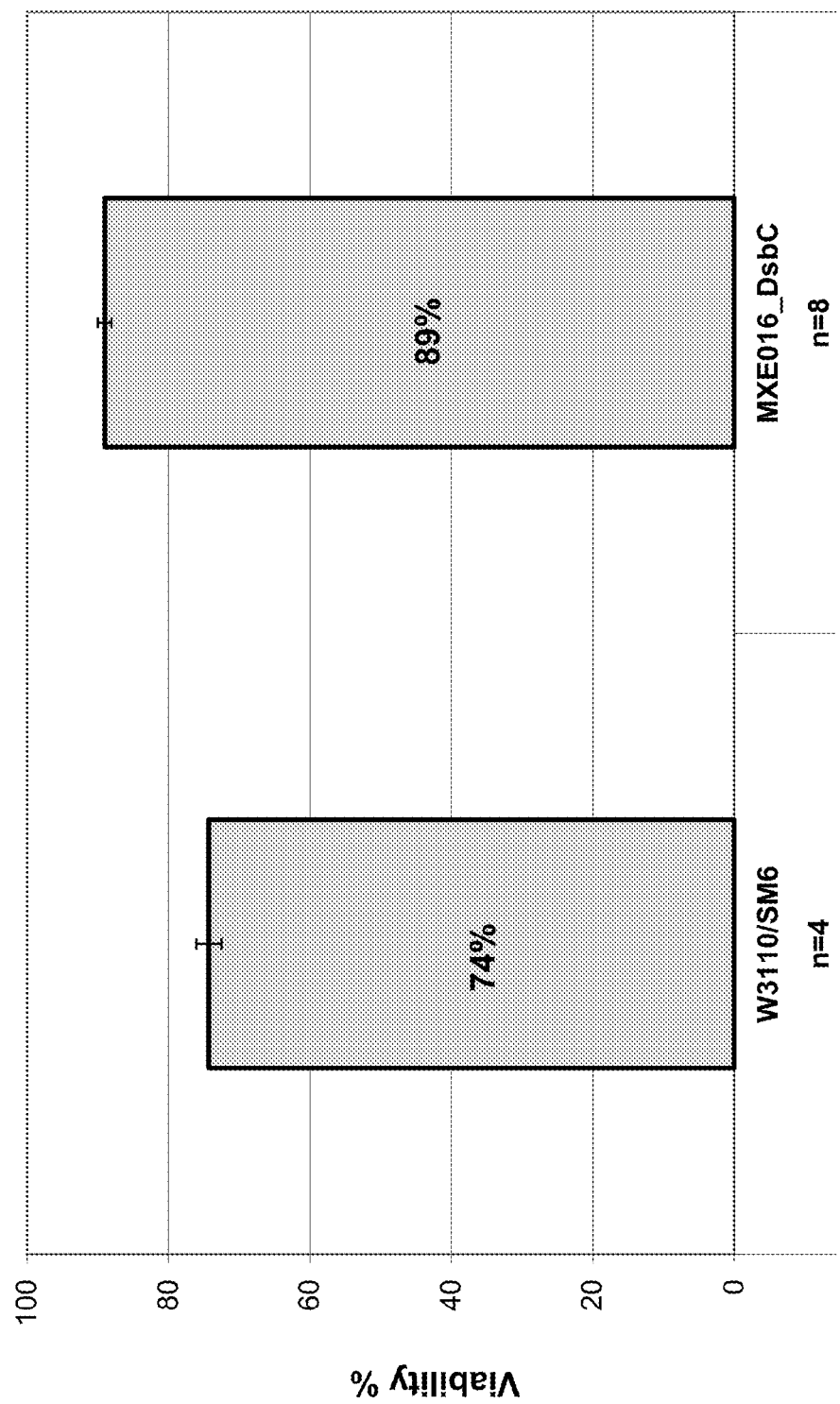
FIG. 7 shows the viability of (a) strain W3110 cells and (b) strain MXE016 (W3110 ΔTsp, spr C94A) cells expressing recombinant DsbC; in both cases (a) and (b) express anti-CD154 Fab' (g/L). The strain MXE016 cells (W3110 ΔTsp, spr C94A) expressing recombinant DsbC exhibit a higher viability.
Figure 8:
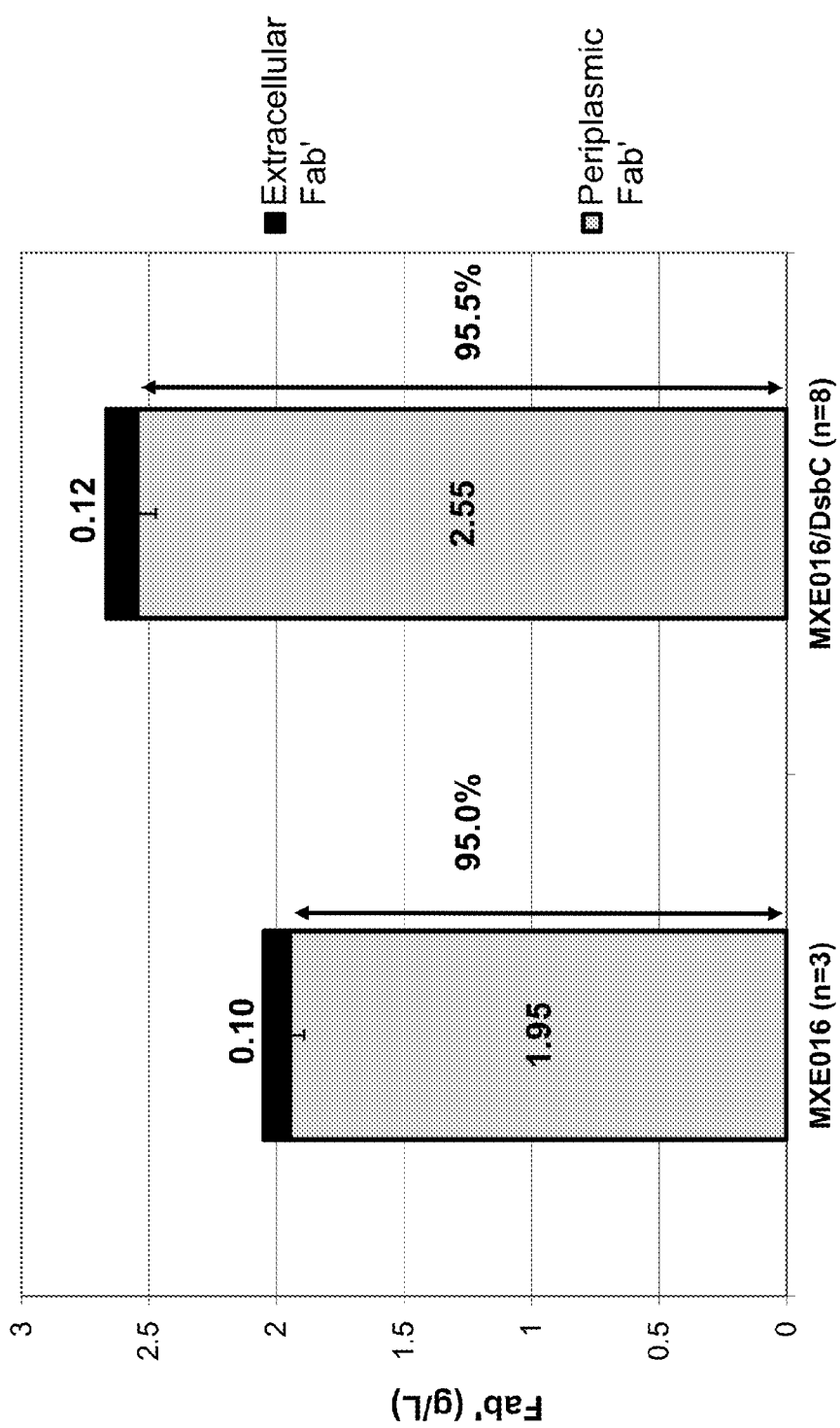
FIG. 8 shows total Fab' yield (g/L) from fermentations of MXE016 strains expressing anti-CD154 Fab'. The right bar represents an MXE016 strain expressing additionally recombinant DsbC. The MXE016 strain expressing recombinant DsbC exhibits a higher yield.

Advantageously the reduced Tsp protein activity and/or the co-expression of DsbC leads to reduced generation of the undesirable impurity referred to herein as the light chain fragment (LC), see for example FIG. 5.

The skilled person would easily be able to test a candidate cell clone to see if it has the desired yield of a protein of interest using methods well-known in the art, including a fermentation method, ELISA and protein G HPLC. Suitable fermentation methods are described in Humphreys et al. (193-202) and Backlund et al. (358-65), which are incorporated herein by reference in their entirety. The skilled person would also easily be able to test secreted protein to see if the protein is correctly folded using methods well-known in the art, such as protein G HPLC, circular dichroism, NMR, x-ray crystallography and epitope affinity measurement methods.

In one embodiment the cell according to the present invention also expresses or overexpresses, as compared to the corresponding wild-type cell (such as the *E. coli* W3110 K-12 strain), one or more further proteins as follows:
  one or more proteins capable of facilitating protein folding, such as FkpA, Skp, SurA, PPiA and PPiD;
  one or more proteins capable of facilitating protein secretion or translocation, such as SecY, SecE, SecG, SecYEG, SecA, SecB, FtsY and Lep; and/or
  one or more proteins capable of facilitating disulfide bond formation, such as DsbA, DsbB, DsbD, and DsbG.

One of more of the above proteins may be integrated into the cell's genome and/or inserted in an expression vector.

In one embodiment the cell according to the present invention does not express or expresses at a level which is at least 50%, 75% or 90% lower than the level of the corresponding wild-type cell (such as the *E. coli* W3110 K-12 strain) one or more of the following further proteins:
  one or more proteins capable of facilitating protein folding, such as FkpA, Skp, SurA, PPiA and PPiD;
  one or more proteins capable of facilitating protein secretion or translocation, such as SecY, SecE, SecG, SecYEG, SecA, SecB, FtsY and Lep; and
  one or more proteins capable of facilitating disulfide bond formation, such as DsbA, DsbB, DsbD, and DsbG.

In one embodiment the cell according to the present invention also expresses one or more further proteins selected from FkpA, Skp and a combination thereof.

In one embodiment the cell further comprises one or more of the following mutated genes:
  a) a mutated spr gene;
  b) a mutated Tsp gene, wherein the mutated Tsp gene encodes a Tsp protein having reduced protease activity or is a knockout mutated Tsp gene;
  c) a mutated DegP gene encoding a DegP protein having chaperone activity and reduced protease activity;
  d) a mutated ptr gene, wherein the mutated ptr gene encodes a Protease III protein having reduced protease activity or is a knockout mutated ptr gene; and
  e) a mutated OmpT gene, wherein the mutated OmpT gene encodes an OmpT protein having reduced protease activity, for example as shown in SEQ ID NO: 42, or is a knockout mutated OmpT gene, for example as shown in SEQ ID NO: 40.

In a basic embodiment of the invention the gram-negative bacterial cell does not carry a knockout mutated Tsp gene, such as being deficient in chromosomal Tsp.

The latter mutation is particular important in production of antibodies and fragments thereof specifically binding to CD154 because Tsp protease activity may result in cleavage of the antibody product in the elbow regions, thereby generating a by-product in significant quantities and reducing yield of the desired product.

Thus in one embodiment the cell according to the present invention comprises a mutated Tsp gene, wherein the mutated Tsp gene encodes a Tsp protein having reduced protease activity or is a knockout mutated Tsp gene and also encodes a DsbC protein in addition to an antibody or fragment specific to CD154.

In embodiments of the present invention the cell further comprises a mutated spr gene. The spr protein is an E. coli membrane-bound periplasmic protease.

The wild-type amino acid sequence of the Spr protein is shown in SEQ ID NO: 24 with the signal sequence at the N-terminus (amino acids 1-26 according to UniProt Accession Number P0AFV4). The amino acid numbering of the Spr protein sequence in the present invention includes the signal sequence. Accordingly, the amino acid 1 of the Spr protein is the first amino acid (Met) shown in SEQ ID NO: 24.

In the embodiments wherein the cell according to the present invention comprises a mutated spr gene, the mutated spr gene is preferably the cell's chromosomal spr gene. The mutated spr gene encodes an Spr protein capable of suppressing a disadvantageous phenotype associated with a cell comprising a mutated Tsp gene. Cells carrying a mutated Tsp gene may have a good cell growth rate but one limitation of these cells is their tendency to lyse, especially at high cell densities. Accordingly the phenotype of a cell comprising a mutated Tsp gene is a tendency to lyse, especially at high cell densities.

Cells carrying a mutated Tsp gene show thermosensitive growth at low osmolarity. However, the spr mutations carried by the cells of the present invention, when introduced into a cell having reduced Tsp activity, suppress this phenotype of thermosensitive growth at low osmolarity and the cell exhibits reduced lysis, particularly at high cell densities. This "thermosensitive growth" phenotype of a cell may be easily measured by a person skilled in the art during the shake flask or high cell density fermentation technique. The suppression of the cell lysis is apparent from the improved growth rate and/or recombinant protein production, particularly in the periplasm, exhibited by a cell carrying the spr mutant and having reduced Tsp activity compared to a cell carrying the Tsp mutant and a wild-type spr.

The cells according to the present invention preferably comprise a mutant spr gene encoding an spr protein having a change of one or more amino acids selected from N31, R62, I70, Q73, C94, S95, V98, Q99, R100, L108, Y115, D133, V135, L136, G140, R144, H145, G147, H157 and W174, more preferably at one or more amino acids selected from C94, S95, V98, Y115, D133, V135, H145, G147, H157 and W174. Preferably the mutant spr gene encodes a spr protein having a change of one or more amino acids selected from N31, R62, I70, Q73, C94, S95, V98, Q99, R100, L108, Y115, D133, V135, L136, G140, R144, H145, G147 and H157, more preferably at one or more amino acids selected from C94, S95, V98, Y115, D133, V135, H145, G147 and H157. In this embodiment, the spr protein preferably does not have any further amino acid changes. Preferably, the mutant spr gene encodes an spr protein having a change of one or more amino acids selected from N31, R62, I70, Q73, S95, V98, Q99, R100, L108, Y115, D133, V135, L136, G140, R144 and G147, more preferably at one or more amino acids selected from S95, V98, Y115, D133, V135 and G147. In this embodiment, the spr protein preferably does not have any further amino acid changes.

The present inventors have identified spr changes which are capable of suppressing the growth phenotype of a cell comprising a mutated Tsp gene.

The inventors have also surprisingly found that cells carrying a recombinant DsbC gene and a mutated spr gene and having reduced Tsp protein activity compared to a wild-type cell exhibit increased cell growth rate and increased cell survival duration compared to a cell comprising a mutated Tsp gene. Specifically, cells carrying a recombinant DsbC gene and a change in the spr protein and having reduced Tsp protein activity exhibit reduced cell lysis during cultivation compared to cells carrying a mutated Tsp gene.

The change of one or more of the above spr amino acids may be the result of any suitable missense mutation to one, two or three of the nucleotides encoding the amino acid. The mutation changes the amino acid residue to any suitable amino acid which results in a mutated spr protein capable of suppressing the phenotype of a cell comprising a mutated Tsp gene. The missense mutation may change the amino acid to one which is a different size and/or has different chemical properties compared to the wild-type amino acid.

In one embodiment the change is with respect to one, two or three of the catalytic triad of amino acid residues of C94, H145, and H157 (Aramini et al. 9715-17).

Accordingly, the mutated spr gene may comprise:
a mutation affecting the amino acid C94;
a mutation affecting the amino acid H145;
a mutation affecting the amino acid H157;
a mutation affecting the amino acids C94 and H145;
a mutation affecting the amino acids C94 and H157;
a mutation affecting the amino acids H145 and H157; or
a mutation affecting the amino acids C94, H145 and H157.

In this embodiment, the spr protein preferably does not have any further amino acid changes.

One, two or three of C94, H145 and H157 may be changed to any suitable amino acid which results in an spr protein capable of suppressing the phenotype of a cell comprising a mutated Tsp gene. For example, one, two or three of C94, H145, and H157 may be changed to a small amino acid such as Gly or Ala. Accordingly, the spr protein may have one, two or three of the mutations resulting in C94A (i.e., cysteine at position 94 changed to alanine), H145A (i.e., histidine at position 145 changed to alanine) and H157A (i.e., histidine at position 157 changed to alanine). Preferably, the spr gene comprises the missense mutation leading to H145A, which has been found to produce an spr protein capable of suppressing the phenotype of a cell comprising a mutated Tsp gene.

The designation for a substitution mutant herein consists of a letter followed by a number followed by a letter. The first letter designates the amino acid in the wild-type protein, the number refers to the amino acid position where the amino acid substitution is being made, and the second letter designates the amino acid that is used to replace the wild-type amino acid.

In a preferred embodiment the mutant spr protein comprises a change of one or more amino acids selected from N31, R62, I70, Q73, S95, V98, Q99, R100, L108, Y115, D133, V135, L136, G140, R144 and G147, preferably a change of one or more amino acids selected from S95, V98, Y115, D133, V135 and G147. In this embodiment, the spr protein preferably does not have any further mutations. Accordingly, the mutated spr gene may comprise:

a mutation affecting the amino acid N31;
a mutation affecting the amino acid R62;
a mutation affecting the amino acid I70;
a mutation affecting the amino acid Q73;
a mutation affecting the amino acid S95;
a mutation affecting the amino acid V98;
a mutation affecting the amino acid Q99;
a mutation affecting the amino acid R100;
a mutation affecting the amino acid L108;
a mutation affecting the amino acid Y115;
a mutation affecting the amino acid D133;
a mutation affecting the amino acid V135;
a mutation affecting the amino acid L136;
a mutation affecting the amino acid G140;
a mutation affecting the amino acid R144; or
a mutation affecting the amino acid G147.

In one embodiment the mutant spr gene comprises multiple mutations affecting the amino acids:

S95 and Y115;
N31, Q73, R100 and G140;
Q73, R100 and G140;
R100 and G140;
Q73 and G140;
Q73 and R100;
R62, Q99 and R144; or
Q99 and R144.

One or more of the amino acids N31, R62, I70, Q73, S95, V98, Q99, R100, L108, Y115, D133, V135, L136, G140, R144 and G147 may be changed to any suitable amino acid which results in an spr protein capable of suppressing the phenotype of a cell comprising a mutated Tsp gene. For example, one or more of N31, R62, I70, Q73, S95, V98, Q99, R100, L108, Y115, D133, V135, L136, G140 and R144 may be changed to a small amino acid such as Gly or Ala.

In a preferred embodiment the spr protein comprises one or more of the following changes: N31Y, R62C, I70T, Q73R, S95F, V98E, Q99P, R100G, L108S, Y115F, D133A, V135D or V135G, L136P, G140C, R144C and G147C. Preferably the spr protein comprises one or more of the following changes: S95F, V98E, Y115F, D133A, V135D or V135G and G147C. In this embodiment, the spr protein preferably does not have any further amino acid changes.

In one embodiment the spr protein has only one amino acid change selected from N31Y, R62C, I70T, Q73R, C94A, S95F, V98E, Q99P, R100G, L108S, Y115F, D133A, V135D or V135G, L136P, G140C, R144C and G147C, in particular C94A. In this embodiment, the spr protein preferably does not have any further amino acid changes.

In a further embodiment the spr protein has multiple changes selected from:

S95F and Y115F;
N31Y, Q73R, R100G and G140C;
Q73R, R100G and G140C;
R100G and G140C;
Q73R and G140C;
Q73R and R100G;
R62C, Q99P and R144C; or
Q99P and R144C.

Preferably, the mutant spr gene encodes an spr protein having amino acid changes selected from C94A, D133A, H145A and H157A, in particular C94A.

In a further embodiment the mutated spr gene encodes an spr protein having the amino acid change W174R. In an alternative embodiment the spr protein does not have the amino acid change W174R.

The cell according to the present invention has reduced Tsp protein activity compared to a wild-type cell. The expression "reduced Tsp protein activity compared to a wild-type cell" means that the Tsp activity of the cell is reduced compared to the Tsp activity of a wild-type cell. The cell may be modified by any suitable means to reduce the activity of Tsp.

In one embodiment the reduced Tsp activity is from modification of the endogenous polynucleotide encoding Tsp and/or associated regulatory expression sequences. The modification may reduce or stop Tsp gene transcription and translation or may provide an expressed Tsp protein having reduced protease activity compared to the wild-type Tsp protein.

In one embodiment an associated regulatory expression sequence is modified to reduce Tsp expression. For example, the promoter for the Tsp gene may be mutated to prevent expression of the gene.

In a preferred embodiment the cell according to the present invention carries a mutated Tsp gene encoding a Tsp protein having reduced protease activity or a knockout mutated Tsp gene. Preferably the chromosomal Tsp gene is mutated.

As used herein, "Tsp gene" means a gene encoding protease Tsp (also known as Prc) which is a periplasmic protease capable of acting on Penicillin-binding protein-3 (PBP3) and phage tail proteins. The sequence of the wild-type Tsp gene is shown in SEQ ID NO: 25 and the sequence of the wild-type Tsp protein is shown in SEQ ID NO: 26.

Reference to the mutated Tsp gene or mutated Tsp gene encoding Tsp refers to either a mutated Tsp gene encoding a Tsp protein having reduced protease activity or a knockout mutated Tsp gene, unless otherwise indicated.

The expression "mutated Tsp gene encoding a Tsp protein having reduced protease activity" in the context of the present invention means that the mutated Tsp gene does not have the full protease activity compared to the wild-type non-mutated Tsp gene.

Preferably, the mutated Tsp gene encodes a Tsp protein having 50% or less, 40% or less, 30% or less, 20% or less, 10% or less or 5% or less of the protease activity of a wild-type non-mutated Tsp protein. More preferably, the mutated Tsp gene encodes a Tsp protein having no protease activity. In this embodiment the cell is not deficient in chromosomal Tsp, i.e., the Tsp gene sequence has not been deleted or mutated to prevent expression of any form of Tsp protein.

Any suitable mutation may be introduced into the Tsp gene in order to produce a protein having reduced protease activity. The protease activity of a Tsp protein expressed from a gram-negative bacterium may be easily tested by a person skilled in the art by any suitable method in the art, such as the method described in Keiler et al. (Keiler and Sauer 28864-68), which is incorporated by reference herein in its entirety, wherein the protease activity of Tsp was tested.

Tsp has been reported in Keiler et al. (supra) as having an active site comprising residues S430, D441 and K455 and residues G375, G376, E433 and T452 are important for maintaining the structure of Tsp. Keiler et al. (supra) reports findings that the mutated Tsp genes leading to the amino acid changes S430A, D441A, K455A, K455H, K455R, G375A, G376A, E433A and T452A had no detectable protease activity. It is further reported that the mutated Tsp gene leading to S430C displayed about 5-10% wild-type activity. Accordingly, the Tsp mutation to produce a protein having reduced protease activity may comprise a mutation, such as a missense mutation, leading to a change of one or more of residues S430, D441, K455, G375, G376, E433 and T452. Preferably the Tsp mutation to produce a protein having reduced protease activity may comprise a mutation, such as a missense mutation, affecting one, two or all three of the active site residues S430, D441 and K455.

Accordingly the mutated Tsp gene may comprise:
a mutation affecting the amino acid S430;
a mutation affecting the amino acid D441;
a mutation affecting the amino acid K455;
a mutation affecting the amino acids S430 and D441;
a mutation affecting the amino acids S430 and K455;
a mutation affecting the amino acids D441 and K455; or
a mutation affecting the amino acids S430, D441 and K455.

One or more of residues S430, D441, K455, G375, G376, E433 and T452 may be changed to any suitable amino acid which results in a protein having reduced protease activity. Examples of suitable changes are S430A, S430C, D441A, K455A, K455H, K455R, G375A, G376A, E433A and T452A. The mutated Tsp gene may comprise one, two or three mutations leading to changes to the active site residues; for example the gene may comprise:
S430A or S430C; and/or
D441A; and/or
K455A or K455H or K455R.

Preferably, the Tsp gene has the mutation leading to S430A or S430C.

The expression "knockout mutated Tsp gene" in the context of the present invention means that the Tsp gene comprises one or more mutations which prevent expression of the Tsp protein encoded by the wild-type gene to provide a cell deficient in Tsp protein. The knockout gene may be partially or completely transcribed but not translated into the encoded protein. The knockout mutated Tsp gene may be mutated in any suitable way, for example by one or more deletion, insertion, point, missense, nonsense and frameshift mutations, to cause no expression of the protein. For example, the gene may be knocked out by insertion of a foreign DNA sequence, such as an antibiotic resistance marker, into the gene coding sequence.

In a preferred embodiment the Tsp gene is not mutated by insertion of a foreign DNA sequence, such as an antibiotic resistance marker, into the gene coding sequence. In one embodiment the Tsp gene comprises a mutation to the gene start codon and/or one or more stop codons positioned downstream of the gene start codon and upstream of the gene stop codon, thereby preventing expression of the Tsp protein. The mutation to the start codon may be a missense mutation of one, two or all three of the nucleotides of the start codon. Alternatively or additionally the start codon may be mutated by an insertion or deletion frameshift mutation. The Tsp gene comprises two ATG codons at the 5' end of the coding sequence; one or both of the ATG codons may be mutated by a missense mutation. The Tsp gene may be mutated at the second ATG codon (codon 3) to TCG, as shown in FIG. 10. The Tsp gene may alternatively or additionally comprise one or more stop codons positioned downstream of the gene start codon and upstream of the gene stop codon. Preferably the knockout mutated Tsp gene comprises both a missense mutation to the start codon and one or more inserted stop codons. In a preferred embodiment the Tsp gene is mutated to delete "T" from the fifth codon, thereby causing a frameshift resulting in stop codons at codons 11 and 16, as shown in FIG. 10. In a preferred embodiment the Tsp gene is mutated to insert an Ase I restriction site to create a third in-frame stop codon at codon 21, as shown in FIG. 10.

In a preferred embodiment the knockout mutated Tsp gene has the DNA sequence of SEQ ID NO: 25, which includes the 6 nucleotides ATGAAT upstream of the start codon. The mutations which have been made in the knockout mutated Tsp sequence of SEQ ID NO: 25 are shown in FIG. 10. In one embodiment the mutated Tsp gene has the DNA sequence of nucleotides 7 to 2048 of SEQ ID NO: 25.

In embodiments of the present invention the cell comprises a mutated DegP gene. As used herein, "DegP" means a gene encoding DegP protein (also known as HtrA), which has dual function as a chaperone and a protease. The sequence of the wild-type DegP gene is shown in SEQ ID NO: 29 and the sequence of the non-mutated DegP protein is shown in SEQ ID NO: 30.

At low temperatures DegP functions as a chaperone and at high temperatures DegP has a preference to function as a protease.

In the embodiments where the cell comprises the DegP mutation, the DegP mutation in the cell provides a mutated DegP gene encoding a DegP protein having chaperone activity but not full protease activity.

The expression "having chaperone activity" in the context of the present invention means that the mutated DegP protein has the same or substantially the same chaperone activity compared to the wild-type non-mutated DegP protein. Preferably, the mutated DegP gene encodes a DegP protein having 50% or more, 60% or more, 70% or more, 80% or more, 90% or more or 95% or more of the chaperone activity of a wild-type non-mutated DegP protein. More preferably, the mutated DegP gene encodes a DegP protein having the same chaperone activity compared to wild-type DegP.

The expression "having reduced protease activity" in the context of the present invention means that the mutated DegP protein does not have the full protease activity compared to the wild-type non-mutated DegP protein. Preferably, the mutated DegP gene encodes a DegP protein having 50% or less, 40% or less, 30% or less, 20% or less, 10% or less or 5% or less of the protease activity of a wild-type non-mutated DegP protein. More preferably, the mutated DegP gene encodes a DegP protein having no protease activity. The cell is not deficient in chromosomal DegP, i.e., the DegP gene sequence has not been deleted or mutated to prevent expression of any form of DegP protein.

Any suitable mutation may be introduced into the DegP gene in order to produce a protein having chaperone activity and reduced protease activity. The protease and chaperone activity of a DegP protein expressed from a gram-negative bacterium may be easily tested by a person skilled in the art by any suitable method, e.g., wherein the protease and chaperone activities of DegP are tested on Mal S, a natural substrate of DegP.

DegP is a serine protease and has an active center consisting of a catalytic triad of amino acid residues of His105, Asp135 and Ser210. The DegP mutation to produce a protein having chaperone activity and reduced protease activity may comprise a mutation, such as a missense mutation, affecting one, two or three of His105, Asp135 and Ser210.

Accordingly, the mutated DegP gene may comprise:
a mutation affecting the amino acid His105;
a mutation affecting the amino acid Asp135;
a mutation affecting the amino acid Ser210;
a mutation affecting the amino acids His105 and Asp135;
a mutation affecting the amino acids His105 and Ser210;
a mutation affecting the amino acids Asp135 and Ser210; or
a mutation affecting the amino acids His105, Asp135 and Ser210.

One, two or three of His105, Asp135 and Ser210 may be changed to any suitable amino acid which results in a protein having chaperone activity and reduced protease activity. For example, one, two or three of His105, Asp135 and Ser210 may be changed to a small amino acid such as Gly or Ala. A further suitable mutation is to change one, two or three of His105, Asp135 and Ser210 to an amino acid having opposite properties, such as Asp135 being changed to Lys or Arg, polar His105 being changed to a non-polar amino acid such as Gly, Ala, Val or Leu and small hydrophilic Ser210 being changed to a large or hydrophobic residue such as Val, Leu, Phe or Tyr. Preferably, the DegP gene comprises the alteration S210A, as shown in FIG. 11, which has been found to produce a protein having chaperone activity but not protease activity.

DegP has two PDZ domains, PDZ1 (residues 260-358) and PDZ2 (residues 359-448), which mediate protein-protein interaction. In one embodiment of the present invention the DegP gene is mutated to delete the PDZ1 domain and/or the PDZ2 domain. The deletion of PDZ1 and PDZ2 results in complete loss of protease activity of the DegP protein and lowered chaperone activity compared to wild-type DegP protein, while deletion of either PDZ1 or PDZ2 results in 5% protease activity and similar chaperone activity compared to wild-type DegP protein.

The mutated DegP gene may also comprise a silent non-naturally occurring restriction site, such as Ase I, in order to aid in identification and screening methods, for example as shown in FIG. 11.

The preferred sequence of the mutated DegP gene comprising the point mutation S210A and an Ase I restriction marker site is provided in SEQ ID NO: 31 and the encoded protein sequence is shown in SEQ ID NO: 27. The mutations which have been made in the mutated DegP sequence of SEQ ID NO: 32 are shown in FIG. 11.

In the embodiments of the present invention wherein the cell comprises a mutated DegP gene encoding a DegP protein having chaperone activity and reduced protease activity, one or more of the cells provided by the present invention may provide an improved yield of correctly folded proteins from the cell relative to mutated cells wherein the DegP gene has been mutated to knockout DegP, preventing DegP expression, such as chromosomal deficient DegP. In a cell comprising a knockout mutated DegP gene preventing DegP expression, the chaperone activity of DegP is lost completely, whereas in the cell according to the present invention the chaperone activity of DegP is retained while the full protease activity is lost. In these embodiments, one or more cells according to the present invention have a lower protease activity to prevent proteolysis of the protein while maintaining the chaperone activity to allow correct folding and transportation of the protein in the host cell.

In one embodiment the gram-negative bacterial cell according to the present invention does not carry a knockout mutated OmpT gene, such as being deficient in chromosomal OmpT (SEQ ID NO: 39).

In one embodiment the gram-negative bacterial cell according to the present invention does not carry a knockout mutated DegP gene, such as being deficient in chromosomal DegP. In one embodiment the gram-negative bacterial cell according to the present invention does not carry a mutated DegP gene.

In one embodiment the gram-negative bacterial cell according to the present invention does not carry a knockout mutated ptr gene, such as being deficient in chromosomal ptr.

In one embodiment the gram-negative bacterial cell according to the present invention does not carry a mutated spr gene.

Any suitable gram-negative bacterium may be used as the parental cell for producing the recombinant cell of the present invention. Suitable gram-negative bacterium include *Salmonella typhimurium, Pseudomonas fluorescens, Envinia carotovora, Shigella, Klebsiella pneumoniae, Legionella pneumophila, Pseudomonas aeruginosa, Acinetobacter baumannii* and *E. coli*. Preferably the parental cell is *E. coli*. Any suitable strain of *E. coli* may be used in the present invention but preferably a wild-type W3110 strain, such as K-12 W3110, is used.

A drawback associated with strains previously created and used to express recombinant proteins involves the use of mutations of genes involved in cell metabolism and DNA replication, such as phoA, fhuA, lac, rec, gal, ara, arg, thi and pro in *E. coli* strains. These mutations may have many deleterious effects on the host cell including effects on cell growth, stability, periplasmic leakage, recombinant protein expression yield and toxicity. Strains having one or more of these genomic mutations, particularly strains having a high number of these mutations, may exhibit a loss of fitness which reduces bacterial growth rate to a level which is not suitable for industrial protein production. Further, any of the above genomic mutations may affect other genes in cis and/or in trans in unpredictable harmful ways, thereby altering the strain's phenotype, fitness and protein profile. Further, the use of heavily mutated cells is not generally suitable for producing recombinant proteins for commercial use, particularly therapeutics, because such strains generally have defective metabolic pathways and hence may grow poorly or not at all in minimal or chemically defined media.

In a preferred embodiment, the cells carry only the minimal mutations to introduce the recombinant polynucleotide encoding DsbC and the one or more polynucleotides encoding the antibody or antigen-binding fragment thereof and optionally a mutation resulting in reduced Tsp protease activity and optionally an spr gene or a mutant thereof.

In one embodiment wherein the polynucleotide encoding DsbC and/or the one or more polynucleotides encoding the antibody or antigen-binding fragment thereof are inserted into the cell's genome only minimal mutations are made to the cell's genome to introduce the recombinant polynucleotide encoding DsbC and/or the antibody. In a further embodiment wherein the recombinant polynucleotide encoding DsbC and the polynucleotide encoding the antibody are present in the same or different expression vectors, the genome is preferably isogenic to a wild-type cell genome.

In one embodiment the cells do not carry any other mutations which may have deleterious effects on the cell's growth and/or ability to express a protein of interest. Accordingly, one or more of the recombinant host cells of the present invention may exhibit improved protein expression and/or improved growth characteristics compared to cells comprising genetically engineered mutations to the genomic sequence. The cells provided by the present invention are also more suitable for use to produce therapeutic proteins compared to cells comprising disruptions to the cell genome.

In a preferred embodiment, the cell is isogenic to a wild-type *E. coli* cell except for the recombinant polynucleotide encoding DsbC and the one or more polynucleotides encoding an antibody or antigen-binding fragment thereof specifically binding to CD154 and optionally a mutation resulting in reduced Tsp protease activity and optionally an spr gene or a mutant thereof.

In one embodiment there is provided a cell isogenic to an *E. coli* strain W3110 except with reduced Tsp activity and an spr gene or a mutant thereof, for use with a plasmid suitable for expressing DsbC and an antibody or an antigen-binding fragment thereof specifically binding to CD154.

More preferably the cell according to the present invention is isogenic to an *E. coli* strain W3110 except for the recombinant polynucleotide encoding DsbC and the one or more polynucleotides encoding an antibody or an antigen-binding fragment thereof specifically binding to CD154.

The cell provided by the present invention comprises one or more polynucleotides encoding an antigen-binding antibody fragment with specificity for CD154.

A cell comprising as employed herein is intended to refer to where the entity concerned is integrated into the cell's genome or where the cell contains a vector such as a plasmid containing and generally for expressing the entity.

The antibody or antibody fragment may be multi-valent, multi-specific, humanized, fully human or chimeric. The antibody or antibody fragment can be from any species but is preferably derived from a monoclonal antibody, a human antibody, or a humanized fragment. The antibody fragment can be derived from any class (e.g., IgG, IgE, IgM, IgD or IgA) or subclass of immunoglobulin molecule and may be obtained from any species including, for example, mouse, rat, shark, rabbit, pig, hamster, camel, llama, goat or human. Parts of the antibody fragment may be obtained from more than one species; for example the antibody fragments may be chimeric. In one example the constant regions are from one species and the variable regions from another.

The antibody fragment may be a VH, VL, VHH, Fab, modified Fab, Fab', F(ab')$_2$ or Fv fragment; a light chain or heavy chain monomer or dimer; or a diabody, triabody, tetrabody, minibody, domain antibody or single-chain antibody, e.g., a single-chain Fv in which the heavy and light chain variable domains are joined by a peptide linker, Fab-Fv, or dual specificity antibody, such as a Fab-dAb, as described in WO 2009/040562. Similarly, the heavy and light chain variable regions may be combined with other antibody domains as appropriate. Antibody fragments are known in the art (Holliger and Hudson 1126-36).

The antibody specifically binding to CD154 is preferably the antibody 342 described in WO 2008/118356 (the contents of which are incorporated herein by reference) or comprises the CDRs or variable heavy and light chain regions of the antibody 342 described in WO 2008/118356. The antibody fragment specifically binding to CD154 is preferably derived from the antibody 342 described in WO 2008/118356 and/or comprises the CDRs or variable heavy and light chain regions of said antibody.

In a one embodiment the antibody or antibody fragment specifically binding to CD154 comprises a heavy chain wherein the variable domain comprises three CDRs, wherein the CDRs are selected from SEQ ID NO: 1 for CDRH1, SEQ ID NO: 2 for CDRH2 and SEQ ID NO: 3 for CDRH3.

In one embodiment the antibody or antibody fragment specifically binding to CD154 comprises a light chain wherein the variable domain comprises three CDRs, wherein the CDRs are selected from SEQ ID NO: 4 for CDRL1, SEQ ID NO: 5 for CDRL2 and SEQ ID NO: 6 for CDRL3.

In one embodiment the antibody or antibody fragment specifically binding to CD154 comprises a heavy chain comprising the sequence of SEQ ID NO: 1 for CDRH1, the sequence of SEQ ID NO: 2 for CDRH2 and the sequence of SEQ ID NO: 3 for CDRH3.

In one embodiment the antibody or antibody fragment specifically binding to CD154 comprises a light chain comprising the sequence of SEQ ID NO: 4 for CDRL1, the sequence of SEQ ID NO: 5 for CDRL2 and the sequence of SEQ ID NO: 6 for CDRL3.

In one embodiment the antibody or antibody fragment specifically binding to CD154 comprises a heavy chain comprising the sequence of SEQ ID NO: 1 for CDRH1, the sequence of SEQ ID NO: 2 for CDRH2 and the sequence of SEQ ID NO: 3 for CDRH3 and a light chain comprising the sequence of SEQ ID NO: 4 for CDRL1, the sequence of SEQ ID NO: 5 for CDRL2 and the sequence of SEQ ID NO: 6 for CDRL3.

The antibody is preferably a CDR-grafted antibody molecule and typically the variable domain comprises human acceptor framework regions and non-human donor CDRs.

Preferably, the antibody comprises the light chain variable domain (SEQ ID NO: 7) and the heavy chain variable domain (SEQ ID NO: 9).

Preferably the antibody is a Fab fragment. Preferably the Fab fragment has a heavy chain comprising or consisting of the sequence given as SEQ ID NO: 14 and a light chain comprising or consisting of the sequence given as SEQ ID NO: 12. The amino acid sequences given in SEQ ID NO: 14 and SEQ ID NO: 12 are preferably encoded by the nucleotide sequences given in SEQ ID NO: 13 and SEQ ID NO: 11, respectively.

Alternatively, it is preferred that the antibody fragment is a modified Fab fragment wherein the modification is the addition to the C-terminal end of its heavy chain one of or more amino acids to allow the attachment of an effector or reporter molecule. Preferably, the additional amino acids form a modified hinge region containing one or two cysteine residues to which the effector or reporter molecule may be attached as known in the art (see, e.g., WO 98/25971, which is incorporated herein in its entirety).

The cell according to the present invention comprises a DNA sequence encoding the antibody. Preferably, the DNA sequence encodes the heavy and the light chain of the antibody.

In one preferred embodiment, the DNA sequence encodes a light chain and comprises the sequence shown herein.

The DNA sequence of the present invention may comprise synthetic DNA, for instance produced by chemical processing, cDNA, genomic DNA or any combination thereof.

The constant region domains of the antibody, if present, may be selected with regard to the proposed function of the antibody molecule, and in particular the effector functions which may be required. For example, the constant region domains may be human IgA, IgD, IgE, IgG or IgM domains. In particular, human IgG constant region domains may be used, especially of the IgG$_1$ and IgG$_3$ isotypes when the antibody molecule is intended for therapeutic uses and antibody effector functions are required. Alternatively, IgG$_2$ and IgG$_4$ isotypes may be used when the antibody molecule is intended for therapeutic purposes and antibody effector functions are not required, e.g., for simply blocking CD154 activity.

The antibody may be useful in the treatment of diseases or disorders including inflammatory diseases and disorders, immune disease and disorders, fibrotic disorders and cancers.

The terms "inflammatory disease" or "autoimmune disorder" and "immune disease or disorder" include rheumatoid arthritis, psoriatic arthritis, ankylosing spondylitis, juvenile arthritis, Still's disease, Hashimoto's thyroiditis, Graves' disease, Sjögren's syndrome, Goodpasture's syndrome, Addison's disease, vasculitis including ANCA-associated vasculitis and Wegener's granulomatosis, primary biliary cirrhosis, sclerosing cholangitis, autoimmune hepatitis polymyalgia rheumatica, Guillain-Barré syndrome, antiphospholipid syndrome, idiopathic thrombocytopaenia, autoimmune haemolytic anaemia, pernicious anaemia, pemphigus vulgaris, dermatomyositis, bullous pemphigoid, Henoch-Schönlein purpura, Muckle-Wells syndrome, psoriasis, Crohn's disease, ulcerative colitis, SLE (Systemic Lupus Erythematosus), celiac disease, asthma, allergic rhinitis, atopic dermatitis, multiple sclerosis, Type I diabetes mellitus, transplantation and graft-versus-host disease.

The term "fibrotic disorder" as used herein refers to a disorder characterized by the formation or development of excess fibrous connective tissue in an organ or tissue, frequently as a reparative or reactive process. A fibrotic disorder can affect single organs, such as the lungs (for example, without limitation, idiopathic pulmonary fibrosis, interstitial lung disease), the liver, the intestine, the kidney, the heart or the skin, or affect multiple organs, for example, without limitation, systemic sclerosis. The term "fibrotic disorder" also relates to scarring of the skin. Scars of the skin include, but are not limited to, keloid scars, contracture scars that occur, for example, without limitation, after skin burn, hypertrophic scars and acne scars.

The host cell of the invention may also comprise further polynucleotides encoding one or more further proteins of interest.

The recombinant gram-negative bacterial cell according to the present invention may be produced by any suitable means.

The skilled person knows suitable techniques which may be used to insert the recombinant polynucleotide encoding DsbC and the polynucleotide encoding the antibody. The recombinant polynucleotide encoding DsbC and/or the polynucleotide encoding the antibody may be integrated into the cell's genome using a suitable vector such as pKO3, described in Link et al., which is incorporated herein by reference in its entirety (Link, Phillips, and Church 6228-37).

Alternatively or additionally, the recombinant polynucleotide encoding DsbC and/or the polynucleotide encoding the antibody may be non-integrated in a recombinant expression cassette. In one embodiment an expression cassette is employed in the present invention to carry the polynucleotide encoding DsbC and/or the polynucleotide encoding the antibody, which typically comprises a protein coding sequence encoding DsbC, one or more protein coding sequences encoding the antibody and one or more regulatory expression sequences. The one or more regulatory expression sequences may include a promoter. The one or more regulatory expression sequences may also include a 3' untranslated region such as a termination sequence. Suitable promoters are discussed in more detail below.

In one embodiment the gene encoding DsbC and/or the antibody or fragment thereof is/are integrated into the genome of the host cell to create a stable cell line.

In one embodiment, the cell according to the present invention comprises one or more expression vectors, such as plasmids. The vector preferably comprises one or more of the expression cassettes as defined above. The host cell preferably comprises an expression vector comprising DNA encoding an antibody or an antigen-binding fragment thereof specifically binding to CD154 as described above. Preferably the expression vector comprises a polynucleotide sequence encoding a light chain and a polynucleotide sequence encoding a heavy chain of the antibody or an antigen-binding fragment thereof specifically binding to CD154.

In a preferred embodiment, the expression vector is an *E. coli* expression vector.

In one embodiment the polynucleotide sequence encoding the antibody and the polynucleotide sequence encoding DsbC are inserted into separate expression vectors.

For production of products comprising both heavy and light chains, the cell line may be transformed with two vectors, a first vector encoding a light chain polypeptide and a second vector encoding a heavy chain polypeptide. Alternatively, a single vector may be used, the vector including sequences encoding light chain and heavy chain polypeptides.

Alternatively, the polynucleotide sequence encoding the antibody and the polynucleotide encoding DsbC are inserted into one vector. Preferably the vector comprises the sequences encoding the light and heavy chain polypeptides of the antibody.

The present invention also provides an expression vector comprising a recombinant polynucleotide encoding DsbC and an antibody or an antigen-binding fragment thereof specifically binding to CD154. The expression vector is a multi-cistronic vector comprising the polynucleotide sequence encoding DsbC and the polynucleotide sequence encoding the antibody.

The multicistronic vector may be produced by an advantageous cloning method which allows repeated sequential cloning of polynucleotide sequences into a vector. The method uses compatible cohesive ends of a pair of restriction sites, such as the "AT" ends of AseI and NdeI restriction sites. A polynucleotide comprising a coding sequence and having compatible cohesive ends, such as an AseI-NdeI fragment, may be cloned into a restriction site in the vector, such as NdeI. The insertion of the polynucleotide sequence destroys the 5' restriction site but creates a new 3' restriction site, such as NdeI, which may then be used to insert a further polynucleotide sequence comprising compatible cohesive ends. The process may then be repeated to insert further sequences. Each polynucleotide sequence inserted into the vector comprises a non-coding sequence 3' to the stop codon which may comprise an Ssp I site for screening, a Shine-Dalgarno ribosome binding sequence, an A-rich spacer and an NdeI site encoding a start codon.

A diagrammatic representation of the creation of a vector comprising a polynucleotide sequence encoding a light chain of an antibody (LC), a heavy chain of an antibody (HC), a DsbC polynucleotide sequence and a further polynucleotide sequence is shown in FIG. 1.

The cell according to the present invention preferably comprises an expression vector as defined above.

In the embodiment wherein the cell also expresses one or more further proteins as follows:

one or more proteins capable of facilitating protein folding, such as FkpA, Skp, SurA, PPiA and PPiD;
one or more proteins capable of facilitating protein secretion or translocation, such as SecY, SecE, SecG, SecYEG, SecA, SecB, FtsY and Lep; and/or
one or more proteins capable of facilitating disulfide bond formation, such as DsbA, DsbB, DsbD, DsbG,
the one or more further proteins may be expressed from one or more polynucleotides inserted into the same vector as the polynucleotide encoding DsbC and/or the one or more polynucleotides encoding the antibody or antigen-binding fragment thereof specifically binding to CD154. Alternatively, the one or more polynucleotides may be inserted into separate vectors.

The expression vector may be produced by inserting one or more expression cassettes as defined above into a suitable vector. Alternatively, the regulatory expression sequences for directing expression of the polynucleotide sequence may be contained in the expression vector and thus only the encoding region of the polynucleotide may be required to complete the expression vector.

The polynucleotide encoding DsbC and/or the polynucleotide encoding the antibody or antigen-binding fragment thereof specifically binding to CD154 is suitably inserted into a replicable vector, typically an autonomously replicating expression vector, for expression in the cell under the control of a suitable promoter for the cell. Many vectors are known in the art for this purpose and the selection of the appropriate vector may depend on the size of the nucleic acid and the particular cell type.

Examples of expression vectors which may be employed to transform the host cell with a polynucleotide according to the invention include:
a plasmid, such as pBR322 or pACYC184;
a viral vector such as a bacterial phage; and/or
a transposable genetic element such as a transposon.

Such expression vectors usually comprise a plasmid origin of DNA replication, an antibiotic selectable marker, a promoter and transcriptional terminator separated by a multi-cloning site (expression cassette) and a DNA sequence encoding a ribosome binding site.

The promoters employed in the present invention can be linked to the relevant polynucleotide directly or can alternatively be located in an appropriate position, for example in a vector such that when the relevant polypeptide is inserted the relevant promoter can act on the same. In one embodiment the promoter is located before the encoding portion of the polynucleotide on which it acts, for example a relevant promoter before each encoding portion of polynucleotide. "Before" as used herein is intended to imply that the promoter is located at the 5' end in relation to the encoding polynucleotide portion.

The promoters may be endogenous or exogenous to the host cells. Suitable promoters include lac, tac, trp, phoA, Ipp, Arab, tet and T7.

One or more promoters employed may be inducible promoters. In the embodiment wherein the polynucleotide encoding DsbC and the polynucleotide encoding the antibody are inserted into one vector, the nucleotide sequences encoding DsbC and the antibody may be under the control of a single promoter or separate promoters. In the embodiment wherein the nucleotide sequences encoding DsbC and the antibody are under the control of separate promoters, the promoters may be independently inducible promoters.

Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA.

The expression vector preferably also comprises a dicistronic message for producing the antibody or antigen-binding fragment thereof as described in WO 03/048208 or WO 2007/039714 (the contents of which are incorporated herein by reference in their entirety). Preferably the upstream cistron contains DNA coding for the light chain of the antibody and the downstream cistron contains DNA coding for the corresponding heavy chain, and the dicistronic intergenic sequence (IGS) preferably comprises a sequence selected from IGS1 (SEQ ID NO: 33), IGS2 (SEQ ID NO: 34), IGS3 (SEQ ID NO: 35) and IGS4 (SEQ ID NO: 36).

A preferable expression vector comprises a tricistronic message for producing the light chain and the heavy chain of the antibody or antigen-binding fragment thereof as described above and a message for producing the recombinant DsbC, preferably comprising a his-tag.

The terminators may be endogenous or exogenous to the host cells. A suitable terminator is rrnB.

Further suitable transcriptional regulators including promoters and terminators and protein targeting methods may be found in Makrides et al., which is incorporated herein by reference in its entirety (Makrides 512-38).

The DsbC polynucleotide inserted into the expression vector preferably comprises the nucleic acid encoding the DsbC signal sequence and the DsbC coding sequence. The DsbC protein may also be directed to the periplasm by genetic fusion to other signal peptides, for example those from the proteins OmpA, MalB, PelB, PhoA, PhoS, LppA, and DsbA. The vector preferably contains a nucleic acid sequence that enables the vector to replicate in one or more selected host cells, preferably to replicate independently of the host chromosome. Such sequences are well-known for a variety of bacteria.

In one embodiment the DsbC and/or the protein of interest comprises a histidine-tag at the N-terminus and/or C-terminus.

The antibody molecule may be secreted from the cell or targeted to the periplasm by suitable signal sequences. Alternatively, the antibody molecules may accumulate within the cell's cytoplasm. Preferably the antibody molecule is targeted to the periplasm.

The polynucleotide encoding the antibody may be expressed as a fusion with another polypeptide, preferably a signal sequence or other polypeptide having a specific cleavage site at the N-terminus of the mature polypeptide. The heterologous signal sequence selected should be one that is recognized and processed by the host cell. For prokaryotic host cells that do not recognize and process the native or a eukaryotic polypeptide signal sequence, the signal sequence is substituted by a prokaryotic signal sequence. Suitable signal sequences include OmpA, PhoA, LamB, PelB, DsbA and DsbC. In an embodiment where the cell comprises a polynucleotide encoding a heavy chain of the antibody and a polynucleotide encoding a light chain of the antibody, each polynucleotide may comprise a signal sequence, such as OmpA.

Construction of suitable vectors containing one or more of the above-listed components employs standard ligation techniques. Isolated plasmids or DNA fragments are cleaved, tailored, and re-ligated in the form desired to generate the plasmids required. General methods by which the vectors may be constructed, transfection methods and culture methods are well-known to those skilled in the art.

Standard techniques of molecular biology may be used to prepare DNA sequences coding for the antibody. Desired DNA sequences may be synthesised completely or in part using oligonucleotide synthesis techniques. Site-directed mutagenesis and polymerase chain reaction (PCR) techniques may be used as appropriate.

Embodiments of the invention described herein with reference to the polynucleotide apply equally to alternative embodiments of the invention, for example vectors, expression cassettes and/or host cells comprising the components employed therein, as far as the relevant aspect can be applied to same.

The present invention also provides a method for producing an antibody or an antigen-binding fragment thereof specifically binding to CD154 comprising:

culturing a recombinant gram-negative bacterial cell as defined above in a culture medium under conditions effective to express the antibody or the antigen-binding fragment thereof specifically binding to CD154 and the recombinant polynucleotide encoding DsbC; and recovering the antibody or an antigen-binding fragment thereof specifically binding to CD154 from the periplasm of the recombinant gram-negative bacterial cell and/or the culture medium.

The gram-negative bacterial cell and antibody preferably employed in the method of the present invention are described in detail above.

The recombinant polynucleotide encoding DsbC and the polynucleotide encoding the antibody or antigen-binding fragment thereof specifically binding to CD154 may be incorporated into the host cell using any suitable means known in the art. As discussed above, typically the polynucleotide encoding DsbC and the polynucleotide encoding the antibody are incorporated as part of the same or separate expression vectors which are transformed into the cell.

The polynucleotide encoding DsbC and the polynucleotide encoding the antibody or antigen-binding fragment thereof specifically binding to CD154 can be transformed into a cell using standard techniques, for example employing rubidium chloride, PEG or electroporation.

The method according to the present invention may also employ a selection system to facilitate selection of stable cells which have been successfully transformed with the polynucleotide encoding the protein of interest. The selection system typically employs co-transformation of a polynucleotide encoding a selection marker. In one embodiment, each polynucleotide transformed into the cell further comprises a polynucleotide encoding one or more selection markers. Accordingly, the transformation of the polynucleotides encoding DsbC and the antibody or antigen-binding fragment thereof specifically binding to CD154 and the one or more polynucleotides encoding the marker occurs together and the selection system can be employed to select those cells which produce the desired proteins.

Cells able to express the one or more markers are able to survive/grow/multiply under certain artificially imposed conditions, for example the addition of a toxin or antibiotic, because of the properties endowed by the polypeptide/gene or polypeptide component of the selection system incorporated therein (e.g., antibiotic resistance). Those cells that cannot express the one or more markers are not able to survive/grow/multiply in the artificially imposed conditions. The artificially imposed conditions can be chosen to be more or less vigorous, as required.

Any suitable selection system may be employed in the present invention. Typically the selection system may be based on including in the vector one or more genes that provide resistance to a known antibiotic, for example a tetracycline, chloramphenicol, kanamycin or ampicillin resistance gene. Cells that grow in the presence of a relevant antibiotic can be selected as they express both the gene that gives resistance to the antibiotic and the desired protein.

An inducible expression system or a constitutive promoter may be used in the present invention to express the antibody and/or the DsbC. Suitable inducible expression systems and constitutive promoters are well-known in the art.

In one embodiment wherein the polynucleotide encoding DsbC and the polynucleotide encoding the antibody are under the control of the same or separate inducible promoters, the expression of the polynucleotide(s) encoding the antibody and the recombinant polynucleotide encoding DsbC is induced by adding an inducer to the culture medium.

Any suitable medium may be used to culture the transformed cell. The medium may be adapted for a specific selection system, for example the medium may comprise an antibiotic, to allow only those cells which have been successfully transformed to grow in the medium.

The cells obtained from the medium may be subjected to further screening and/or purification as required. The method may further comprise one or more steps to extract and purify the protein of interest as required.

The antibody or antigen-binding fragment thereof may be recovered and purified from the strain, including from the cytoplasm, periplasm, or supernatant. Suitable methods include fractionation on immunoaffinity or ion-exchange columns; ethanol precipitation; reversed-phase HPLC; hydrophobic-interaction chromatography; chromatography on silica; chromatography on an ion-exchange resin such as S-SEPHAROSE and DEAE; chromatofocusing; ammonium-sulfate precipitation; and gel filtration.

In one embodiment the method further comprises separating the antibody or antigen-binding fragment thereof from DsbC.

Antibodies or antigen-binding fragments thereof may be suitably separated from the culture medium, cytoplasm extract and/or periplasm extract by conventional antibody purification procedures such as protein A-Sepharose, protein G chromatography, protein L chromatography, thiophilic, mixed mode resins, His-tag, FLAGTag, hydroxylapatite chromatography, gel electrophoresis, dialysis, affinity chromatography, ammonium sulfate, ethanol or PEG fractionation/precipitation, ion exchange membranes, expanded bed adsorption chromatography (EBA) or simulated moving bed chromatography.

The method may also include a further step of measuring the quantity of expression of the protein of interest and selecting cells having high expression levels of the protein of interest.

One or more method steps described herein may be performed in combination in a suitable container such as a bioreactor.

After expression, the antibody may be further processed, for example by conjugation to another entity such as an effector molecule. Accordingly, the method according to the present invention may comprise a further step of attaching an effector molecule to the antibody.

The term "effector molecule" as used herein includes, for example, antineoplastic agents, drugs, toxins (such as enzymatically active toxins of bacterial or plant origin and fragments thereof, e.g., ricin and fragments thereof), biologically active proteins, for example enzymes, other antibodies or antibody fragments, synthetic or naturally occurring polymers, nucleic acids and fragments thereof, e.g., DNA, RNA and fragments thereof, radionuclides, particularly radio-iodide, radioisotopes, chelated metals, nanoparticles and reporter groups such as fluorescent compounds or compounds which may be detected by NMR or ESR spectroscopy. Effector molecules may be attached to the antibody or fragment thereof by any suitable method; for example an antibody fragment may be modified to attach at least one effector molecule as described in WO 2005/003171 or WO 2005/003170 (the contents of which are incorporated herein by reference in their entirety). WO 2005/003171 and WO 2005/003170 also describe suitable effector molecules.

The antibody may have a macrocycle, for chelating a heavy metal atom, or a toxin, such as ricin, attached to it by a covalent bridging structure. Alternatively, procedures of recombinant DNA technology may be used to produce an antibody molecule in which the Fc fragment (CH2, CH3 and hinge domains), the CH2 and CH3 domains or the CH3 domain of a complete immunoglobulin molecule has/have been replaced by, or has/have attached thereto by peptide linkage, a functional non-immunoglobulin protein, such as an enzyme or toxin molecule. In the embodiment wherein the antibody is a modified Fab fragment having at the C-terminal end of its heavy chain one or more amino acids to allow attachment of an effector or reporter molecule, the additional amino acids preferably form a modified hinge region containing one or two cysteine residues to which the effector or reporter molecule may be attached.

A preferred effector group is a polymer molecule, which may be attached to the modified Fab fragment to increase its half-life in vivo.

The polymer molecule may, in general, be a synthetic or a naturally occurring polymer, for example an optionally substituted straight or branched chain polyalkylene, polyalkenylene or polyoxyalkylene polymer or a branched or unbranched polysaccharide, e.g., a homo- or hetero-polysaccharide.

Particular optional substituents which may be present on the above-mentioned synthetic polymers include one or more hydroxy, methyl or methoxy groups. Particular examples of synthetic polymers include optionally substituted straight or branched chain poly(ethyleneglycol), poly (propyleneglycol) poly(vinyl alcohol) or derivatives thereof, especially optionally substituted poly(ethyleneglycol) such as methoxypoly(ethyleneglycol) or derivatives thereof. Particular naturally occurring polymers include lactose, amylose, dextran, glycogen or derivatives thereof. "Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50,000 Da, preferably from 5000 Da to 40,000 Da and more preferably from 25,000 Da to 40,000 Da. The polymer size may in particular be selected on the basis of the intended use of the product. Thus, for example, where the product is intended to leave the circulation and penetrate tissue, for example for use in the treatment of an inflammation, it may be advantageous to use a small molecular weight polymer, for example with a molecular weight of around 5000 Da. For applications where the product remains in the circulation, it may be advantageous to use a higher molecular weight polymer, for example having a molecular weight in the range from 25,000 Da to 40,000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 25,000 Da to about 40,000 Da.

Each polymer molecule attached to the modified antibody fragment may be covalently linked to the sulfur atom of a cysteine residue located in the fragment. The covalent linkage will generally be a disulfide bond or, in particular, a sulfur-carbon bond.

Where desired, the antibody fragment may have one or more effector or reporter molecules attached to it. The effector or reporter molecules may be attached to the antibody fragment through any available amino acid side-chain or terminal amino acid functional group located in the fragment, for example any free amino, imino, hydroxyl or carboxyl group. One or more effector or reporter molecules may be attached to an amino acid at or towards the C-terminal end of the heavy chain and/or the light chain of the antibody.

An activated polymer may be used as the starting material in the preparation of polymer-modified antibody fragments as described above. The activated polymer may be any polymer containing a thiol reactive group such as an α-halocarboxylic acid or ester, e.g., iodoacetamide, an imide, e.g., maleimide, a vinyl sulfone or a disulfide. Such starting materials may be obtained commercially (for example from Shearwater Polymers, Inc., Huntsville, Ala., USA) or may be prepared from commercially available starting materials using conventional chemical procedures.

Where it is desired to obtain an antibody fragment linked to an effector or reporter molecule, this may be prepared by standard chemical or recombinant DNA procedures in which the antibody fragment is linked either directly or via a coupling agent to the effector or reporter molecule either before or after reaction with the activated polymer as appropriate. Particular chemical procedures include, for example, those described in WO 93/62331 and WO 92/22583. Alternatively, where the effector or reporter molecule is a protein or polypeptide the linkage may be achieved using recombinant DNA procedures, for example as described in WO 86/01533 and EP-A-0392745.

Figure 2:
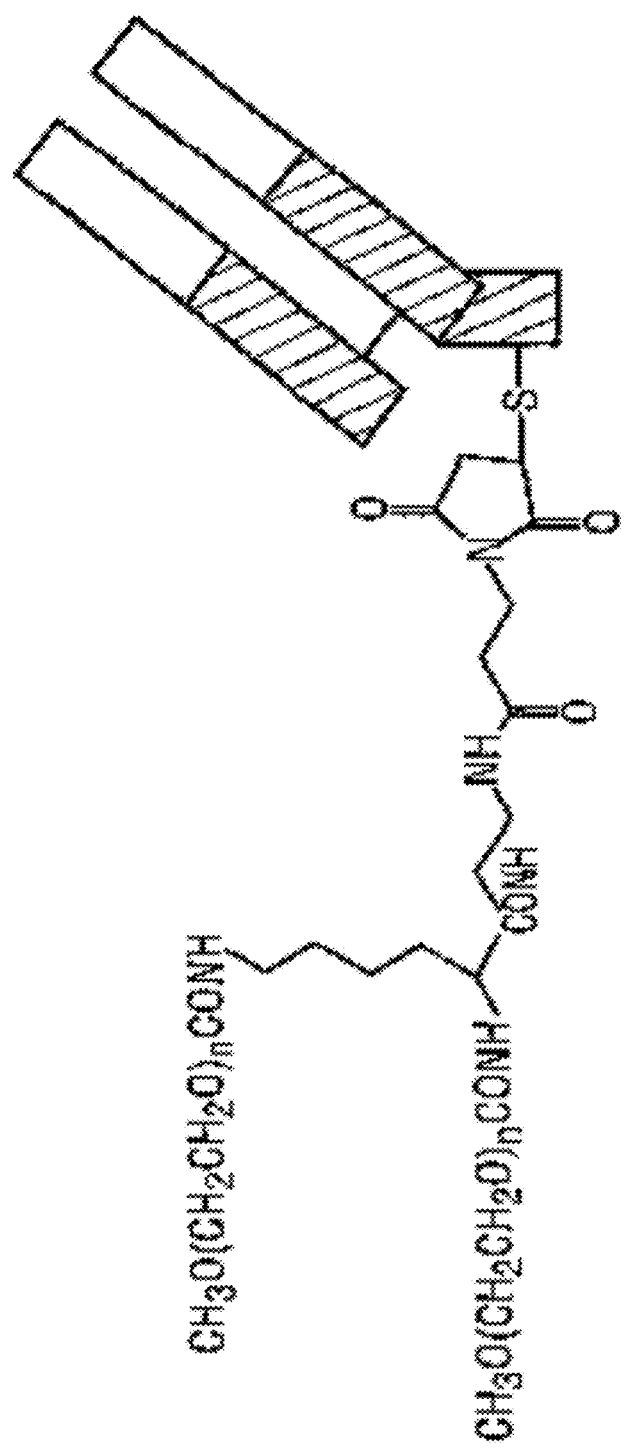
FIG. 2 shows the structure of a compound comprising a modified Fab' fragment covalently linked via a cysteine residue to a lysyl-maleimide linker, wherein each amino group on the lysyl residue has covalently attached to it a methoxy PEG residue, wherein n is between about 420 to 450.
Figure 3:
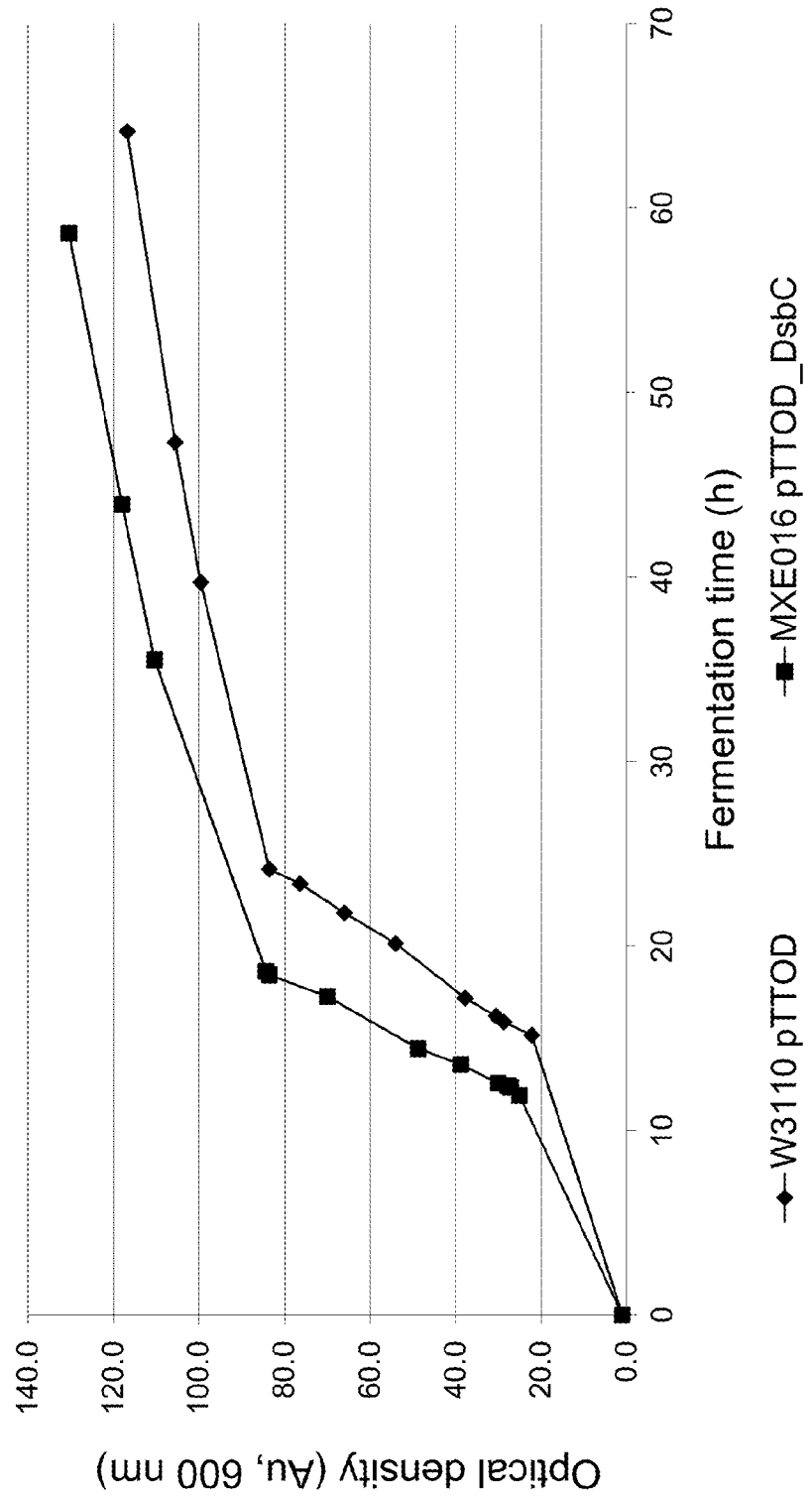
FIG. 3 shows the growth profile of anti-CD154 Fab'-expressing strain W3110 and the growth profile of anti-CD154 Fab' and recombinant DsbC-expressing strain MXE016 (W3110 ΔTsp, spr C94A). It can be seen that the MXE016 strain expressing recombinant DsbC exhibits improved growth profile and growth rate in the initial batch phase compared to the W3110 strain.
Figure 4:
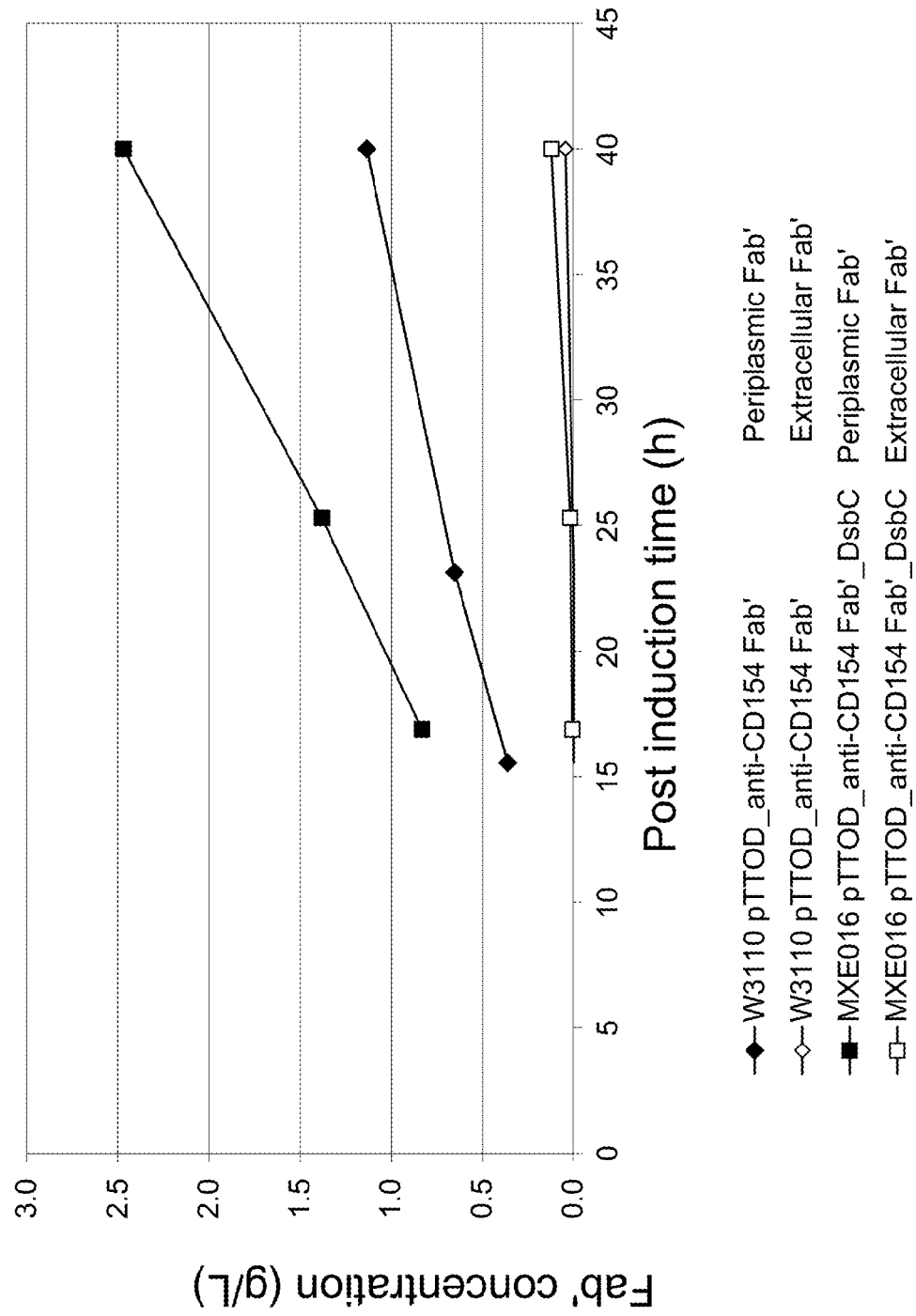
FIG. 4 shows total Fab' yield (g/L) from the periplasm (closed symbols) and supernatant (open symbols) from the MXE016 strain expressing recombinant DsbC compared to control strain W3110. The DsbC-expressing strain shows higher periplasmic Fab' expression compared to W3110. Further, the MXE016 strain expressing DsbC shows equivalent extracellular Fab' levels compared to strain W3110.

Preferably, the modified Fab fragment provided by the method of the present invention is PEGylated (i.e., has PEG (poly(ethyleneglycol)) covalently attached thereto) according to the method disclosed in EP-A-0948544. Preferably the antibody is a PEGylated modified Fab fragment as shown in FIG. 2. As shown in FIG. 2, the modified Fab fragment has attached to one of the cysteine residues at the C-terminal end of the modified hinge region of the heavy chain a lysyl-maleimide-derived group wherein each of the two amino groups of the lysyl residue has covalently linked to it a methoxypoly(ethyleneglycol) residue having a molecular weight of about 20,000 Da, such that the total average molecular weight of the methoxypoly(ethyleneglycol) residues is about 40,000 Da; more preferably the lysyl-maleimide-derived group is [1-[[[2-[[3-(2,5-dioxo-1-pyrrolidinyl)-1-oxopropyl]amino]ethyl]amino]-carbonyl]-1,5-pentanediyl]bis(iminocarbonyl). A lysine residue is covalently linked to the maleimide group. To each of the amine groups on the lysine residue is attached a methoxypoly(ethyleneglycol) polymer having a molecular weight of approximately 20,000 Da. The total molecular weight of the entire effector molecule is therefore approximately 40,000 Da.

Accordingly, the method according to the present invention preferably comprises attaching to one of the cysteine residues at the C-terminal end of the heavy chain a lysyl-maleimide group wherein each amino group of the lysyl residue has covalently linked to it a methoxypoly(ethyleneglycol) residue having a molecular weight of about 20,000 Da.

In one embodiment a physical property of a contaminating host protein is altered by the addition of an amino acid tag to the C-terminus or N-terminus. In a preferred embodiment the physical property that is altered is the isoelectric point and the amino acid tag is a poly-aspartic acid tag attached to the C-terminus. In one embodiment the *E. coli* proteins altered by the addition of said tag are dipeptide binding protein (DppA), maltose binding protein (MBP), thioredoxin and phosphate binding protein (PhoS/PstS). In one specific embodiment the pI of the *E. coli* phosphate binding protein (PhoS/PstS) is reduced from 7.2 to 5.1 by the addition of a poly-aspartic acid tag (polyD) containing 6 aspartic acid residues to the C-terminus.

Also preferred is the modification of specific residues of the contaminating *E. coli* protein to alter its physical properties, either alone or in combination with the addition of N- or C-terminal tags. Such changes can include insertions or deletions to alter the size of the protein or amino acid substitutions to alter pI or hydrophobicity. In one embodiment these residues are located on the surface of the protein. In a preferred embodiment surface residues of the PhoS protein are altered in order to reduce the pI of the protein. Preferably residues that have been implicated to be important in phosphate binding (U.S. Pat. No. 5,304,472) are avoided in order to maintain a functional PhoS protein.

EXAMPLES

Cell Lines

For all experiments the *E. coli* cell line W3110 was used as the parental wild-type cell line.
  Cell lines were created carrying the following mutations:
  a) a mutated Tsp gene;
  b) a mutated Tsp gene and carrying recombinant DsbC;
  c) a mutated Tsp gene and a mutated spr gene; and
  d) a mutated Tsp gene, a mutated spr gene and carrying recombinant DsbC.

Example 1 Generation of Cell Line Carrying Mutated Tsp Gene MXE001 (ΔTsp)

The MXE001 Strain was Generated as Follows:
  The Tsp cassette was moved as Sal I, Not I restriction fragments into similarly restricted pKO3 plasmids. The pKO3 plasmid uses the temperature-sensitive mutant of the pSC101 origin of replication (RepA) along with a chloramphenicol marker to force and select for chromosomal integration events. The sacB gene which encodes for levansucrase is lethal to *E. coli* grown on sucrose and hence (along with the chloramphenicol marker and pSC101 origin) is used to force and select for de-integration and plasmid curing events. This methodology had been described previously (Hamilton et al. 4617-22; Blomfield et al. 1447-57). The pKO3 system removes all selective markers from the host genome except for the inserted gene.
The Following Plasmid was Constructed:
  pMXE191 comprising the knockout mutated Tsp gene as shown in the SEQ ID NO: 28 comprising EcoR I and Ase I restriction markers.
  The plasmid was then transformed into electro-competent *E. coli* W3110 cells prepared using the method found in Miller and Nickoloff, which is incorporated herein by reference in its entirety (Miller and Nickoloff 105-13).
  Day 1: 40 μl of *E. coli* cells were mixed with (10 pg) 1 μl of pKO3 DNA in a chilled BioRad 0.2 cm electroporation cuvette before electroporation at 2500V, 25 μF and 200Ω. 1000 μl of 2×PY was added immediately, the cells recovered by shaking at 250 rpm in an incubator at 30° C. for 1 hour. Cells were serially 1/10 diluted in 2×PY before 100 μl aliquots were plated out onto 2×PY agar plates containing chloramphenicol at 20 μg/ml prewarmed at 30° C. and 43° C. Plates were incubated overnight at 30° C. and 43° C.
  Day 2: The number of colonies grown at 30° C. gave an estimate of the efficiency of electroporation, while colonies that survive growth at 43° C. represent potential integration events. Single colonies from the 43° C. plate were picked and resuspended in 10 ml of 2×PY. 100 μl of this was plated out onto 2×PY agar plates containing 5% (w/v) sucrose pre-warmed to 30° C. to generate single colonies. Plates were incubated overnight at 30° C.
  Day 3: Colonies here represent potential simultaneous de-integration and plasmid curing events. If the de-integration and curing events happened early on in the growth, then the bulk of the colony mass will be clonal. Single colonies were picked and replica plated onto 2×PY agar that contained either chloramphenicol at 20 μg/ml or 5% (w/v) sucrose. Plates were incubated overnight at 30° C.
  Day 4: Colonies that both grow on sucrose and die on chloramphenicol represent potential chromosomal replacement and plasmid curing events. These were picked and screened by PCR with a mutation-specific oligonucleotide. Colonies that generated a positive PCR band of the correct size were struck out to produce single colonies on 2×PY agar containing 5% (w/v) sucrose and the plates were incubated overnight at 30° C.
  Day 5: Single colonies of PCR-positive, chloramphenicol-sensitive and sucrose-resistant *E. coli* were used to make glycerol stocks and chemically competent cells and act as PCR templates for a PCR reaction with 5' and 3' flanking oligonucleotide primers to generate PCR product for direct DNA sequencing using Taq polymerase.
  Cell strain MXE001 was tested to confirm successful modification of genomic DNA carrying the mutated Tsp gene by PCR amplification of the region of the Tsp gene comprising a non-naturally occurring Ase I restriction site (SEQ ID NO: 28) using oligonucleotide primers. The amplified regions of the DNA were then analyzed by gel electrophoresis before and after incubation with Ase I restriction enzyme to confirm the presence of the non-naturally occurring Ase I restriction site in the mutated genes. This method was carried out as follows:
  The following oligos were used to amplify, using PCR, genomic DNA from prepared *E. coli* cell lysates from MXE001 and W3110:

```
6284 Tsp 3'
                                   (SEQ ID NO: 47)
5'-GCATCATAATTTTCTTTTTACCTC-3'

6283 Tsp 5'
                                   (SEQ ID NO: 48)
5'-GGGAAATGAACCTGAGCAAAACGC-3'
```

The lysates were prepared by heating a single colony of cells for 10 minutes at 95° C. in 20 μl of 1×PCR buffer. The mixture was allowed to cool to room temperature, then centrifuged at 13,200 rpm for 10 minutes. The supernatant was removed and labeled as "cell lysate".

Each strain was amplified using the Tsp oligonucleotide pair.

The DNA was amplified using a standard PCR procedure.

| | |
|---|---|
| 5 µl | Buffer x10 (Roche) |
| 1 µl | dNTP mix (Roche, 10 mM mix) |
| 1.5 µl | 5' oligo (5 pmol) |
| 1.5 µl | 3' oligo (5 pmol) |
| 2 µl | Cell lysate |
| 0.5 µl | Taq DNA polymerase (Roche 5 U/µl) |
| 38.5 µl | H$_2$O |

| PCR cycle | |
|---|---|
| 94° C. | 1 minute |
| 94° C. | 1 minute |
| 55° C. | 1 minute |
| | (repeated for 30 cycles) |
| 72° C. | 1 minute |
| 72° C. | 10 minutes |

Once the reactions were complete 25 µl was removed to a new microfuge tube for digestion with Ase I. To the 25 µl of PCR reaction 19 µl of H$_2$O, 5 µl of Buffer 3 (New England Biolabs®), and 1 µl of Ase I (New England Biolabs®) were added, mixed and incubated at 37° C. for 2 hours.

To the remaining PCR reaction 5 µl of loading buffer (×6) was added and 20 µl was loaded onto a 0.8% TAE 200 ml agarose gel (Invitrogen®) plus ethidium bromide (5 µl of 10 mg/ml stock) and run at 100 V for 1 hour. 10 µl of size marker (Perfect DNA marker 0.1-12 Kb, Novagen®) was loaded in the final lane.

Once the Ase I digestions were complete 10 µl of loading buffer (×6) was added and 20 µl was loaded onto a 0.8% TAE agarose gel (Invitrogen®) plus ethidium bromide (5 µl of 10 mg/ml stock) and run at 100 V for 1 hour. 10 µl of size marker (Perfect DNA marker 0.1-12 Kb, Novagen®) was loaded in the final lane. Both gels were visualized using a UV transluminator.

The genomic fragment amplified showed the correct sized band of 2.8 Kb for Tsp. Following digestion with Ase I this confirmed the presence of the introduced Ase I sites in the Tsp-deficient strain MXE001 but not in the W3110 control.

MXE001: genomic DNA was amplified using the Tsp primer set and the resulting DNA was digested with Ase I to produce 2.2 and 0.6 Kbps bands.

W3110 PCR amplified DNA was not digested by Ase I restriction enzyme.

Example 2—Generation of Cell Lines Carrying Mutated Spr Gene and Cell Lines Carrying a Mutated Tsp Gene and a Mutated Spr Gene The spr mutations were generated and selected for using a complementation assay.

The spr gene (SEQ ID NO: 23) was mutated using the Clontech® random mutagenisis diversity PCR kit which introduced 1 to 2 mutations per 1000 bp. The mutated spr PCR DNA was cloned into an inducible expression vector [pTTO CDP870] which expresses CDP870 Fab' (as described in WO 01/94585) along with the spr mutant. This ligation was then electro-transformed into an E. coli strain comprising a deletion variant of Tsp (ΔTsp) (designated MXE001) prepared using the method found in Miller et al. (Miller and Nickoloff 105-13). The following protocol was used: 40 µl of electro-competent MXE001, 2.5 µl of the ligation (100 pg of DNA) was added to a 0.2 cm electroporation cuvette, and electro-transformation was performed using as BioRad® Gene Pulser Xcell® with the following conditions: 2500 V, 25 µF and 200Ω. After the electro-transformation 1 ml of S.O.C. medium (Invitrogen® catalog: 18045-088) (pre-warmed to 37° C.) was added and the cells left to recover at 37° C. for 1 hour with gentle agitation.

The cells were plated onto hypotonic agar [5 g/L yeast extract, 2.5 g/L tryptone, 15 g/L agar (all Difco®)] and incubated at 40° C. Cells which formed colonies were re-plated onto HLB at 43° C. to confirm restoration of the ability to grow under low osmotic conditions at high temperature to the MXE001 strain. Plasmid DNA was prepared from the selected clones and sequenced to identify spr mutations.

Using this method eight single, one double and two multiple mutations in the spr protein were isolated which complemented the ΔTsp phenotype as follows:
1. V98E
2. D133A
3. V135D
4. V135G
5. G147C
6. S95F and Y115F
7. I70T
8. N31T, Q73R, R100G, and G140C
9. R62C, Q99P, and R144C
10. L108S
11. L136P.

The individual mutations 1 to 5 identified above and three catalytic triad mutations of spr (C94A, H145A, H157A) and W174R were used to generate new strains using either the wild-type W3110 E. coli strain (genotype: F-LAM-IN (rrnD-rrnE)1 rph1 (ATCC catalog no. 27325)) to create spr mutated strains or the MXE001 strain from Example 1 to make combined ΔTsp/mutant spr strains.

The following mutant E. coli cell strains were generated using a gene replacement vector system using the pKO3 homologous recombination/replacement plasmid (Link et al., supra) as described in Example 1 for the generation of MXE001.

TABLE 1

| Mutant E. coli Strain | Genotype | Spr Vectors |
|---|---|---|
| MXE001 | ΔTsp | — |
| MXE008 | ΔTsp, spr D133A | pMXE339, pK03 spr D133A (-SalI) |
| MXE009 | ΔTsp, spr H157A | pMXE345, pK03 spr H157A (-SalI) |
| MXE010 | spr G147C | pMXE338, pK03 spr G147C (-SalI) |
| MXE011 | spr C94A | pMXE343, pK03 spr C94A (-SalI) |
| MXE012 | spr H145A | pMXE344, pK03 spr H145A (-SalI) |
| MXE013 | spr W174R | pMXE346, pK03 spr W174R (-SalI) |
| MXE014 | ΔTsp, spr V135D | pMXE340, pK03 spr V135D (-SalI) |
| MXE015 | ΔTsp, spr V98E | pMXE342, pK03 spr V98E (-SalI) |
| MXE016 | ΔTsp, spr C94A | pMXE343, pK03 spr C94A (-SalI) |
| MXE017 | ΔTsp, spr H145A | pMXE344, pK03 spr H145A (-SalI) |
| MXE018 | ΔTsp, spr V135G | pMXE341, pK03 spr V135G (-SalI) |

The mutant spr integration cassettes were moved as Sal I, Not I restriction fragments into similarly restricted pKO3 plasmids.

For all experiments the *E. coli* cell line W3110 was used as the wild-type cell line and the *E. coli* cell line W3110 ΔTsp, spr C94A (MXE016).

Example 3—Generation of Plasmid for Anti-CD154 Fab' and DsbC Expression

A plasmid was constructed containing both the heavy and light chain sequences of an anti-CD154 Fab (SEQ ID NOs: 13 and 11, respectively) and the sequence encoding DsbC (SEQ ID NO: 27).

Plasmid pMXE351 (pTTOD_DsbC), an expression vector for the anti-CD154 Fab and DsbC (a periplasmic polypeptide), was constructed using conventional restriction cloning methodologies. The plasmid pMXE351 contained the following features: a strong tac promoter and lac operator sequence. As shown in FIG. 1, the plasmid contained a unique EcoRI restriction site after the coding region of the Fab' heavy chain, followed by a non-coding sequence and then a unique NdeI restriction site. The DsbC gene was PCR cloned using W3110 crude chromosomal DNA as a template. An EcoRI site was removed from the wild-type DsbC sequence by PCR overlap extension such that the PCR product encoded for a 5' EcoRI site followed by a strong ribosome binding site, followed by the native start codon, signal sequence and mature sequence of DsbC, terminating in a C-terminal His tag and finally a non-coding NdeI site. The EcoRI-NdeI PCR fragment was restricted and ligated into the expression vector such that all three polypeptides (Fab' light chain, Fab' heavy chain and DsbC) were encoded on a single polycistronic mRNA.

The Fab light chain and heavy chain genes and DsbC gene were transcribed as a single polycistronic message. DNA encoding the signal peptide from the *E. coli* OmpA protein was fused to the 5' end of both light and heavy chain gene sequences, which directed the translocation of the polypeptides to the *E. coli* periplasm. Transcription was terminated using a dual transcription terminator rrnB t1t2. The lacIq gene encoded the constitutively expressed Lac I repressor protein. This repressed transcription from the tac promoter until de-repression was induced by the presence of allolactose or IPTG. The origin of replication used was p15A, which maintained a low copy number. The plasmid contained a tetracycline resistance gene for antibiotic selection.

Example 4—Expression of Anti-CD154 Fab' and DsbC in *E. coli* W3110 and MXE016 (*E. coli* W3110 ΔTsp, spr C94A)

Expression of Anti-CD154 Fab' and DsbC in *E. coli* W3110 ΔTsp, spr C94A

The *E. coli* W3110 ΔTsp, spr C94A cell strain (MXE016) was transformed with the plasmid pMXE351 generated in Example 3. The transformation of the strains was carried out using the method found in Chung, C. T. et al. (Chung, Niemela, and Miller 2172-75).

Expression of Anti-CD154 Fab' in *E. coli* W3110

The *E. coli* W3110 cell strain was transformed with plasmid pTTOD, an expression vector for the anti-CD154 Fab', which was constructed using conventional restriction cloning methodologies. The plasmid pTTOD contained the following features: a strong tac promoter and lac operator sequence. The Fab light and heavy chain genes were transcribed as a single dicistronic message. DNA encoding the signal peptide from the *E. coli* OmpA protein was fused to the 5' end of both light and heavy chain gene sequences, which directed the translocation of the polypeptides to the *E. coli* periplasm. Transcription was terminated using a dual transcription terminator rrnB t1t2. The lacIq gene encoded the constitutively expressed Lac I repressor protein. This repressed transcription from the tac promoter until de-repression was induced by the presence of allolactose or IPTG. The origin of replication used was p15A, which maintained a low copy number. The plasmid contained a tetracycline resistance gene for antibiotic selection. The transformation of the strains was carried out using the method found in Chung, C. T. et al. (Chung, Niemela, and Miller 2172-75).

Example 5—Growth of Mutated *E. coli* Strains and Expression of Anti-CD154 Fab' in Mutated *E. coli* Strains Using High Density Fermentations The strains produced in Example 4 were tested in fermentation experiments comparing growth and expression of an anti-CD154 Fab'.

Growth Medium, Inoculum and Fermentation Steps.

The fermentation process is initiated by preparing an inoculum from a vial of the cell bank and amplifying through several pre-culture stages (flask and reactors) before seeding of the production fermenter. In the production fermenter, the cells are grown in defined media to high density in batch and fed-batch mode. When the desired cell density is reached expression of the Fab' is induced by the addition of IPTG. The Fab' expression is targeted to the *E. coli* periplasmic space, where Fab' accumulates throughout the course of the induction phase. A carbon source feed is applied during the induction phase to control expression and cell growth. Temperature, dissolved oxygen ($pO_2$) and pH are controlled to maintain the culture within optimal culture conditions.

Measurement of Biomass Concentration and Growth Rate.

Biomass concentration was determined by measuring the optical density of cultures at 600 nm.

Periplasmic Extraction.

Cells were collected from culture samples by centrifugation. The supernatant fraction was retained (at −20° C.) for further analysis. The cell pellet fraction was resuspended to the original culture volume in extraction buffer (100 mM Tris-HCl, 10 mM EDTA; pH 7.4). Following incubation at 60° C. for approximately 10 to 16 hours the extract was clarified by centrifugation and the supernatant fraction used fresh or retained (at −20° C.) for analysis.

Fab' Quantification.

Fab' concentrations in periplasmic extracts and culture supernatants were determined by using Protein G HPLC. A HiTrap® Protein-G HP 1 ml column (GE Healthcare® or equivalent) was loaded with analyte (approximately neutral pH, 30° C., 0.2 μm filtered) at 2 ml/min, the column was washed with 20 mM phosphate, 50 mM NaCl, pH 7.4 and then Fab' was eluted using an injection of 50 mM glycine/HCl, pH 2.7. Eluted Fab' was measured by A280 on an Agilent® 1100 or 1200 HPLC system and quantified by reference to a standard curve of a purified Fab' protein of known concentration.

Example 6—Level of Light Chain Fragments in Fermentation Extractions of Mutated *E. coli* Strains The fermentations presented in Example 2 were tested for light chain fragment level of anti-CD154 Fab' in periplasmic extractions.

Light Chain Fragment Quantification.

Quantitative estimation of the level of Fab' and Fab' proteolytic fragments was achieved by high-temperature reversed phase HPLC. Separation is performed on a Poroshell® 300SB-C8 reversed phase column (Agilent Technologies®, Product No. 660750-906) at a temperature of 80° C. The equilibration solvent is HPLC water, 0.1% (v/v) TFA, and the elution solvent is 80:20 (v/v) 1-propanol:acetonitrile, 0.03% (v/v) TFA. Separation is performed at a flow rate of 2.0 mL/min, by means of a linear gradient of 16-38% solvent B in 4.4 min. Detection was by UV absorbance at 214 nm. Data were processed by manual integration, and the quantity of Fab proteolytic fragments expressed as % peak area relative to the intact Fab peak.

The present invention also provides a therapeutic or diagnostic composition comprising the antibody produced by the method of the present invention in combination with a pharmaceutically acceptable excipient, diluent or carrier.

The present invention also provides a process for preparation of a therapeutic or diagnostic composition comprising admixing the antibody produced by the method of the present invention together with a pharmaceutically acceptable excipient, diluent or carrier.

While this invention has been particularly shown and described with reference to preferred embodiments, it will be understood to those skilled in the art that various changes in form and detail may be made without departing from the scope of the invention as defined by the appending claims.

REFERENCE LIST

Aramini, J. M., et al. "Solution NMR structure of the NlpC/P60 domain of lipoprotein Spr from *Escherichia coli*: structural evidence for a novel cysteine peptidase catalytic triad." Biochemistry. 47.37 (2008): 9715-17.

Bachmann, B. J. "Pedigrees of some mutant strains of *Escherichia coli* K-12." Bacteriol. Rev. 36.4 (1972): 525-57.

Backlund, E., et al. "Fedbatch design for periplasmic product retention in *Escherichia coli*." J. Biotechnol. 135.4 (2008): 358-65.

Blomfield, I. C., et al. "Allelic exchange in *Escherichia coli* using the *Bacillus subtilis* sacB gene and a temperature-sensitive pSC101 replicon." Mol. Microbiol. 5.6 (1991): 1447-57.

Chung, C. T., S. L. Niemela, and R. H. Miller. "One-step preparation of competent *Escherichia coli*: transformation and storage of bacterial cells in the same solution." Proc. Natl. Acad. Sci. U.S.A. 86.7 (1989): 2172-75.

Hamilton, C. M., et al. "New method for generating deletions and gene replacements in *Escherichia coli*." J. Bacteriol. 171.9 (1989): 4617-22.

Hara, H., et al. "Overproduction of penicillin-binding protein 7 suppresses thermosensitive growth defect at low osmolarity due to an spr mutation of *Escherichia coli*." Microb. Drug Resist. 2.1 (1996): 63-72.

Hara, H., et al. "Cloning, mapping, and characterization of the *Escherichia coli* prc gene, which is involved in C-terminal processing of penicillin-binding protein 3." J. Bacteriol. 173.15 (1991): 4799-813.

Holliger, P. and P. J. Hudson. "Engineered antibody fragments and the rise of single domains." Nat. Biotechnol. 23.9 (2005): 1126-36.

Humphreys, D. P., et al. "Formation of dimeric Fabs in *Escherichia coli*: effect of hinge size and isotype, presence of interchain disulphide bond, Fab' expression levels, tail piece sequences and growth conditions." J. Immunol. Methods. 209.2 (1997): 193-202.

Keiler, K. C. and R. T. Sauer. "Identification of active site residues of the Tsp protease." J. Biol. Chem. 270.48 (1995): 28864-68.

Link, A. J., D. Phillips, and G. M. Church. "Methods for generating precise deletions and insertions in the genome of wild-type *Escherichia coli*: application to open reading frame characterization." J. Bacteriol. 179.20 (1997): 6228-37.

Makrides, S. C. "Strategies for achieving high-level expression of genes in *Escherichia coli*." Microbiol. Rev. 60.3 (1996): 512-38.

Miller, E. M. and J. A. Nickoloff. "*Escherichia coli* electrotransformation." Methods Mol. Biol. 47:105-13. (1995): 105-13.

Missiakas, D., C. Georgopoulos, and S. Raina. "The *Escherichia coli* dsbC (xprA) gene encodes a periplasmic protein involved in disulfide bond formation." EMBO J. 13.8 (1994): 2013-20.

Nagasawa, H., et al. "Determination of the cleavage site involved in C-terminal processing of penicillin-binding protein 3 of *Escherichia coli*." J. Bacteriol. 171.11 (1989): 5890-93.

Shevchik, V. E., G. Condemine, and J. Robert-Baudouy. "Characterization of DsbC, a periplasmic protein of *Erwinia chrysanthemi* and *Escherichia coli* with disulfide isomerase activity." EMBO J. 13.8 (1994): 2007-12.

Silber, K. R., K. C. Keiler, and R. T. Sauer. "Tsp: a tail-specific protease that selectively degrades proteins with nonpolar C termini." Proc. Natl. Acad. Sci. U.S.A. 89.1 (1992): 295-99.

Silber, K. R. and R. T. Sauer. "Deletion of the prc (tsp) gene provides evidence for additional tail-specific proteolytic activity in *Escherichia coli* K-12." Mol. Gen. Genet. 242.2 (1994): 237-40.

We claim:

1. A recombinant gram-negative bacterial cell comprising the following genetic modifications:
   (a) an expression vector comprising a recombinant polynucleotide encoding a DsbC protein;
   (b) a polynucleotide encoding a periplasmic Pre protease (Tsp), said polynucleotide comprising nucleotides 7 to 2048 of SEQ ID NO: 25 or comprising SEQ ID NO: 28;
   (c) one or more polynucleotides encoding an antibody or an antigen binding fragment thereof specifically binding to CD154; and
   (d) optionally, a polynucleotide encoding a mutant extragenic suppressor (spr) protein,
   wherein the cell is isogenic to a wild-type bacterial cell except for the genetic modifications (a) to (c) and when present, (d).

2. The gram-negative bacterial cell according to claim 1, wherein the expression vector comprises a polynucleotide having the sequence given in SEQ ID NO: 45 or SEQ ID NO: 51.

3. The gram-negative bacterial cell according to claim 1, wherein the antibody or antigen binding fragment thereof comprises a heavy chain variable domain comprising three CDRs having the sequence given in SEQ ID NO: 1 for CDRH1, SEQ ID NO: 2, for CDRH2 and SEQ ID NO: 3 for CDRH3 and a variable domain light chain comprising three CDRs having the sequence given in SEQ ID NO: 4 for CDRL1, SEQ ID NO: 5 for CDRL2 and SEQ ID NO: 6 for CDRL3.

4. The gram-negative bacterial cell according to claim 3, wherein the one or more polynucleotides encode an antibody comprising the light chain variable region sequence given in SEQ ID NO: 8 and the heavy chain variable region given in SEQ ID NO: 10.

5. The gram-negative bacterial cell according to claim 1, wherein the antibody is a Fab or Fab' fragment.

6. The gram-negative bacterial cell according to claim 5, wherein the Fab or Fab' fragment comprises a light chain having the sequence given in SEQ ID NO: 12 and a heavy chain having the sequence given in SEQ ID NO: 14 or 16.

7. The gram-negative bacterial cell according to claim 1, wherein the gram-negative bacterial cell comprises a first expression vector comprising the recombinant polynucleotide encoding DsbC and a second expression vector comprising one or more polynucleotides encoding the antibody or an antigen binding fragment thereof specifically binding to CD154.

8. The gram-negative bacterial cell according to claim 1, wherein the expression vector comprising the recombinant polynucleotide encoding DsbC additionally comprises one or more polynucleotides encoding an antibody or an antigen binding fragment thereof specifically binding to CD154.

9. The gram-negative bacterial cell according to claim 1, wherein the cell comprises a recombinant polynucleotide encoding the mutant spr protein.

10. The gram-negative bacterial cell according to claim 1, wherein the cell is E. coli.

11. The gram-negative bacterial cell according to claim 1, wherein the cell comprises an expression vector comprising the recombinant polynucleotide encoding DsbC and a dicistronic message for producing the antibody or antigen binding fragment thereof specifically binding to CD154, in which the upstream cistron contains DNA coding for the light chain of the antibody and the downstream cistron contains DNA coding for the corresponding heavy chain, characterised in that the dicistronic message comprises a sequence selected from IGS1 (SEQ ID NO: 33), IGS2 (SEQ ID NO: 34), IGS3 (SEQ ID NO: 35) and IGS4 (SEQ ID NO: 36).

12. A method for producing an antibody or an antigen binding fragment thereof specifically binding to CD154 comprising:
  (a) culturing a recombinant gram-negative bacterial cell according to claim 1 in a culture medium under conditions effective to express the antibody or the antigen binding fragment thereof specifically binding to CD154 and the recombinant polynucleotide encoding DsbC; and
  (b) recovering the antibody or an antigen binding fragment thereof specifically binding to CD154 from the periplasm of the recombinant gram-negative bacterial cell and/or the culture medium.

13. The method according to claim 12, wherein the method further comprises a step of attaching an effector molecule to an amino acid at or towards the C-terminal end of the heavy chain and/or the light chain of the antibody.

14. The method according to claim 12, wherein the effector molecule comprises poly(ethyleneglycol) or methoxypoly(ethyleneglycol).

15. The method according to claim 14, wherein the method comprises attaching to one of the cysteine residues at the C-terminal end of the heavy chain a lysyl-maleimide group wherein each amino group of the lysyl residue has covalently linked to it a methoxypoly(ethyleneglycol) residue having a molecular weight of about 20,000 Da.

16. The gram-negative bacterial cell according to claim 1, said gram-negative bacterial cell comprising nucleotides 7 to 2048 of SEQ ID NO: 25.

17. The gram-negative bacterial cell according to claim 1, said gram-negative bacterial cell comprising SEQ ID NO: 28.

18. The gram-negative bacterial cell according to claim 9, wherein the mutant spr protein comprises an amino acid mutation selected from C94A, D133A, H145A and H157A.

19. The gram-negative bacterial cell according to claim 18, wherein the mutant spr protein comprises the amino acid mutation C94A.

20. The gram-negative bacterial cell according to claim 1, said gram-negative bacterial cell comprising SEQ ID NO: 28 and a mutant spr protein comprising an amino acid mutation selected from C94A, D133A, H145A and H157A.

21. The gram-negative bacterial cell according to claim 1, said gram-negative bacterial cell comprising nucleotides 7 to 2048 of SEQ ID NO: 25 and a mutant spr protein comprising an amino acid mutation selected from C94A, D133A, H145A and H157A.

22. The gram-negative bacterial cell according to claim 20, wherein the mutant spr protein comprises the amino acid mutation C94A.

23. The gram-negative bacterial cell according to claim 21, wherein the mutant spr protein comprises the amino acid mutation C94A.

24. The method according to claim 12, said gram-negative bacterial cell comprising SEQ ID NO: 28 and a mutant spr protein comprising an amino acid mutation selected from C94A, D133A, H145A and H157A.

25. The method according to claim 12, said gram-negative bacterial cell comprising nucleotides 7 to 2048 of SEQ ID NO: 25 and a mutant spr protein comprising an amino acid mutation selected from C94A, D133A, H145A and H157A.

26. The method according to claim 24, wherein the mutant spr protein comprises the amino acid mutation C94A.

27. The method according to claim 25, wherein the mutant spr protein comprises the amino acid mutation C94A.

* * * * *

UNITED STATES PATENT AND TRADEMARK OFFICE
CERTIFICATE OF CORRECTION

PATENT NO. : 9,957,328 B2
APPLICATION NO. : 15/667649
DATED : May 1, 2018
INVENTOR(S) : Mark Ellis and David Paul Humphreys It is certified that error appears in the above-identified patent and that said Letters Patent is hereby corrected as shown below:

In the Specification

Column 15,
Line 15, "acid 5430" should read --acid S430--.
Line 18, "acids 5430" should read --acids S430--.
Line 19, "acids 5430" should read --acids S430--.
Line 21, "acids 5430" should read --acids S430--.
Line 23, "residues 5430" should read --residues S430--.

In the Claims

Column 129,
Line 42, Claim 1: "Pre protease" should read --Prc protease--.

Signed and Sealed this
Twenty-second Day of January, 2019

Andrei Iancu
*Director of the United States Patent and Trademark Office*

SEQUENCE LISTING

```
<160> NUMBER OF SEQ ID NOS: 58

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: 342 CDR-H1

<400> SEQUENCE: 1

Gly Phe Ser Ser Thr Asn Tyr His Val His
```

```
<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: 342 CDR-H2

<400> SEQUENCE: 2

Val Ile Trp Gly Asp Gly Asp Thr Ser Tyr Asn Ser Val Leu Lys Ser
1               5                   10                  15

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: 342 CDR-H3

<400> SEQUENCE: 3

Gln Leu Thr His Tyr Tyr Val Leu Ala Ala
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: 342 CDR-L1

<400> SEQUENCE: 4

Arg Ala Ser Glu Asp Leu Tyr Tyr Asn Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: 342 CDR-L2

<400> SEQUENCE: 5

Asp Thr Tyr Arg Leu Ala Asp
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: 342 CDR-L3

<400> SEQUENCE: 6

Gln Gln Tyr Tyr Lys Phe Pro Phe Thr
1               5

<210> SEQ ID NO 7
<211> LENGTH: 384
<212> TYPE: DNA
<213> ORGANISM: Artificial Sequence
<220> FEATURE:
<223> OTHER INFORMATION: Description of Artificial Sequence: 342
      variable light chain (gL4)
<220> FEATURE:
<221> NAME/KEY: sig_peptide
<222> LOCATION: (1)..(63)
<220> FEATURE:
```

```
<221> NAME/KEY: CDS
<222> LOCATION: (64)..(384)

<400> SEQUENCE: 7
atgaaaaaga cagctatcgc aattgcagtg gccttggctg gtttcgctac cgtagcgcaa      60 gct gat atc cag atg acc cag agt cca agc agt ctc tcc gcc agc gta     108
    Asp Ile Gln Met Thr Gln Ser Pro Ser Ser Leu Ser Ala Ser Val
    1               5                  10                  15 ggc gat cgt gtg act att acc tgt cgt gcc agt gag gac ctc tat tac     156
Gly Asp Arg Val Thr Ile Thr Cys Arg Ala Ser Glu Asp Leu Tyr Tyr
                20                  25                  30 aac ctg gcc tgg tat cag cgt aaa ccg ggc aaa gcc ccg aag ctg ctc     204
Asn Leu Ala Trp Tyr Gln Arg Lys Pro Gly Lys Ala Pro Lys Leu Leu
            35                  40                  45 atc tat gat acg tac cgc ctg gct gac ggt gtg cca agc cgt ttc agt     252
Ile Tyr Asp Thr Tyr Arg Leu Ala Asp Gly Val Pro Ser Arg Phe Ser
        50                  55                  60 ggc agt ggc agc ggt act gac tat acc ctc aca att tcg tct ctc cag     300
Gly Ser Gly Ser Gly Thr Asp Tyr Thr Leu Thr Ile Ser Ser Leu Gln
65                  70                  75 ccg gaa gat ttc gcc tct tac tat tgt cag caa tat tac aag ttc cct     348
Pro Glu Asp Phe Ala Ser Tyr Tyr Cys Gln Gln Tyr Tyr Lys Phe Pro
80                  85                  90                  95 ttc acc ttc ggt cag ggc act aaa gta gaa atc aaa                     384
Phe Thr Phe Gly Gln Gly Thr Lys Val Glu Ile Lys
                100                 105

<210> SEQ ID NO 8
<211> LENGTH: 107
<212> TYPE: PRT
<213> ORGANISM: Artificial Sequence
<220> FEATURE:
<223> OTHER INFORMATION: Synthetic Construct

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Leu Tyr Tyr Asn
            20                  25                  30

Leu Ala Trp Tyr Gln Arg Lys Pro Gly Lys Ala Pro Lys Leu Leu Ile
y       35                  40                  45

Tyr Asp Thr Tyr Arg Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Ser Tyr Tyr Cys Gln Gln Tyr Tyr Lys Phe Pro Phe
                85                  90                  95

Thr Phe Gly Gln Gly Thr Lys Val Glu Ile Lys
            100                 105

<210> SEQ ID NO 9
<211> LENGTH: 351
<212> TYPE: DNA
<213> ORGANISM: Artificial Sequence
<220> FEATURE:
<223> OTHER INFORMATION: Description of Artificial Sequence: 342
      variable heavy chain (gH1)
<220> FEATURE:
<221> NAME/KEY: CDS
<222> LOCATION: (1)..(351)

<400> SEQUENCE: 9
```

```
gag gtg cag ctg gtc gag tct gga ggc ggg ctt gtc cag cct ggt ggg    48
Glu Val Gln Leu Val Glu Ser Gly Gly Gly Leu Val Gln Pro Gly Gly
1               5                   10                  15 agc ctg cgt ctc tct tgt gca gtg agc ggc ttc agc tct acc aat tac    96
Ser Leu Arg Leu Ser Cys Ala Val Ser Gly Phe Ser Ser Thr Asn Tyr
            20                  25                  30 cat gtg cac tgg gtg cgt cag gca cct ggg aag ggc ctg gag tgg atg   144
His Val His Trp Val Arg Gln Ala Pro Gly Lys Gly Leu Glu Trp Met
        35                  40                  45 ggt gtt att tgg ggc gac ggc gat aca tcc tac aac tcc gtc ctg aag   192
Gly Val Ile Trp Gly Asp Gly Asp Thr Ser Tyr Asn Ser Val Leu Lys
50                  55                  60 agc cgt ttc acc att tcc cgt gac acc tca aag aat acc gtt tac ctc   240
Ser Arg Phe Thr Ile Ser Arg Asp Thr Ser Lys Asn Thr Val Tyr Leu
65                  70                  75                  80 cag atg aac tct ctc cgc gca gag gac aca gca gtc tat tac tgt gca   288
Gln Met Asn Ser Leu Arg Ala Glu Asp Thr Ala Val Tyr Tyr Cys Ala
                85                  90                  95 cgt caa ctg acc cac tat tac gtt ttg gca gcc tgg ggt caa ggg act   336
Arg Gln Leu Thr His Tyr Tyr Val Leu Ala Ala Trp Gly Gln Gly Thr
            100                 105                 110 ctg gtc aca gtc tcg                                               351
Leu Val Thr Val Ser
        115

<210> SEQ ID NO 10
<211> LENGTH: 117
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Ser Thr Asn Tyr
            20                  25                  30

His Val His Trp Val Arg Gln Ala Pro Gly Lys Gly Leu Glu Trp Met
y       35                  40                  45

Gly Val Ile Trp Gly Asp Gly Asp Thr Ser Tyr Asn Ser Val Leu Lys
50                  55                  60

Ser Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gln Leu Thr His Tyr Tyr Val Leu Ala Ala Trp Gly Gln Gly Thr
            100                 105                 110

Leu Val Thr Val Ser
        115

<210> SEQ ID NO 11
<211> LENGTH: 705
<212> TYPE: DNA
<213> ORGANISM: Artificial Sequence
<220> FEATURE:
<223> OTHER INFORMATION: Description of Artificial Sequence: 342 gL4
      (V+C)
<220> FEATURE:
<221> NAME/KEY: CDS
<222> LOCATION: (64)..(705)
```

<400> SEQUENCE: 11

```
atgaaaaaga cagctatcgc aattgcagtg gccttggctg gtttcgctac cgtagcgcaa         60
```

| | | | | | | | | | | | | | | | | |
|---|---|---|---|---|---|---|---|---|---|---|---|---|---|---|---|---|
| gct | gat | atc | cag | atg | acc | cag | agt | cca | agc | agt | ctc | tcc | gcc | agc | gta | 108 |
|  | Asp | Ile | Gln | Met | Thr | Gln | Ser | Pro | Ser | Ser | Leu | Ser | Ala | Ser | Val |  |
|  | 1 |  |  | 5 |  |  |  |  | 10 |  |  |  |  | 15 |  |  |
| ggc | gat | cgt | gtg | act | att | acc | tgt | cgt | gcc | agt | gag | gac | ctc | tat | tac | 156 |
| Gly | Asp | Arg | Val | Thr | Ile | Thr | Cys | Arg | Ala | Ser | Glu | Asp | Leu | Tyr | Tyr |  |
|  |  |  | 20 |  |  |  |  | 25 |  |  |  |  | 30 |  |  |  |
| aac | ctg | gcc | tgg | tat | cag | cgt | aaa | ccg | ggc | aaa | gcc | ccg | aag | ctg | ctc | 204 |
| Asn | Leu | Ala | Trp | Tyr | Gln | Arg | Lys | Pro | Gly | Lys | Ala | Pro | Lys | Leu | Leu |  |
|  |  |  | 35 |  |  |  | 40 |  |  |  |  | 45 |  |  |  |  |
| atc | tat | gat | acg | tac | cgc | ctg | gct | gac | ggt | gtg | cca | agc | cgt | ttc | agt | 252 |
| Ile | Tyr | Asp | Thr | Tyr | Arg | Leu | Ala | Asp | Gly | Val | Pro | Ser | Arg | Phe | Ser |  |
|  | 50 |  |  |  |  | 55 |  |  |  |  | 60 |  |  |  |  |  |
| ggc | agt | ggc | agc | ggt | act | gac | tat | acc | ctc | aca | att | tcg | tct | ctc | cag | 300 |
| Gly | Ser | Gly | Ser | Gly | Thr | Asp | Tyr | Thr | Leu | Thr | Ile | Ser | Ser | Leu | Gln |  |
|  | 65 |  |  |  |  | 70 |  |  |  |  | 75 |  |  |  |  |  |
| ccg | gaa | gat | ttc | gcc | tct | tac | tat | tgt | cag | caa | tat | tac | aag | ttc | cct | 348 |
| Pro | Glu | Asp | Phe | Ala | Ser | Tyr | Tyr | Cys | Gln | Gln | Tyr | Tyr | Lys | Phe | Pro |  |
| 80 |  |  |  |  | 85 |  |  |  |  | 90 |  |  |  |  | 95 |  |
| ttc | acc | ttc | ggt | cag | ggc | act | aaa | gta | gaa | atc | aaa | cgt | acg | gta | gcg | 396 |
| Phe | Thr | Phe | Gly | Gln | Gly | Thr | Lys | Val | Glu | Ile | Lys | Arg | Thr | Val | Ala |  |
|  |  |  |  | 100 |  |  |  |  | 105 |  |  |  |  | 110 |  |  |
| gcc | cca | tct | gtc | ttc | atc | ttc | ccg | cca | tct | gat | gag | cag | ttg | aaa | tct | 444 |
| Ala | Pro | Ser | Val | Phe | Ile | Phe | Pro | Pro | Ser | Asp | Glu | Gln | Leu | Lys | Ser |  |
|  |  | 115 |  |  |  |  | 120 |  |  |  |  | 125 |  |  |  |  |
| gga | act | gcc | tct | gtt | gtg | tgc | ctg | ctg | aat | aac | ttc | tat | ccc | aga | gag | 492 |
| Gly | Thr | Ala | Ser | Val | Val | Cys | Leu | Leu | Asn | Asn | Phe | Tyr | Pro | Arg | Glu |  |
|  |  | 130 |  |  |  |  | 135 |  |  |  |  | 140 |  |  |  |  |
| gcc | aaa | gta | cag | tgg | aag | gtg | gat | aac | gcc | ctc | caa | tcg | ggt | aac | tcc | 540 |
| Ala | Lys | Val | Gln | Trp | Lys | Val | Asp | Asn | Ala | Leu | Gln | Ser | Gly | Asn | Ser |  |
|  | 145 |  |  |  |  | 150 |  |  |  |  | 155 |  |  |  |  |  |
| cag | gag | agt | gtc | aca | gag | cag | gac | agc | aag | gac | agc | acc | tac | agc | ctc | 588 |
| Gln | Glu | Ser | Val | Thr | Glu | Gln | Asp | Ser | Lys | Asp | Ser | Thr | Tyr | Ser | Leu |  |
| 160 |  |  |  |  | 165 |  |  |  |  | 170 |  |  |  |  | 175 |  |
| agc | agc | acc | ctg | acg | ctg | agc | aaa | gca | gac | tac | gag | aaa | cac | aaa | gtc | 636 |
| Ser | Ser | Thr | Leu | Thr | Leu | Ser | Lys | Ala | Asp | Tyr | Glu | Lys | His | Lys | Val |  |
|  |  |  |  | 180 |  |  |  |  | 185 |  |  |  |  | 190 |  |  |
| tac | gcc | tgc | gaa | gtc | acc | cat | cag | ggc | ctg | agc | tca | cca | gta | aca | aaa | 684 |
| Tyr | Ala | Cys | Glu | Val | Thr | His | Gln | Gly | Leu | Ser | Ser | Pro | Val | Thr | Lys |  |
|  |  | 195 |  |  |  |  | 200 |  |  |  |  | 205 |  |  |  |  |
| agt | ttt | aat | aga | ggg | gag | tgt |  |  |  |  |  |  |  |  |  | 705 |
| Ser | Phe | Asn | Arg | Gly | Glu | Cys |  |  |  |  |  |  |  |  |  |  |
|  |  | 210 |  |  |  |  |  |  |  |  |  |  |  |  |  |  |

```
<210> SEQ ID NO 12
<211> LENGTH: 214
<212> TYPE: PRT
<213> ORGANISM: Artificial Sequence
<220> FEATURE:
<223> OTHER INFORMATION: Synthetic Construct

<400> SEQUENCE: 12
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Leu Tyr Tyr Asn
            20                  25                  30

Leu Ala Trp Tyr Gln Arg Lys Pro Gly Lys Ala Pro Lys Leu Leu Ile
y       35                  40                  45

```
Tyr Asp Thr Tyr Arg Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Ser Tyr Tyr Cys Gln Gln Tyr Tyr Lys Phe Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
y           115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
y           195                 200                 205

Phe Asn Arg Gly Glu Cys
    210
```

<210> SEQ ID NO 13
<211> LENGTH: 726
<212> TYPE: DNA
<213> ORGANISM: Artificial Sequence
<220> FEATURE:
<223> OTHER INFORMATION: Description of Artificial Sequence: 342 gH1
      Fab (no hinge) HC with constant region
<220> FEATURE:
<221> NAME/KEY: CDS
<222> LOCATION: (64)..(726)

<400> SEQUENCE: 13

```
atgaagaaga ctgctatagc aattgcagtg gcgctagctg gtttcgccac cgtggcgcaa      60 gct gag gtt cag ctg gtc gag tct gga ggc ggg ctt gtc cag cct ggt     108
    Glu Val Gln Leu Val Glu Ser Gly Gly Gly Leu Val Gln Pro Gly
    1               5                   10                  15 ggg agc ctg cgt ctc tct tgt gca gtg agc ggc ttc agc tct acc aat     156
Gly Ser Leu Arg Leu Ser Cys Ala Val Ser Gly Phe Ser Ser Thr Asn
                20                  25                  30 tac cat gtg cac tgg gtc cgt cag gca cct ggg aag ggc ctg gag tgg     204
Tyr His Val His Trp Val Arg Gln Ala Pro Gly Lys Gly Leu Glu Trp
            35                  40                  45 atg ggt gtt att tgg ggc gac ggc gat aca tcc tac aac tcc gtc ctg     252
Met Gly Val Ile Trp Gly Asp Gly Asp Thr Ser Tyr Asn Ser Val Leu
        50                  55                  60 aag agc cgt ttc acc att tcc cgt gac acc tca aag aat acc gtt tac     300
Lys Ser Arg Phe Thr Ile Ser Arg Asp Thr Ser Lys Asn Thr Val Tyr
65                  70                  75 ctc cag atg aac tct ctc cgc gca gag gac aca gca gtc tat tac tgt     348
Leu Gln Met Asn Ser Leu Arg Ala Glu Asp Thr Ala Val Tyr Tyr Cys
80                  85                  90                  95 gca cgt caa ctg acc cac tat tac gtt ttg gca gcc tgg ggt caa ggg     396
Ala Arg Gln Leu Thr His Tyr Tyr Val Leu Ala Ala Trp Gly Gln Gly
                100                 105                 110 act ctg gtc aca gtc tcg agc gct tct aca aag ggc cca tcg gtc ttc     444
Thr Leu Val Thr Val Ser Ser Ala Ser Thr Lys Gly Pro Ser Val Phe
```

```
ccc ctg gca ccc tcc tcc aag agc acc tct ggg ggc aca gcg gcc ctg    492
Pro Leu Ala Pro Ser Ser Lys Ser Thr Ser Gly Gly Thr Ala Ala Leu
        130                 135                 140 ggc tgc ctg gtc aag gac tac ttc ccc gaa ccg gtg acg gtg tcg tgg    540
Gly Cys Leu Val Lys Asp Tyr Phe Pro Glu Pro Val Thr Val Ser Trp
145                 150                 155 aac tca ggc gcc ctg acc agc ggc gtg cac acc ttc ccg gct gtc cta    588
Asn Ser Gly Ala Leu Thr Ser Gly Val His Thr Phe Pro Ala Val Leu
160                 165                 170                 175 cag tcc tca gga ctc tac tcc ctc agc agc gtg gtg acc gtg ccc tcc    636
Gln Ser Ser Gly Leu Tyr Ser Leu Ser Ser Val Val Thr Val Pro Ser
            180                 185                 190 agc agc ttg ggc acc cag acc tac atc tgc aac gtg aat cac aag ccc    684
Ser Ser Leu Gly Thr Gln Thr Tyr Ile Cys Asn Val Asn His Lys Pro
        195                 200                 205 agc aac acc aag gtc gac aag aaa gtt gag ccc aaa tct tgt            726
Ser Asn Thr Lys Val Asp Lys Lys Val Glu Pro Lys Ser Cys
    210                 215                 220
```

<210> SEQ ID NO 14
<211> LENGTH: 221
<212> TYPE: PRT
<213> ORGANISM: Artificial Sequence
<220> FEATURE:
<223> OTHER INFORMATION: Synthetic Construct

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Ser Thr Asn Tyr
            20                  25                  30

His Val His Trp Val Arg Gln Ala Pro Gly Lys Gly Leu Glu Trp Met
        35                  40                  45

Gly Val Ile Trp Gly Asp Gly Asp Thr Ser Tyr Asn Ser Val Leu Lys
    50                  55                  60

Ser Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gln Leu Thr His Tyr Tyr Val Leu Ala Ala Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220
```

<210> SEQ ID NO 15
<211> LENGTH: 750
<212> TYPE: DNA
<213> ORGANISM: Artificial Sequence
<220> FEATURE:
<223> OTHER INFORMATION: Description of Artificial Sequence: 342 gH1
      Fab' HC with constant region
<220> FEATURE:
<221> NAME/KEY: CDS
<222> LOCATION: (64)..(750)

<400> SEQUENCE: 15

```
atgaagaaga ctgctatagc aattgcagtg gcgctagctg gtttcgccac cgtggcgcaa      60 gct gag gtt cag ctg gtc gag tct gga ggc ggg ctt gtc cag cct ggt       108
    Glu Val Gln Leu Val Glu Ser Gly Gly Gly Leu Val Gln Pro Gly
    1               5                   10                  15 ggg agc ctg cgt ctc tct tgt gca gtg agc ggc ttc agc tct acc aat       156
Gly Ser Leu Arg Leu Ser Cys Ala Val Ser Gly Phe Ser Ser Thr Asn
                20                  25                  30 tac cat gtg cac tgg gtg cgt cag gca cct ggg aag ggc ctg gag tgg       204
Tyr His Val His Trp Val Arg Gln Ala Pro Gly Lys Gly Leu Glu Trp
            35                  40                  45 atg ggt gtt att tgg ggc gac ggc gat aca tcc tac aac tcc gtc ctg       252
Met Gly Val Ile Trp Gly Asp Gly Asp Thr Ser Tyr Asn Ser Val Leu
        50                  55                  60 aag agc cgt ttc acc att tcc cgt gac acc tca aag aat acc gtt tac       300
Lys Ser Arg Phe Thr Ile Ser Arg Asp Thr Ser Lys Asn Thr Val Tyr
65                  70                  75 ctc cag atg aac tct ctc cgc gca gag gac aca gca gtc tat tac tgt       348
Leu Gln Met Asn Ser Leu Arg Ala Glu Asp Thr Ala Val Tyr Tyr Cys
80                  85                  90                  95 gca cgt caa ctg acc cac tat tac gtt ttg gca gcc tgg ggt caa ggg       396
Ala Arg Gln Leu Thr His Tyr Tyr Val Leu Ala Ala Trp Gly Gln Gly
                100                 105                 110 act ctg gtc aca gtc tcg agc gct tct aca aag ggc cca tcg gtc ttc       444
Thr Leu Val Thr Val Ser Ser Ala Ser Thr Lys Gly Pro Ser Val Phe
            115                 120                 125 ccc ctg gca ccc tcc tcc aag agc acc tct ggg ggc aca gcg gcc ctg       492
Pro Leu Ala Pro Ser Ser Lys Ser Thr Ser Gly Gly Thr Ala Ala Leu
        130                 135                 140 ggc tgc ctg gtc aag gac tac ttc ccc gaa ccg gtg acg gtg tcg tgg       540
Gly Cys Leu Val Lys Asp Tyr Phe Pro Glu Pro Val Thr Val Ser Trp
145                 150                 155 aac tca ggc gcc ctg acc agc ggc gtg cac acc ttc ccg gct gtc cta       588
Asn Ser Gly Ala Leu Thr Ser Gly Val His Thr Phe Pro Ala Val Leu
160                 165                 170                 175 cag tcc tca gga ctc tac tcc ctc agc agc gtg gtg acc gtg ccc tcc       636
Gln Ser Ser Gly Leu Tyr Ser Leu Ser Ser Val Val Thr Val Pro Ser
                180                 185                 190 agc agc ttg ggc acc cag acc tac atc tgc aac gtg aat cac aag ccc       684
Ser Ser Leu Gly Thr Gln Thr Tyr Ile Cys Asn Val Asn His Lys Pro
            195                 200                 205 agc aac acc aag gtc gac aag aaa gtt gag ccc aaa tct tgt gac aaa       732
Ser Asn Thr Lys Val Asp Lys Lys Val Glu Pro Lys Ser Cys Asp Lys
        210                 215                 220 act cac aca tgc gcc gcg                                               750
Thr His Thr Cys Ala Ala
            225
```

<210> SEQ ID NO 16
<211> LENGTH: 229
<212> TYPE: PRT

<213> ORGANISM: Artificial Sequence
<220> FEATURE:
<223> OTHER INFORMATION: Synthetic Construct

<400> SEQUENCE: 16

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Ser Thr Asn Tyr
            20                  25                  30

His Val His Trp Val Arg Gln Ala Pro Gly Lys Gly Leu Glu Trp Met
y       35                  40                  45

Gly Val Ile Trp Gly Asp Gly Asp Thr Ser Tyr Asn Ser Val Leu Lys
    50                  55                  60

Ser Arg Phe Thr Ile Ser Arg Asp Thr Ser Lys Asn Thr Val Tyr Leu
65              70                  75                  80

Gln Met Asn Ser Leu Arg Ala Glu Asp Thr Ala Val Tyr Tyr Cys Ala
                85                  90                  95

Arg Gln Leu Thr His Tyr Tyr Val Leu Ala Ala Trp Gly Gln Gly Thr
            100                 105                 110

Leu Val Thr Val Ser Ser Ala Ser Thr Lys Gly Pro Ser Val Phe Pro
y       115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145             150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Ala Ala
225
```

<210> SEQ ID NO 17
<211> LENGTH: 711
<212> TYPE: DNA
<213> ORGANISM: Artificial Sequence
<220> FEATURE:
<223> OTHER INFORMATION: Description of Artificial Sequence: hu342
       kappa LC
<220> FEATURE:
<221> NAME/KEY: CDS
<222> LOCATION: (1)..(711)

<400> SEQUENCE: 17

```
atg gac atg agg gtc ccc gct cag ctc ctg ggg ctc ctg cta ctc tgg     48
Met Asp Met Arg Val Pro Ala Gln Leu Leu Gly Leu Leu Leu Leu Trp
1               5                   10                  15 ctc cga ggt gcc aga tgt gat atc cag atg acc cag agt cca agc agt     96
Leu Arg Gly Ala Arg Cys Asp Ile Gln Met Thr Gln Ser Pro Ser Ser
            20                  25                  30 ctc tcc gcc agc gta ggc gat cgt gtg act att acc tgt cgt gcc agt    144
Leu Ser Ala Ser Val Gly Asp Arg Val Thr Ile Thr Cys Arg Ala Ser
        35                  40                  45 gag gac ctc tat tac aac ctg gcc tgg tat cag cgt aaa ccg ggc aaa    192
Glu Asp Leu Tyr Tyr Asn Leu Ala Trp Tyr Gln Arg Lys Pro Gly Lys
```

| | | | | | | | | | | | | | | | | |
|---|---|---|---|---|---|---|---|---|---|---|---|---|---|---|---|---|
| | | 50 | | | | 55 | | | | | 60 | | | | | |
| gcc | ccg | aag | ctg | ctc | atc | tat | gat | acg | tac | cgc | ctg | gct | gac | ggt | gtg | 240 |
| Ala | Pro | Lys | Leu | Leu | Ile | Tyr | Asp | Thr | Tyr | Arg | Leu | Ala | Asp | Gly | Val | |
| 65 | | | | 70 | | | | | 75 | | | | | 80 | | |
| cca | agc | cgt | ttc | agt | ggc | agt | ggc | agc | ggt | act | gac | tat | acc | ctc | aca | 288 |
| Pro | Ser | Arg | Phe | Ser | Gly | Ser | Gly | Ser | Gly | Thr | Asp | Tyr | Thr | Leu | Thr | |
| | | | | 85 | | | | | 90 | | | | | 95 | | |
| att | tcg | tct | ctc | cag | ccg | gaa | gat | ttc | gcc | tct | tac | tat | tgt | cag | caa | 336 |
| Ile | Ser | Ser | Leu | Gln | Pro | Glu | Asp | Phe | Ala | Ser | Tyr | Tyr | Cys | Gln | Gln | |
| | | | 100 | | | | | 105 | | | | | 110 | | | |
| tat | tac | aag | ttc | cct | ttc | acc | ttc | ggt | cag | ggc | act | aaa | gta | gaa | atc | 384 |
| Tyr | Tyr | Lys | Phe | Pro | Phe | Thr | Phe | Gly | Gln | Gly | Thr | Lys | Val | Glu | Ile | |
| | | 115 | | | | | 120 | | | | | 125 | | | | |
| aaa | cgt | acg | gtg | gct | gca | cca | tct | gtc | ttc | atc | ttc | ccg | cca | tct | gat | 432 |
| Lys | Arg | Thr | Val | Ala | Ala | Pro | Ser | Val | Phe | Ile | Phe | Pro | Pro | Ser | Asp | |
| 130 | | | | | 135 | | | | | 140 | | | | | | |
| gag | cag | ttg | aaa | tct | gga | act | gcc | tct | gtt | gtg | tgc | ctg | ctg | aat | aac | 480 |
| Glu | Gln | Leu | Lys | Ser | Gly | Thr | Ala | Ser | Val | Val | Cys | Leu | Leu | Asn | Asn | |
| 145 | | | | 150 | | | | | 155 | | | | | 160 | | |
| ttc | tat | ccc | aga | gag | gcc | aaa | gta | cag | tgg | aag | gtg | gat | aac | gcc | ctc | 528 |
| Phe | Tyr | Pro | Arg | Glu | Ala | Lys | Val | Gln | Trp | Lys | Val | Asp | Asn | Ala | Leu | |
| | | | | 165 | | | | | 170 | | | | | 175 | | |
| caa | tcg | ggt | aac | tcc | cag | gag | agt | gtc | aca | gag | cag | gac | agc | aag | gac | 576 |
| Gln | Ser | Gly | Asn | Ser | Gln | Glu | Ser | Val | Thr | Glu | Gln | Asp | Ser | Lys | Asp | |
| | | | 180 | | | | | 185 | | | | | 190 | | | |
| agc | acc | tac | agc | ctc | agc | agc | acc | ctg | acg | ctg | agc | aaa | gca | gac | tac | 624 |
| Ser | Thr | Tyr | Ser | Leu | Ser | Ser | Thr | Leu | Thr | Leu | Ser | Lys | Ala | Asp | Tyr | |
| | | 195 | | | | | 200 | | | | | 205 | | | | |
| gag | aaa | cac | aaa | gtc | tac | gcc | tgc | gaa | gtc | acc | cat | cag | ggc | ctg | agc | 672 |
| Glu | Lys | His | Lys | Val | Tyr | Ala | Cys | Glu | Val | Thr | His | Gln | Gly | Leu | Ser | |
| 210 | | | | | 215 | | | | | 220 | | | | | | |
| tcg | ccc | gtc | aca | aag | agc | ttc | aac | agg | gga | gag | tgt | tag | | | | 711 |
| Ser | Pro | Val | Thr | Lys | Ser | Phe | Asn | Arg | Gly | Glu | Cys | | | | | |
| 225 | | | | 230 | | | | | 235 | | | | | | | |

<210> SEQ ID NO 18
<211> LENGTH: 236
<212> TYPE: PRT
<213> ORGANISM: Artificial Sequence
<220> FEATURE:
<223> OTHER INFORMATION: Synthetic Construct

<400> SEQUENCE: 18

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
y           35                  40                  45

Glu Asp Leu Tyr Tyr Asn Leu Ala Trp Tyr Gln Arg Lys Pro Gly Lys
        50                  55                  60

Ala Pro Lys Leu Leu Ile Tyr Asp Thr Tyr Arg Leu Ala Asp Gly Val
65                  70                  75                  80

Pro Ser Arg Phe Ser Gly Ser Gly Ser Gly Thr Asp Tyr Thr Leu Thr
                85                  90                  95

Ile Ser Ser Leu Gln Pro Glu Asp Phe Ala Ser Tyr Tyr Cys Gln Gln
            100                 105                 110

Tyr Tyr Lys Phe Pro Phe Thr Phe Gly Gln Gly Thr Lys Val Glu Ile
y       115                 120                 125

```
Lys Arg Thr Val Ala Ala Pro Ser Val Phe Ile Phe Pro Pro Ser Asp
        130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
225                 230                 235
```

<210> SEQ ID NO 19
<211> LENGTH: 1392
<212> TYPE: DNA
<213> ORGANISM: Artificial Sequence
<220> FEATURE:
<223> OTHER INFORMATION: Description of Artificial Sequence: hu342 aglyP-huIgG4 HC
<220> FEATURE:
<221> NAME/KEY: CDS
<222> LOCATION: (1)..(1392)

<400> SEQUENCE: 19

```
atg gac tgg acc tgg agg gtc ttc tgc ttg ctg gct gta gca cca ggt      48
Met Asp Trp Thr Trp Arg Val Phe Cys Leu Leu Ala Val Ala Pro Gly
1               5                   10                  15 gcc cac tcc gaa gta caa ttg gtc gag tct gga ggc ggg ctt gtc cag      96
Ala His Ser Glu Val Gln Leu Val Glu Ser Gly Gly Gly Leu Val Gln
                20                  25                  30 cct ggt ggg agc ctg cgt ctc tct tgt gca gtg agc ggc ttc agc tct     144
Pro Gly Gly Ser Leu Arg Leu Ser Cys Ala Val Ser Gly Phe Ser Ser
            35                  40                  45 acc aat tac cat gtg cac tgg gtg cgt cag gca cct ggg aag ggc ctg     192
Thr Asn Tyr His Val His Trp Val Arg Gln Ala Pro Gly Lys Gly Leu
        50                  55                  60 gag tgg atg ggt gtt att tgg ggc gac ggc gat aca tcc tac aac tcc     240
Glu Trp Met Gly Val Ile Trp Gly Asp Gly Asp Thr Ser Tyr Asn Ser
65                  70                  75                  80 gtc ctg aag agc cgt ttc acc att tcc cgt gac acc tca aag aat acc     288
Val Leu Lys Ser Arg Phe Thr Ile Ser Arg Asp Thr Ser Lys Asn Thr
                85                  90                  95 gtt tac ctc cag atg aac tct ctc cgc gca gag gac aca gca gtc tat     336
Val Tyr Leu Gln Met Asn Ser Leu Arg Ala Glu Asp Thr Ala Val Tyr
                100                 105                 110 tac tgt gca cgt caa ctg acc cac tat tac gtt ttg gca gcc tgg ggt     384
Tyr Cys Ala Arg Gln Leu Thr His Tyr Tyr Val Leu Ala Ala Trp Gly
            115                 120                 125 caa ggg act ctg gtc aca gtc tcg agc gct tca acc aag ggc cca tcc     432
Gln Gly Thr Leu Val Thr Val Ser Ser Ala Ser Thr Lys Gly Pro Ser
        130                 135                 140 gtc ttc ccc ctg gcg ccc tgc tcc aga tct acc tcc gag agc aca gcc     480
Val Phe Pro Leu Ala Pro Cys Ser Arg Ser Thr Ser Glu Ser Thr Ala
145                 150                 155                 160 gcc ctg ggc tgc ctg gtc aag gac tac ttc ccc gaa ccg gtg acg gtg     528
Ala Leu Gly Cys Leu Val Lys Asp Tyr Phe Pro Glu Pro Val Thr Val
                165                 170                 175
```

```
tcg tgg aac tca ggc gcc ctg acc agc ggc gtg cac acc ttc ccg gct    576
Ser Trp Asn Ser Gly Ala Leu Thr Ser Gly Val His Thr Phe Pro Ala
        180                 185                 190 gtc cta cag tcc tca gga ctc tac tcc ctc agc agc gtg gtg acc gtg    624
Val Leu Gln Ser Ser Gly Leu Tyr Ser Leu Ser Ser Val Val Thr Val
        195                 200                 205 ccc tcc agc agc ttg ggc acg aag acc tac acc tgc aac gta gat cac    672
Pro Ser Ser Ser Leu Gly Thr Lys Thr Tyr Thr Cys Asn Val Asp His
    210                 215                 220 aag ccc agc aac acc aag gtg gac aag aga gtt gag tcc aaa tat ggt    720
Lys Pro Ser Asn Thr Lys Val Asp Lys Arg Val Glu Ser Lys Tyr Gly
225                 230                 235                 240 ccc cca tgc cca ccg tgc cca gca cct gag ttc ctg ggg gga cca tca    768
Pro Pro Cys Pro Pro Cys Pro Ala Pro Glu Phe Leu Gly Gly Pro Ser
            245                 250                 255 gtc ttc ctg ttc ccc cca aaa ccc aag gac act ctc atg atc tcc cgg    816
Val Phe Leu Phe Pro Pro Lys Pro Lys Asp Thr Leu Met Ile Ser Arg
        260                 265                 270 acc cct gag gtc acg tgc gtg gtg gtg gac gtg agc cag gaa gac ccc    864
Thr Pro Glu Val Thr Cys Val Val Val Asp Val Ser Gln Glu Asp Pro
        275                 280                 285 gag gtc cag ttc aac tgg tac gtg gat ggc gtg gag gtg cat aat gcc    912
Glu Val Gln Phe Asn Trp Tyr Val Asp Gly Val Glu Val His Asn Ala
    290                 295                 300 aag aca aag ccg cgg gag gag cag ttc aac agc gcg tac cgt gtg gtc    960
Lys Thr Lys Pro Arg Glu Glu Gln Phe Asn Ser Ala Tyr Arg Val Val
305                 310                 315                 320 agc gtc ctc acc gtc ctg cac cag gac tgg ctg aac ggc aag gag tac    1008
Ser Val Leu Thr Val Leu His Gln Asp Trp Leu Asn Gly Lys Glu Tyr
            325                 330                 335 aag tgc aag gtc tcc aac aaa ggc ctc ccg tcc tcc atc gag aaa acc    1056
Lys Cys Lys Val Ser Asn Lys Gly Leu Pro Ser Ser Ile Glu Lys Thr
        340                 345                 350 atc tcc aaa gcc aaa ggg cag ccc cga gag cca cag gtg tac acc ctg    1104
Ile Ser Lys Ala Lys Gly Gln Pro Arg Glu Pro Gln Val Tyr Thr Leu
        355                 360                 365 ccc cca tcc cag gag gag atg acc aag aac cag gtc agc ctg acc tgc    1152
Pro Pro Ser Gln Glu Glu Met Thr Lys Asn Gln Val Ser Leu Thr Cys
    370                 375                 380 ctg gtc aaa ggc ttc tac ccc agc gac atc gcc gtg gag tgg gag agc    1200
Leu Val Lys Gly Phe Tyr Pro Ser Asp Ile Ala Val Glu Trp Glu Ser
385                 390                 395                 400 aat ggg cag ccg gag aac aac tac aag acc acg cct ccc gtc ctc gat    1248
Asn Gly Gln Pro Glu Asn Asn Tyr Lys Thr Thr Pro Pro Val Leu Asp
            405                 410                 415 tcc gac ggc tcc ttc ttc ctc tac agc agg cta acc gtg gac aag agc    1296
Ser Asp Gly Ser Phe Phe Leu Tyr Ser Arg Leu Thr Val Asp Lys Ser
        420                 425                 430 agg tgg cag gag ggg aat gtc ttc tca tgc tcc gtg atg cat gag gct    1344
Arg Trp Gln Glu Gly Asn Val Phe Ser Cys Ser Val Met His Glu Ala
        435                 440                 445 ctg cac aac cac tac aca cag aag agc ctc tcc ctg tct ctg ggt tga    1392
Leu His Asn His Tyr Thr Gln Lys Ser Leu Ser Leu Ser Leu Gly
    450                 455                 460
```

<210> SEQ ID NO 20
<211> LENGTH: 463
<212> TYPE: PRT
<213> ORGANISM: Artificial Sequence
<220> FEATURE:

<223> OTHER INFORMATION: Synthetic Construct

<400> SEQUENCE: 20

```
Met Asp Trp Thr Trp Arg Val Phe Cys Leu Leu Ala Val Ala Pro Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Val Ser Gly Phe Ser Ser
y           35                  40                  45

Thr Asn Tyr His Val His Trp Val Arg Gln Ala Pro Gly Lys Gly Leu
    50                  55                  60

Glu Trp Met Gly Val Ile Trp Gly Asp Gly Asp Thr Ser Tyr Asn Ser
65                  70                  75                  80

Val Leu Lys Ser Arg Phe Thr Ile Ser Arg Asp Thr Ser Lys Asn Thr
                85                  90                  95

Val Tyr Leu Gln Met Asn Ser Leu Arg Ala Glu Asp Thr Ala Val Tyr
            100                 105                 110

Tyr Cys Ala Arg Gln Leu Thr His Tyr Val Leu Ala Ala Trp Gly
y       115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
y       195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
y       275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Ala Tyr Arg Val Val
305                 310                 315                 320

Ser Val Leu Thr Val Leu His Gln Asp Trp Leu Asn Gly Lys Glu Tyr
            325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
y       355                 360                 365

Pro Pro Ser Gln Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400
```

Asn Gly Gln Pro Glu Asn Asn Tyr Lys Thr Thr Pro Val Leu Asp
            405                 410                 415

Ser Asp Gly Ser Phe Phe Leu Tyr Ser Arg Leu Thr Val Asp Lys Ser
        420                 425                 430

Arg Trp Gln Glu Gly Asn Val Phe Ser Cys Ser Val Met His Glu Ala
    435                 440                 445

Leu His Asn His Tyr Thr Gln Lys Ser Leu Ser Leu Ser Leu Gly
    450                 455                 460

<210> SEQ ID NO 21
<211> LENGTH: 1438
<212> TYPE: DNA
<213> ORGANISM: Artificial Sequence
<220> FEATURE:
<223> OTHER INFORMATION: Description of Artificial Sequence: 342 gL4gH1
      VH3 (V+C) Fab (no hinge) vector DNA

<400> SEQUENCE: 21
atgaaaaaga cagctatcgc aattgcagtg gccttggctg gtttcgctac cgtagcgcaa      60
gctgatatcc agatgaccca gagtccaagc agtctctccg ccagcgtagg cgatcgtgtg     120
actattacct gtcgtgccag tgaggacctc tattacaacc tggcctggta tcagcgtaaa     180
ccgggcaaag ccccgaagct gctcatctat gatacgtacc gcctggctga cggtgtgcca     240
agccgtttca gtggcagtgg cagcggtact gactataccc tcacaatttc gtctctccag     300
ccggaagatt tcgcctctta ctattgtcag caatattaca agttcccttt caccttcggt     360
cagggcacta agtagaaat caaacgtacg gtagcggccc catctgtctt catcttcccg      420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca agcagactac gagaaacac aaagtctacg cctgcgaagt cacccatcag     660
ggcctgagct caccagtaac aaaaagtttt aatagagggg agtgttaaaa tgaagaagac     720
tgctatagca attgcagtgg cgctagctgg tttcgccacc gtggcgcaag ctgaggttca     780
gctggtcgag tctggaggcg gcttgtcca gcctggtggg agcctgcgtc tctcttgtgc     840
agtgagcggc ttcagctcta ccaattacca tgtgcactgg gtgcgtcagg cacctgggaa     900
gggcctggag tggatgggtg ttatttgggg cgacggcgat acatcctaca actccgtcct     960
gaagagccgt ttcaccattt cccgtgacac ctcaaagaat accgtttacc tccagatgaa    1020
ctctctccgc gcagaggaca cagcagtcta ttactgtgca cgtcaactga cccactatta    1080
cgttttggca gcctggggtc aagggactct ggtcacagtc tcgagcgctt ctacaaaggg    1140
cccatcggtc ttccccctgg cacctcctc caagagcacc tctgggggca gcggccct      1200 gggctgcctg gtcaaggact acttccccga accggtgacg gtgtcgtgga actcaggcgc    1260
cctgaccagc ggcgtgcaca ccttcccggc tgtcctacag tcctcaggac tctactccct    1320
cagcagcgtg gtgaccgtgc cctccagcag cttgggcacc cagacctaca tctgcaacgt    1380
gaatcacaag cccagcaaca ccaaggtcga caagaaagtt gagcccaaat cttgttaa     1438

<210> SEQ ID NO 22
<211> LENGTH: 1459
<212> TYPE: DNA
<213> ORGANISM: Artificial Sequence
<220> FEATURE:
<223> OTHER INFORMATION: Description of Artificial Sequence: 342 gL4gH1
      VH3 (V+C) Fab' vector DNA -continued

```
<400> SEQUENCE: 22
atgaaaaaga cagctatcgc aattgcagtg gccttggctg gtttcgctac cgtagcgcaa      60
gctgatatcc agatgaccca gagtccaagc agtctctccg ccagcgtagg cgatcgtgtg     120
actattacct gtcgtgccag tgaggacctc tattacaacc tggcctggta tcagcgtaaa     180
ccgggcaaag ccccgaagct gctcatctat gatacgtacc gcctggctga cggtgtgcca     240
agccgtttca gtggcagtgg cagcggtact gactataccc tcacaatttc gtctctccag     300
ccggaagatt tcgcctctta ctattgtcag caatattaca gttccctttt caccttcggt     360
cagggcacta aagtagaaat caaacgtacg gtagcggccc catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag acagcacct acagcctcag cagcaccctg      600
acgctgagca aagcagacta cgagaaacac aaagtctacg cctgcgaagt cacccatcag     660
ggcctgagct caccagtaac aaaaagtttt aatagagggg agtgttaaaa tgaagaagac     720
tgctatagca attgcagtgg cgctagctgg tttcgccacc gtggcgcaag ctgaggttca     780
gctggtcgag tctggaggcg gcttgtcca gcctggtggg agcctgcgtc tctcttgtgc      840
agtgagcggc ttcagctcta ccaattacca tgtgcactgg gtgcgtcagg cacctgggaa     900
gggcctggag tggatgggtg ttatttgggg cgacggcgat acatcctaca actccgtcct     960
gaagagccgt ttcaccattt cccgtgacac ctcaaagaat accgtttacc tccagatgaa    1020
ctctctccgc gcagaggaca cagcagtcta ttactgtgca cgtcaactga cccactatta    1080
cgttttggca gcctgggtc aagggactct ggtcacagtc tcgagcgctt ctacaaaggg    1140
cccatcggtc ttccccctgg cacactcctc caagagcacc tctgggggca gcggcccct    1200 gggctgcctg gtcaaggact acttccccga accggtgacg gtgtcgtgga actcaggcgc    1260
cctgaccagc ggcgtgcaca ccttcccggc tgtcctacag tcctcaggac tctactccct    1320
cagcagcgtg gtgaccgtgc cctccagcag cttgggcacc cagacctaca tctgcaacgt    1380
gaatcacaag cccagcaaca ccaaggtcga caagaaagtt gagcccaaat cttgtgacaa    1440
aactcacaca tgcgccgcg                                                 1459

<210> SEQ ID NO 23
<211> LENGTH: 986
<212> TYPE: DNA
<213> ORGANISM: Escherichia coli
<220> FEATURE:
<221> NAME/KEY: CDS
<222> LOCATION: (379)..(945)
<300> PUBLICATION INFORMATION:
<308> DATABASE ACCESSION NUMBER: GenBank / D86610
<309> DATABASE ENTRY DATE: 2009-01-10
<313> RELEVANT RESIDUES IN SEQ ID NO: (1)..(986)

<400> SEQUENCE: 23
atagtgagga taatcctgat gatgcgcacc gtgctttcat ctatcgaacg caaaaatcat      60
tctctaagta aatgaatgga ttgcatgcgt tcactcaat tgtactttaa ttgaccaacc     120
ccgcttatta actttctgta tcacttttc ttataaaaaa tcatgtaaaa ccgctcgcca      180
agaccgcacc aatcgggtaa tctcgaactc gttttgcctc ggcggtagat tatcctcaca     240
gcatataatt ttgtgcgtta gtccacagat ttggccttaa ggaattgttt caacatgccc     300
aggtaattag tctcgtgtcg cttggcattt ttttataacg atatttgtcg ttaaggactt     360
```

```
caagggaaaa caaacaac atg gtc aaa tct caa ccg att ttg aga tat atc      411
                    Met Val Lys Ser Gln Pro Ile Leu Arg Tyr Ile
                     1               5                      10 ttg cgc ggg att ccc gcg att gca gta gcg gtt ctg ctt tct gca tgt      459
Leu Arg Gly Ile Pro Ala Ile Ala Val Ala Val Leu Leu Ser Ala Cys
            15                  20                  25 agt gca aat aac acc gca aag aat atg cat cct gag aca cgt gca gtg      507
Ser Ala Asn Asn Thr Ala Lys Asn Met His Pro Glu Thr Arg Ala Val
        30                  35                  40 ggt agt gaa aca tca tca ctg caa gct tct cag gat gaa ttt gaa aac      555
Gly Ser Glu Thr Ser Ser Leu Gln Ala Ser Gln Asp Glu Phe Glu Asn
    45                  50                  55 ctg gtt cgt aat gtc gac gta aaa tcg cga att atg gat cag tat gct      603
Leu Val Arg Asn Val Asp Val Lys Ser Arg Ile Met Asp Gln Tyr Ala
60                  65                  70                  75 gac tgg aaa ggc gta cgt tat cgt ctg ggc ggc agc act aaa aaa ggt      651
Asp Trp Lys Gly Val Arg Tyr Arg Leu Gly Gly Ser Thr Lys Lys Gly
                80                  85                  90 atc gat tgt tct ggt ttc gta cag cgt aca ttc cgt gag caa ttt ggc      699
Ile Asp Cys Ser Gly Phe Val Gln Arg Thr Phe Arg Glu Gln Phe Gly
            95                  100                 105 tta gaa ctt ccg cgt tcg act tac gaa cag cag gaa atg ggt aaa tct      747
Leu Glu Leu Pro Arg Ser Thr Tyr Glu Gln Gln Glu Met Gly Lys Ser
        110                 115                 120 gtt tcc cgc agt aat ttg cgt acg ggt gat tta gtt ctg ttc cgt gcc      795
Val Ser Arg Ser Asn Leu Arg Thr Gly Asp Leu Val Leu Phe Arg Ala
    125                 130                 135 ggt tca acg gga cgc cat gtc ggt att tat atc ggc aac aat cag ttt      843
Gly Ser Thr Gly Arg His Val Gly Ile Tyr Ile Gly Asn Asn Gln Phe
140                 145                 150                 155 gtc cat gct tcc acc agc agt ggt gtt att att tcc agc atg aat gaa      891
Val His Ala Ser Thr Ser Ser Gly Val Ile Ile Ser Ser Met Asn Glu
                160                 165                 170 ccg tac tgg aag aag cgt tac aac gaa gca cgc cgg gtt ctc agc cgc      939
Pro Tyr Trp Lys Lys Arg Tyr Asn Glu Ala Arg Arg Val Leu Ser Arg
            175                 180                 185 agc taa taaaccgttt ggatgcaatc ccttggctat cctgacgagt t                986
Ser
```

<210> SEQ ID NO 24
<211> LENGTH: 188
<212> TYPE: PRT
<213> ORGANISM: Escherichia coli

<400> SEQUENCE: 24

```
Met Val Lys Ser Gln Pro Ile Leu Arg Tyr Ile Leu Arg Gly Ile Pro
1               5                   10                  15

Ala Ile Ala Val Ala Val Leu Leu Ser Ala Cys Ser Ala Asn Asn Thr
            20                  25                  30

Ala Lys Asn Met His Pro Glu Thr Arg Ala Val Gly Ser Glu Thr Ser
y           35                  40                  45

Ser Leu Gln Ala Ser Gln Asp Glu Phe Glu Asn Leu Val Arg Asn Val
        50                  55                  60

Asp Val Lys Ser Arg Ile Met Asp Gln Tyr Ala Asp Trp Lys Gly Val
65                  70                  75                  80

Arg Tyr Arg Leu Gly Gly Ser Thr Lys Lys Gly Ile Asp Cys Ser Gly
                85                  90                  95

Phe Val Gln Arg Thr Phe Arg Glu Gln Phe Gly Leu Glu Leu Pro Arg
```

-continued

```
                  100                 105                 110
Ser Thr Tyr Glu Gln Gln Glu Met Gly Lys Ser Val Ser Arg Ser Asn
  y             115                 120                 125

Leu Arg Thr Gly Asp Leu Val Leu Phe Arg Ala Gly Ser Thr Gly Arg
        130                 135                 140

His Val Gly Ile Tyr Ile Gly Asn Asn Gln Phe Val His Ala Ser Thr
145                 150                 155                 160

Ser Ser Gly Val Ile Ile Ser Ser Met Asn Glu Pro Tyr Trp Lys Lys
                165                 170                 175

Arg Tyr Asn Glu Ala Arg Arg Val Leu Ser Arg Ser
            180                 185

<210> SEQ ID NO 25
<211> LENGTH: 2196
<212> TYPE: DNA
<213> ORGANISM: Escherichia coli
<220> FEATURE:
<221> NAME/KEY: CDS
<222> LOCATION: (69)..(2117)
<220> FEATURE:
<221> NAME/KEY: sig_peptide
<222> LOCATION: (69)..(134)
<300> PUBLICATION INFORMATION:
<308> DATABASE ACCESSION NUMBER: GenBank / M75634
<309> DATABASE ENTRY DATE: 1993-04-26
<313> RELEVANT RESIDUES IN SEQ ID NO: (1)..(2196)

<400> SEQUENCE: 25
gaattcgggt atgtctttga ttgtgcgcgc agaacacctg gtgttctgaa acggaggccg       60 ggccaggc atg aac atg ttt ttt agg ctt acc gcg tta gct ggc ctg ctt      110
         Met Asn Met Phe Phe Arg Leu Thr Ala Leu Ala Gly Leu Leu
           1               5                  10 gca ata gca ggc cag acc ttc gct gta gaa gat atc acg cgt gct gat      158
Ala Ile Ala Gly Gln Thr Phe Ala Val Glu Asp Ile Thr Arg Ala Asp
 15              20                  25                  30 caa att ccg gta tta aag gaa gag acg cag cat gcg acg gta agt gag      206
Gln Ile Pro Val Leu Lys Glu Glu Thr Gln His Ala Thr Val Ser Glu
                 35                  40                  45 cgc gta acg tcg cgc ttc acc cgt tct cat tat cgc cag ttc gac ctc      254
Arg Val Thr Ser Arg Phe Thr Arg Ser His Tyr Arg Gln Phe Asp Leu
             50                  55                  60 gat cag gca ttt tcg gcc aaa atc ttt gac cgc tac ctg aat ctg ctc      302
Asp Gln Ala Phe Ser Ala Lys Ile Phe Asp Arg Tyr Leu Asn Leu Leu
         65                  70                  75 gat tac agc cac aac gtg ctg ctg gca agc gat gtt gaa cag ttc gcg      350
Asp Tyr Ser His Asn Val Leu Leu Ala Ser Asp Val Glu Gln Phe Ala
     80                  85                  90 aaa aag aaa acc gag tta ggc gat gaa ctg cgt tca ggc aaa ctc gac      398
Lys Lys Lys Thr Glu Leu Gly Asp Glu Leu Arg Ser Gly Lys Leu Asp
 95                 100                 105                 110 gtt ttc tac gat ctc tac aat ctg gcg caa aag cgc gtt ttt gag cgt      446
Val Phe Tyr Asp Leu Tyr Asn Leu Ala Gln Lys Arg Arg Phe Glu Arg
                115                 120                 125 tac cag tac gct ttg tcg gta ctg gaa aag ccg atg gat ttc acc ggc      494
Tyr Gln Tyr Ala Leu Ser Val Leu Glu Lys Pro Met Asp Phe Thr Gly
            130                 135                 140 aac gac act tat aac ctt gac cgc agc aaa gcg ccc tgg ccg aaa aac      542
Asn Asp Thr Tyr Asn Leu Asp Arg Ser Lys Ala Pro Trp Pro Lys Asn
        145                 150                 155 gag gct gag ttg aac gcg ctg tgg gac agt aaa gtc aaa ttc gac gag      590
Glu Ala Glu Leu Asn Ala Leu Trp Asp Ser Lys Val Lys Phe Asp Glu
```

```
                 160                 165                 170
tta agc ctg aag ctg aca gga aaa acg gat aaa gaa att cgt gaa acc    638
Leu Ser Leu Lys Leu Thr Gly Lys Thr Asp Lys Glu Ile Arg Glu Thr
175                 180                 185                 190 ctg act cgc cgc tac aaa ttt gcc att cgt cgt ctg gcg caa acc aac    686
Leu Thr Arg Arg Tyr Lys Phe Ala Ile Arg Arg Leu Ala Gln Thr Asn
                195                 200                 205 agc gaa gat gtt ttc tcg ctg gca atg acg gcg ttt gcg cgt gaa atc    734
Ser Glu Asp Val Phe Ser Leu Ala Met Thr Ala Phe Ala Arg Glu Ile
            210                 215                 220 gac ccg cat acc aac tat ctt tcc ccg cgt aat acc gaa cag ttc aac    782
Asp Pro His Thr Asn Tyr Leu Ser Pro Arg Asn Thr Glu Gln Phe Asn
        225                 230                 235 act gaa atg agt ttg tcg ctg gaa ggt att ggc gca gtg ctg caa atg    830
Thr Glu Met Ser Leu Ser Leu Glu Gly Ile Gly Ala Val Leu Gln Met
240                 245                 250 gat gat gac tac acc gtt atc aat tcg atg gtg gca ggt ggt ccg gca    878
Asp Asp Asp Tyr Thr Val Ile Asn Ser Met Val Ala Gly Gly Pro Ala
255                 260                 265                 270 gcg aag agt aaa gct atc agc gtt ggt gac aaa att gtc ggt gtt ggt    926
Ala Lys Ser Lys Ala Ile Ser Val Gly Asp Lys Ile Val Gly Val Gly
                275                 280                 285 caa aca ggc aag ccg atg gtt gac gtg att ggc tgg cgt ctt gat gat    974
Gln Thr Gly Lys Pro Met Val Asp Val Ile Gly Trp Arg Leu Asp Asp
            290                 295                 300 gtg gtt gcc tta att aaa ggg ccg aag ggc agt aaa gtt cgt ctg gaa   1022
Val Val Ala Leu Ile Lys Gly Pro Lys Gly Ser Lys Val Arg Leu Glu
        305                 310                 315 att tta cct gct ggt aaa ggg acc aag acc cgt act gta acg ttg acc   1070
Ile Leu Pro Ala Gly Lys Gly Thr Lys Thr Arg Thr Val Thr Leu Thr
320                 325                 330 cgt gaa cgt att cgt ctc gaa gac cgc gcg gtt aaa atg tcg gtg aag   1118
Arg Glu Arg Ile Arg Leu Glu Asp Arg Ala Val Lys Met Ser Val Lys
335                 340                 345                 350 acc gtc ggt aaa gag aaa gtc ggc gtg ctg gat att ccg ggc ttc tat   1166
Thr Val Gly Lys Glu Lys Val Gly Val Leu Asp Ile Pro Gly Phe Tyr
                355                 360                 365 gtg ggt ttg aca gac gat gtc aaa gtg caa ctg cag aaa ctg gaa aaa   1214
Val Gly Leu Thr Asp Asp Val Lys Val Gln Leu Gln Lys Leu Glu Lys
            370                 375                 380 cag aat gtc agc agc gtc atc atc gac ctg cgt agc aat ggc ggt ggg   1262
Gln Asn Val Ser Ser Val Ile Ile Asp Leu Arg Ser Asn Gly Gly Gly
        385                 390                 395 gcg tta act gaa gcc gta tcg ctc tcc ggt ctg ttt att cct gcg ggt   1310
Ala Leu Thr Glu Ala Val Ser Leu Ser Gly Leu Phe Ile Pro Ala Gly
400                 405                 410 ccc att gtt cag gtc cgc gat aac aac ggc aag gtt cgt gaa gat agc   1358
Pro Ile Val Gln Val Arg Asp Asn Asn Gly Lys Val Arg Glu Asp Ser
415                 420                 425                 430 gat acc gac gga cag gtt ttc tat aaa ggc ccg ctg gtg gtg ctg gtt   1406
Asp Thr Asp Gly Gln Val Phe Tyr Lys Gly Pro Leu Val Val Leu Val
                435                 440                 445 gac cgc ttc agt gct tcg gct tca gaa atc ttt gcc gcg gca atg cag   1454
Asp Arg Phe Ser Ala Ser Ala Ser Glu Ile Phe Ala Ala Ala Met Gln
            450                 455                 460 gat tac ggt cgt gcg ctg gtt gtg ggt gaa ccg acg ttt ggt aaa ggc   1502
Asp Tyr Gly Arg Ala Leu Val Val Gly Glu Pro Thr Phe Gly Lys Gly
        465                 470                 475 acc gtt cag caa tac cgt tca ttg aac cgt att tac gat cag atg tta   1550
```

```
Thr Val Gln Gln Tyr Arg Ser Leu Asn Arg Ile Tyr Asp Gln Met Leu
        480                 485                 490 cgt cct gaa tgg cca gcg ctg ggt tct gtg cag tac acg atc cag aaa        1598
Arg Pro Glu Trp Pro Ala Leu Gly Ser Val Gln Tyr Thr Ile Gln Lys
495                 500                 505                 510 ttc tat cgc gtt aac ggc ggc agt acg caa cgt aaa ggc gta acg cca        1646
Phe Tyr Arg Val Asn Gly Gly Ser Thr Gln Arg Lys Gly Val Thr Pro
                    515                 520                 525 gac atc atc atg ccg acg ggt aat gaa gaa acg gaa acg ggt gag aaa        1694
Asp Ile Ile Met Pro Thr Gly Asn Glu Glu Thr Glu Thr Gly Glu Lys
                530                 535                 540 ttc gaa gat aac gcg ctg ccg tgg gat agc att gat gcc gcg act tat        1742
Phe Glu Asp Asn Ala Leu Pro Trp Asp Ser Ile Asp Ala Ala Thr Tyr
545                 550                 555 gtg aaa tca gga gat tta acg gcc ttt gaa ccg gag ctg ctg aag gaa        1790
Val Lys Ser Gly Asp Leu Thr Ala Phe Glu Pro Glu Leu Leu Lys Glu
            560                 565                 570 cat aat gcg cgt atc gcg aaa gat cct gag ttc cag aac atc atg aag        1838
His Asn Ala Arg Ile Ala Lys Asp Pro Glu Phe Gln Asn Ile Met Lys
575                 580                 585                 590 gat atc gcg cgc ttc aac gct atg aag gac aag cgc aat atc gtt tct        1886
Asp Ile Ala Arg Phe Asn Ala Met Lys Asp Lys Arg Asn Ile Val Ser
                595                 600                 605 ctg aat tac gct gtg cgt gag aaa gag aat aat gaa gat gat gcg acg        1934
Leu Asn Tyr Ala Val Arg Glu Lys Glu Asn Asn Glu Asp Asp Ala Thr
            610                 615                 620 cgt ctg gcg cgt ttg aac gaa cgc ttt aaa cgc gaa ggt aaa ccg gag        1982
Arg Leu Ala Arg Leu Asn Glu Arg Phe Lys Arg Glu Gly Lys Pro Glu
625                 630                 635 ttg aag aaa ctg gat gat cta ccg aaa gat tac cag gag ccg gat cct        2030
Leu Lys Lys Leu Asp Asp Leu Pro Lys Asp Tyr Gln Glu Pro Asp Pro
640                 645                 650 tat ctg gat gag acg gtg aat atc gca ctc gat ctg gcg aag ctt gaa        2078
Tyr Leu Asp Glu Thr Val Asn Ile Ala Leu Asp Leu Ala Lys Leu Glu
655                 660                 665                 670 aaa gcc aga ccc gcg gaa caa ccc gct ccc gtc aag taa tatcaatcag        2127
Lys Ala Arg Pro Ala Glu Gln Pro Ala Pro Val Lys
                675                 680 gcacaagaaa ttgtgcctga tttttaaca gcgacaagat gccgtaaatc agatgctaca       2187
aaatgtaaa                                                              2196

<210> SEQ ID NO 26
<211> LENGTH: 682
<212> TYPE: PRT
<213> ORGANISM: Escherichia coli

<400> SEQUENCE: 26

Met Asn Met Phe Phe Arg Leu Thr Ala Leu Ala Gly Leu Leu Ala Ile
1               5                   10                  15

Ala Gly Gln Thr Phe Ala Val Glu Asp Ile Thr Arg Ala Asp Gln Ile
            20                  25                  30

Pro Val Leu Lys Glu Glu Thr Gln His Ala Thr Val Ser Glu Arg Val
        35                  40                  45

Thr Ser Arg Phe Thr Arg Ser His Tyr Arg Gln Phe Asp Leu Asp Gln
    50                  55                  60

Ala Phe Ser Ala Lys Ile Phe Asp Arg Tyr Leu Asn Leu Leu Asp Tyr
65                  70                  75                  80

Ser His Asn Val Leu Leu Ala Ser Asp Val Glu Gln Phe Ala Lys Lys
```

```
                 85                  90                  95
Lys Thr Glu Leu Gly Asp Glu Leu Arg Ser Gly Lys Leu Asp Val Phe
                100                 105                 110

Tyr Asp Leu Tyr Asn Leu Ala Gln Lys Arg Phe Glu Arg Tyr Gln
        115                 120                 125

Tyr Ala Leu Ser Val Leu Glu Lys Pro Met Asp Phe Thr Gly Asn Asp
        130                 135                 140

Thr Tyr Asn Leu Asp Arg Ser Lys Ala Pro Trp Pro Lys Asn Glu Ala
145                 150                 155                 160

Glu Leu Asn Ala Leu Trp Asp Ser Lys Val Lys Phe Asp Glu Leu Ser
                165                 170                 175

Leu Lys Leu Thr Gly Lys Thr Asp Lys Glu Ile Arg Glu Thr Leu Thr
                180                 185                 190

Arg Arg Tyr Lys Phe Ala Ile Arg Arg Leu Ala Gln Thr Asn Ser Glu
                195                 200                 205

Asp Val Phe Ser Leu Ala Met Thr Ala Phe Ala Arg Glu Ile Asp Pro
210                 215                 220

His Thr Asn Tyr Leu Ser Pro Arg Asn Thr Glu Gln Phe Asn Thr Glu
225                 230                 235                 240

Met Ser Leu Ser Leu Glu Gly Ile Gly Ala Val Leu Gln Met Asp Asp
                245                 250                 255

Asp Tyr Thr Val Ile Asn Ser Met Val Ala Gly Gly Pro Ala Ala Lys
                260                 265                 270

Ser Lys Ala Ile Ser Val Gly Asp Lys Ile Val Gly Val Gly Gln Thr
                275                 280                 285

Gly Lys Pro Met Val Asp Val Ile Gly Trp Arg Leu Asp Asp Val Val
                290                 295                 300

Ala Leu Ile Lys Gly Pro Lys Gly Ser Lys Val Arg Leu Glu Ile Leu
305                 310                 315                 320

Pro Ala Gly Lys Gly Thr Lys Thr Arg Thr Val Thr Leu Thr Arg Glu
                325                 330                 335

Arg Ile Arg Leu Glu Asp Arg Ala Val Lys Met Ser Val Lys Thr Val
                340                 345                 350

Gly Lys Glu Lys Val Gly Val Leu Asp Ile Pro Gly Phe Tyr Val Gly
                355                 360                 365

Leu Thr Asp Asp Val Lys Val Gln Leu Gln Lys Leu Glu Lys Gln Asn
                370                 375                 380

Val Ser Ser Val Ile Ile Asp Leu Arg Ser Asn Gly Gly Gly Ala Leu
385                 390                 395                 400

Thr Glu Ala Val Ser Leu Ser Gly Leu Phe Ile Pro Ala Gly Pro Ile
                405                 410                 415

Val Gln Val Arg Asp Asn Asn Gly Lys Val Arg Glu Asp Ser Asp Thr
                420                 425                 430

Asp Gly Gln Val Phe Tyr Lys Gly Pro Leu Val Val Leu Val Asp Arg
                435                 440                 445

Phe Ser Ala Ser Ala Ser Glu Ile Phe Ala Ala Ala Met Gln Asp Tyr
                450                 455                 460

Gly Arg Ala Leu Val Val Gly Glu Pro Thr Phe Gly Lys Gly Thr Val
465                 470                 475                 480

Gln Gln Tyr Arg Ser Leu Asn Arg Ile Tyr Asp Gln Met Leu Arg Pro
                485                 490                 495

Glu Trp Pro Ala Leu Gly Ser Val Gln Tyr Thr Ile Gln Lys Phe Tyr
                500                 505                 510
```

```
Arg Val Asn Gly Gly Ser Thr Gln Arg Lys Gly Val Thr Pro Asp Ile
            515                 520                 525

Ile Met Pro Thr Gly Asn Glu Glu Thr Glu Thr Gly Glu Lys Phe Glu
        530                 535                 540

Asp Asn Ala Leu Pro Trp Asp Ser Ile Asp Ala Ala Thr Tyr Val Lys
545                 550                 555                 560

Ser Gly Asp Leu Thr Ala Phe Glu Pro Glu Leu Leu Lys Glu His Asn
                565                 570                 575

Ala Arg Ile Ala Lys Asp Pro Glu Phe Gln Asn Ile Met Lys Asp Ile
                580                 585                 590

Ala Arg Phe Asn Ala Met Lys Asp Lys Arg Asn Ile Val Ser Leu Asn
            595                 600                 605

Tyr Ala Val Arg Glu Lys Glu Asn Asn Glu Asp Ala Thr Arg Leu
        610                 615                 620

Ala Arg Leu Asn Glu Arg Phe Lys Arg Glu Gly Lys Pro Glu Leu Lys
625                 630                 635                 640

Lys Leu Asp Asp Leu Pro Lys Asp Tyr Gln Glu Pro Asp Pro Tyr Leu
                645                 650                 655

Asp Glu Thr Val Asn Ile Ala Leu Asp Leu Ala Lys Leu Glu Lys Ala
                660                 665                 670

Arg Pro Ala Glu Gln Pro Ala Pro Val Lys
        675                 680

<210> SEQ ID NO 27
<211> LENGTH: 236
<212> TYPE: PRT
<213> ORGANISM: Escherichia coli
<300> PUBLICATION INFORMATION:
<308> DATABASE ACCESSION NUMBER: NCBI Reference Sequence / AP_003452
<309> DATABASE ENTRY DATE: 2011-06-21
<313> RELEVANT RESIDUES IN SEQ ID NO: (1)..(236)

<400> SEQUENCE: 27

Met Lys Lys Gly Phe Met Leu Phe Thr Leu Leu Ala Ala Phe Ser Gly
1               5                   10                  15

Phe Ala Gln Ala Asp Asp Ala Ala Ile Gln Gln Thr Leu Ala Lys Met
            20                  25                  30

Gly Ile Lys Ser Ser Asp Ile Gln Pro Ala Pro Val Ala Gly Met Lys
        35                  40                  45

Thr Val Leu Thr Asn Ser Gly Val Leu Tyr Ile Thr Asp Asp Gly Lys
    50                  55                  60

His Ile Ile Gln Gly Pro Met Tyr Asp Val Ser Gly Thr Ala Pro Val
65                  70                  75                  80

Asn Val Thr Asn Lys Met Leu Leu Lys Gln Leu Asn Ala Leu Glu Lys
                85                  90                  95

Glu Met Ile Val Tyr Lys Ala Pro Gln Glu Lys His Val Ile Thr Val
            100                 105                 110

Phe Thr Asp Ile Thr Cys Gly Tyr Cys His Lys Leu His Glu Gln Met
        115                 120                 125

Ala Asp Tyr Asn Ala Leu Gly Ile Thr Val Arg Tyr Leu Ala Phe Pro
    130                 135                 140

Arg Gln Gly Leu Asp Ser Asp Ala Glu Lys Glu Met Lys Ala Ile Trp
145                 150                 155                 160

Cys Ala Lys Asp Lys Asn Lys Ala Phe Asp Asp Val Met Ala Gly Lys
                165                 170                 175
```

Ser Val Ala Pro Ala Ser Cys Asp Val Asp Ile Ala Asp His Tyr Ala
         180                 185                 190

Leu Gly Val Gln Leu Gly Val Ser Gly Thr Pro Ala Val Val Leu Ser
         195                 200                 205

Asn Gly Thr Leu Val Pro Gly Tyr Gln Pro Pro Lys Glu Met Lys Glu
         210                 215                 220

Phe Leu Asp Glu His Gln Lys Met Thr Ser Gly Lys
225                 230                 235

<210> SEQ ID NO 28
<211> LENGTH: 2048
<212> TYPE: DNA
<213> ORGANISM: Artificial Sequence
<220> FEATURE:
<223> OTHER INFORMATION: knockout mutated Tsp gene

<400> SEQUENCE: 28

| | | | | | |
|---|---|---|---|---|---|
| atgaattcgt | ttttaggctt | accgcgttag | ctggcctgct | tgcaatagca | ggccagacat | 60 |
| taattgtaga | agatatcacg | cgtgctgatc | aaattccggt | attaaaggaa | gagacgcagc | 120 |
| atgcgacggt | aagtgagcgc | gtaacgtcgc | gcttcacccg | ttctcattat | cgccagttcg | 180 |
| acctcgatca | ggcattttcg | gccaaaatct | ttgaccgcta | cctgaatctg | ctcgattaca | 240 |
| gccacaacgt | gctgctggca | agcgatgttg | aacagttcgc | gaaaaagaaa | accgagttag | 300 |
| gcgatgaact | gcgttcaggc | aaactcgacg | ttttctacga | tctctacaat | ctggcgcaaa | 360 |
| agcgccgttt | tgagcgttac | cagtacgctt | tgtcggtact | ggaaaagccg | atggatttca | 420 |
| ccggcaacga | cacttataac | cttgaccgca | gcaaagcgcc | ctggccgaaa | acgaggctg | 480 |
| agttgaacgc | gctgtgggac | agtaaagtca | aattcgacga | gttaagcctg | aagctgacag | 540 |
| gaaaaacgga | taagaaatt | cgtgaaaccc | tgactcgccg | ctacaaattt | gccattcgtc | 600 |
| gtctggcgca | aaccaacagc | gaagatgttt | tctcgctggc | aatgacggcg | tttgcgcgtg | 660 |
| aaatcgaccc | gcataccaac | tatctttccc | cgcgtaatac | cgaacagttc | aacactgaaa | 720 |
| tgagtttgtc | gctggaaggt | attggcgcag | tgctgcaaat | ggatgatgac | tacaccgtta | 780 |
| tcaattcgat | ggtggcaggt | ggtccggcag | cgaagagtaa | agctatcagc | gttggtgaca | 840 |
| aaattgtcgg | tgttggtcaa | acaggcaagc | cgatggttga | cgtgattggc | tggcgtcttg | 900 |
| atgatgtggt | tgccttaatt | aaagggccga | agggcagtaa | agttcgtctg | gaaattttac | 960 |
| ctgctggtaa | agggaccaag | acccgtactg | taacgttgac | ccgtgaacgt | attcgtctcg | 1020 |
| aagaccgcgc | ggttaaaatg | tcggtgaaga | ccgtcggtaa | agagaaagtc | ggcgtgctgg | 1080 |
| atattccggg | cttctatgtg | ggtttgacag | acgatgtcaa | agtgcaactg | cagaaactgg | 1140 |
| aaaaacagaa | tgtcagcagc | gtcatcatcg | acctgcgtag | caatggcggt | ggggcgttaa | 1200 |
| ctgaagccgt | atcgctctcc | ggtctgtttt | ttcctgcggg | tcccattgtt | caggtccgcg | 1260 |
| ataacaacgg | caaggttcgt | gaagatagcg | ataccgacgg | acaggttttc | tataaaggcc | 1320 |
| cgctggtggt | gctggttgac | cgcttcagtg | cttcggcttc | agaaatcttt | gccgcggcaa | 1380 |
| tgcaggatta | cggtcgtgcg | ctggttgtgg | gtgaaccgac | gtttggtaaa | ggcaccgttc | 1440 |
| agcaataccg | ttcattgaac | cgtatttacg | atcagatgtt | acgtcctgaa | tggcagcgc | 1500 |
| tgggttctgt | gcagtacacg | atccagaaat | tctatcgcgt | taacggcggc | agtacgcaac | 1560 |
| gtaaaggcgt | aacgccagac | atcatcatgc | cgacgggtaa | tgaagaaacg | gaaacgggtg | 1620 |
| agaaattcga | agataacgcg | ctgccgtggg | atagcattga | tgccgcgact | tatgtgaaat | 1680 |
| caggagattt | aacggccttt | gaaccggagc | tgctgaagga | acataatgcg | cgtatcgcga | 1740 |

-continued

```
aagatcctga gttccagaac atcatgaagg atatcgcgcg cttcaacgct atgaaggaca    1800
agcgcaatat cgtttctctg aattacgctg tgcgtgagaa agagaataat gaagatgatg    1860
cgacgcgtct ggcgcgtttg aacgaacgct ttaaacgcga aggtaaaccg gagttgaaga    1920
aactggatga tctaccgaaa gattaccagg agccggatcc ttatctggat gagacggtga    1980
atatcgcact cgatctggcg aagcttgaaa agccagacc cgcggaacaa cccgctcccg    2040
tcaagtaa                                                              2048
```

<210> SEQ ID NO 29
<211> LENGTH: 1425
<212> TYPE: DNA
<213> ORGANISM: Escherichia coli
<220> FEATURE:
<221> NAME/KEY: CDS
<222> LOCATION: (1)..(1425)

<400> SEQUENCE: 29

| | | | | | | | | | | | | | | | |
|---|---|---|---|---|---|---|---|---|---|---|---|---|---|---|---|
| atg | aaa | aaa | acc | aca | tta | gca | ctg | agt | gca | ctg | gct | ctg | agt | tta | ggt | 48 |
| Met | Lys | Lys | Thr | Thr | Leu | Ala | Leu | Ser | Ala | Leu | Ala | Leu | Ser | Leu | Gly | |
| 1 | | | | 5 | | | | | 10 | | | | | 15 | | |

| ttg | gcg | tta | tct | ccg | ctc | tct | gca | acg | gcg | gct | gag | act | tct | tca | gca | 96 |
| Leu | Ala | Leu | Ser | Pro | Leu | Ser | Ala | Thr | Ala | Ala | Glu | Thr | Ser | Ser | Ala | |
| | | | 20 | | | | | 25 | | | | | 30 | | | |

| acg | aca | gcc | cag | cag | atg | cca | agc | ctt | gca | ccg | atg | ctc | gaa | aag | gtg | 144 |
| Thr | Thr | Ala | Gln | Gln | Met | Pro | Ser | Leu | Ala | Pro | Met | Leu | Glu | Lys | Val | |
| | | 35 | | | | | 40 | | | | | 45 | | | | |

| atg | cct | tca | gtg | gtc | agc | att | aac | gta | gaa | ggt | agc | aca | acc | gtt | aat | 192 |
| Met | Pro | Ser | Val | Val | Ser | Ile | Asn | Val | Glu | Gly | Ser | Thr | Thr | Val | Asn | |
| | 50 | | | | | 55 | | | | | 60 | | | | | |

| acg | ccg | cgt | atg | ccg | cgt | aat | ttc | cag | cag | ttc | ttc | ggt | gat | gat | tct | 240 |
| Thr | Pro | Arg | Met | Pro | Arg | Asn | Phe | Gln | Gln | Phe | Phe | Gly | Asp | Asp | Ser | |
| 65 | | | | | 70 | | | | | 75 | | | | | 80 | |

| ccg | ttc | tgc | cag | gaa | ggt | tct | ccg | ttc | cag | agc | tct | ccg | ttc | tgc | cag | 288 |
| Pro | Phe | Cys | Gln | Glu | Gly | Ser | Pro | Phe | Gln | Ser | Ser | Pro | Phe | Cys | Gln | |
| | | | | 85 | | | | | 90 | | | | | 95 | | |

| ggt | ggc | cag | ggc | ggt | aat | ggt | ggc | ggc | cag | caa | cag | aaa | ttc | atg | gcg | 336 |
| Gly | Gly | Gln | Gly | Gly | Asn | Gly | Gly | Gly | Gln | Gln | Gln | Lys | Phe | Met | Ala | |
| | | | 100 | | | | | 105 | | | | | 110 | | | |

| ctg | ggt | tcc | ggc | gtc | atc | att | gat | gcc | gat | aaa | ggc | tat | gtc | gtc | acc | 384 |
| Leu | Gly | Ser | Gly | Val | Ile | Ile | Asp | Ala | Asp | Lys | Gly | Tyr | Val | Val | Thr | |
| | | 115 | | | | | 120 | | | | | 125 | | | | |

| aac | aac | cac | gtt | gtt | gat | aac | gcg | acg | gtc | att | aaa | gtt | caa | ctg | agc | 432 |
| Asn | Asn | His | Val | Val | Asp | Asn | Ala | Thr | Val | Ile | Lys | Val | Gln | Leu | Ser | |
| | 130 | | | | | 135 | | | | | 140 | | | | | |

| gat | ggc | cgt | aag | ttc | gac | gcg | aag | atg | gtt | ggc | aaa | gat | ccg | cgc | tct | 480 |
| Asp | Gly | Arg | Lys | Phe | Asp | Ala | Lys | Met | Val | Gly | Lys | Asp | Pro | Arg | Ser | |
| 145 | | | | | 150 | | | | | 155 | | | | | 160 | |

| gat | atc | gcg | ctg | atc | caa | atc | cag | aac | ccg | aaa | aac | ctg | acc | gca | att | 528 |
| Asp | Ile | Ala | Leu | Ile | Gln | Ile | Gln | Asn | Pro | Lys | Asn | Leu | Thr | Ala | Ile | |
| | | | | 165 | | | | | 170 | | | | | 175 | | |

| aag | atg | gcg | gat | tct | gat | gca | ctg | cgc | gtg | ggt | gat | tac | acc | gta | gcg | 576 |
| Lys | Met | Ala | Asp | Ser | Asp | Ala | Leu | Arg | Val | Gly | Asp | Tyr | Thr | Val | Ala | |
| | | | 180 | | | | | 185 | | | | | 190 | | | |

| att | ggt | aac | ccg | ttt | ggt | ctg | ggc | gag | acg | gta | act | tcc | ggg | att | gtc | 624 |
| Ile | Gly | Asn | Pro | Phe | Gly | Leu | Gly | Glu | Thr | Val | Thr | Ser | Gly | Ile | Val | |
| | | 195 | | | | | 200 | | | | | 205 | | | | |

| tct | gcg | ctg | ggg | cgt | agc | ggc | ctg | aat | gcc | gaa | aac | tac | gaa | aac | ttc | 672 |
| Ser | Ala | Leu | Gly | Arg | Ser | Gly | Leu | Asn | Ala | Glu | Asn | Tyr | Glu | Asn | Phe | |
| | 210 | | | | | 215 | | | | | 220 | | | | | |

```
atc cag acc gat gca gcg atc aac cgt ggt aac tcc ggt ggt gcg ctg    720
Ile Gln Thr Asp Ala Ala Ile Asn Arg Gly Asn Ser Gly Gly Ala Leu
225                 230                 235                 240 gtt aac ctg aac ggc gaa ctg atc ggt atc aac acc gcg atc ctc gca    768
Val Asn Leu Asn Gly Glu Leu Ile Gly Ile Asn Thr Ala Ile Leu Ala
            245                 250                 255 ccg gac ggc ggc aac atc ggt atc ggt ttt gct atc ccg agt aac atg    816
Pro Asp Gly Gly Asn Ile Gly Ile Gly Phe Ala Ile Pro Ser Asn Met
        260                 265                 270 gtg aaa aac ctg acc tcg cag atg gtg gaa tac ggc cag gtg aaa cgc    864
Val Lys Asn Leu Thr Ser Gln Met Val Glu Tyr Gly Gln Val Lys Arg
    275                 280                 285 ggt gag ctg ggt att atg ggg act gag ctg aac tcc gaa ctg gcg aaa    912
Gly Glu Leu Gly Ile Met Gly Thr Glu Leu Asn Ser Glu Leu Ala Lys
290                 295                 300 gcg atg aaa gtt gac gcc cag cgc ggt gct ttc gta agc cag gtt ctg    960
Ala Met Lys Val Asp Ala Gln Arg Gly Ala Phe Val Ser Gln Val Leu
305                 310                 315                 320 cct aat tcc tcc gct gca aaa gcg ggc att aaa gcg ggt gat gtg atc    1008
Pro Asn Ser Ser Ala Ala Lys Ala Gly Ile Lys Ala Gly Asp Val Ile
            325                 330                 335 acc tca ctg aac ggt aag ccg atc agc agc ttt gcc gca ctg cgt gct    1056
Thr Ser Leu Asn Gly Lys Pro Ile Ser Ser Phe Ala Ala Leu Arg Ala
        340                 345                 350 cag gtg ggt act atg ccg gta ggc agc aaa ctg acc ctg ggc tta ctg    1104
Gln Val Gly Thr Met Pro Val Gly Ser Lys Leu Thr Leu Gly Leu Leu
    355                 360                 365 cgc gac ggt aag cag gtt aac gtg aac ctg gaa ctg cag cag agc agc    1152
Arg Asp Gly Lys Gln Val Asn Val Asn Leu Glu Leu Gln Gln Ser Ser
370                 375                 380 cag aat cag gtt gat tcc agc tcc atc ttc aac ggc att gaa ggc gct    1200
Gln Asn Gln Val Asp Ser Ser Ser Ile Phe Asn Gly Ile Glu Gly Ala
385                 390                 395                 400 gag atg agc aac aaa ggc aaa gat cag ggc gtg gta gtg aac aac gtg    1248
Glu Met Ser Asn Lys Gly Lys Asp Gln Gly Val Val Val Asn Asn Val
            405                 410                 415 aaa acg ggc act ccg gct gcg cag atc ggc ctg aag aaa ggt gat gtg    1296
Lys Thr Gly Thr Pro Ala Ala Gln Ile Gly Leu Lys Lys Gly Asp Val
        420                 425                 430 att att ggc gcg aac cag cag gca gtg aaa aac atc gct gaa ctg cgt    1344
Ile Ile Gly Ala Asn Gln Gln Ala Val Lys Asn Ile Ala Glu Leu Arg
    435                 440                 445 aaa gtt ctc gac agc aaa ccg tct gtg ctg gca ctc aac att cag cgc    1392
Lys Val Leu Asp Ser Lys Pro Ser Val Leu Ala Leu Asn Ile Gln Arg
450                 455                 460 ggc gac agc acc atc tac ctg tta atg cag taa                        1425
Gly Asp Ser Thr Ile Tyr Leu Leu Met Gln
465                 470

<210> SEQ ID NO 30
<211> LENGTH: 474
<212> TYPE: PRT
<213> ORGANISM: Escherichia coli

<400> SEQUENCE: 30

Met Lys Lys Thr Thr Leu Ala Leu Ser Ala Leu Ala Leu Ser Leu Gly
1               5                   10                  15

Leu Ala Leu Ser Pro Leu Ser Ala Thr Ala Ala Glu Thr Ser Ser Ala
            20                  25                  30
```

```
Thr Thr Ala Gln Gln Met Pro Ser Leu Ala Pro Met Leu Glu Lys Val
         35                  40                  45

Met Pro Ser Val Val Ser Ile Asn Val Glu Gly Ser Thr Thr Val Asn
 50                  55                  60

Thr Pro Arg Met Pro Arg Asn Phe Gln Gln Phe Phe Gly Asp Asp Ser
 65                  70                  75                  80

Pro Phe Cys Gln Glu Gly Ser Pro Phe Gln Ser Ser Pro Phe Cys Gln
                 85                  90                  95

Gly Gly Gln Gly Gly Asn Gly Gly Gln Gln Gln Lys Phe Met Ala
             100                 105                 110

Leu Gly Ser Gly Val Ile Ile Asp Ala Asp Lys Gly Tyr Val Val Thr
             115                 120                 125

Asn Asn His Val Val Asp Asn Ala Thr Val Ile Lys Val Gln Leu Ser
         130                 135                 140

Asp Gly Arg Lys Phe Asp Ala Lys Met Val Gly Lys Asp Pro Arg Ser
145                 150                 155                 160

Asp Ile Ala Leu Ile Gln Ile Gln Asn Pro Lys Asn Leu Thr Ala Ile
                 165                 170                 175

Lys Met Ala Asp Ser Asp Ala Leu Arg Val Gly Asp Tyr Thr Val Ala
             180                 185                 190

Ile Gly Asn Pro Phe Gly Leu Gly Glu Thr Val Thr Ser Gly Ile Val
             195                 200                 205

Ser Ala Leu Gly Arg Ser Gly Leu Asn Ala Glu Asn Tyr Glu Asn Phe
210                 215                 220

Ile Gln Thr Asp Ala Ala Ile Asn Arg Gly Asn Ser Gly Gly Ala Leu
225                 230                 235                 240

Val Asn Leu Asn Gly Glu Leu Ile Gly Ile Asn Thr Ala Ile Leu Ala
             245                 250                 255

Pro Asp Gly Gly Asn Ile Gly Ile Gly Phe Ala Ile Pro Ser Asn Met
             260                 265                 270

Val Lys Asn Leu Thr Ser Gln Met Val Glu Tyr Gly Gln Val Lys Arg
             275                 280                 285

Gly Glu Leu Gly Ile Met Gly Thr Glu Leu Asn Ser Glu Leu Ala Lys
             290                 295                 300

Ala Met Lys Val Asp Ala Gln Arg Gly Ala Phe Val Ser Gln Val Leu
305                 310                 315                 320

Pro Asn Ser Ser Ala Ala Lys Ala Gly Ile Lys Ala Gly Asp Val Ile
                 325                 330                 335

Thr Ser Leu Asn Gly Lys Pro Ile Ser Ser Phe Ala Ala Leu Arg Ala
             340                 345                 350

Gln Val Gly Thr Met Pro Val Gly Ser Lys Leu Thr Leu Gly Leu Leu
             355                 360                 365

Arg Asp Gly Lys Gln Val Asn Val Asn Leu Glu Leu Gln Gln Ser Ser
         370                 375                 380

Gln Asn Gln Val Asp Ser Ser Ile Phe Asn Gly Ile Glu Gly Ala
385                 390                 395                 400

Glu Met Ser Asn Lys Gly Lys Asp Gln Gly Val Val Asn Asn Val
                 405                 410                 415

Lys Thr Gly Thr Pro Ala Ala Gln Ile Gly Leu Lys Lys Gly Asp Val
             420                 425                 430

Ile Ile Gly Ala Asn Gln Gln Ala Val Lys Asn Ile Ala Glu Leu Arg
             435                 440                 445

Lys Val Leu Asp Ser Lys Pro Ser Val Leu Ala Leu Asn Ile Gln Arg
```

```
                        450                 455                 460
Gly Asp Ser Thr Ile Tyr Leu Leu Met Gln
465                 470

<210> SEQ ID NO 31
<211> LENGTH: 1425
<212> TYPE: DNA
<213> ORGANISM: Artificial Sequence
<220> FEATURE:
<223> OTHER INFORMATION: mutated DegP gene comprising the mutation S210A
      and an Ase I restriction marker
<220> FEATURE:
<221> NAME/KEY: CDS
<222> LOCATION: (1)..(1425)

<400> SEQUENCE: 31 atg aaa aaa acc aca tta gca ctg agt gca ctg gct ctg agt tta ggt       48
Met Lys Lys Thr Thr Leu Ala Leu Ser Ala Leu Ala Leu Ser Leu Gly
1               5                   10                  15 ttg gcg tta tct ccg ctc tct gca acg gcg gct gag act tct tca gca       96
Leu Ala Leu Ser Pro Leu Ser Ala Thr Ala Ala Glu Thr Ser Ser Ala
                20                  25                  30 acg aca gcc cag cag atg cca agc ctt gca ccg atg ctc gaa aag gtg      144
Thr Thr Ala Gln Gln Met Pro Ser Leu Ala Pro Met Leu Glu Lys Val
            35                  40                  45 atg cct tca gtg gtc agc att aac gta gaa ggt agc aca acc gtt aat      192
Met Pro Ser Val Val Ser Ile Asn Val Glu Gly Ser Thr Thr Val Asn
        50                  55                  60 acg ccg cgt atg ccg cgt aat ttc cag cag ttc ttc ggt gat gat tct      240
Thr Pro Arg Met Pro Arg Asn Phe Gln Gln Phe Phe Gly Asp Asp Ser
65                  70                  75                  80 ccg ttc tgc cag gaa ggt tct ccg ttc cag agc tct ccg ttc tgc cag      288
Pro Phe Cys Gln Glu Gly Ser Pro Phe Gln Ser Ser Pro Phe Cys Gln
                85                  90                  95 ggc ggc cag ggc ggt aat ggt ggc ggc cag caa cag aaa ttc atg gcg      336
Gly Gly Gln Gly Gly Asn Gly Gly Gly Gln Gln Gln Lys Phe Met Ala
            100                 105                 110 ctg ggt tcc ggc gtc atc att gat gcc gat aaa ggc tat gtc gtc acc      384
Leu Gly Ser Gly Val Ile Ile Asp Ala Asp Lys Gly Tyr Val Val Thr
        115                 120                 125 aac aac cac gtt gtt gat aac gcg acg gtc att aaa gtt caa ctg agc      432
Asn Asn His Val Val Asp Asn Ala Thr Val Ile Lys Val Gln Leu Ser
    130                 135                 140 gat ggc cgt aag ttc gac gcg aag atg gtt ggc aaa gat ccg cgc tct      480
Asp Gly Arg Lys Phe Asp Ala Lys Met Val Gly Lys Asp Pro Arg Ser
145                 150                 155                 160 gat atc gcg ctg atc caa atc cag aac ccg aaa aac ctg acc gca att      528
Asp Ile Ala Leu Ile Gln Ile Gln Asn Pro Lys Asn Leu Thr Ala Ile
                165                 170                 175 aag atg gcg gat tct gat gca ctg cgc gtg ggt gat tac acc gta gcg      576
Lys Met Ala Asp Ser Asp Ala Leu Arg Val Gly Asp Tyr Thr Val Ala
            180                 185                 190 att ggt aac ccg ttt ggt ctg ggc gag acg gta act tcc ggg att gtc      624
Ile Gly Asn Pro Phe Gly Leu Gly Glu Thr Val Thr Ser Gly Ile Val
        195                 200                 205 tct gcg ctg ggg cgt agc ggc ctg aat gcc gaa aac tac gaa aac ttc      672
Ser Ala Leu Gly Arg Ser Gly Leu Asn Ala Glu Asn Tyr Glu Asn Phe
    210                 215                 220 atc cag acc gat gca gcg att aat cgt ggt aac gcc ggt ggt gcg ctg      720
Ile Gln Thr Asp Ala Ala Ile Asn Arg Gly Asn Ala Gly Gly Ala Leu
225                 230                 235                 240
```

```
gtt aac ctg aac ggc gaa ctg atc ggt atc aac acc gcg atc ctc gca    768
Val Asn Leu Asn Gly Glu Leu Ile Gly Ile Asn Thr Ala Ile Leu Ala
            245                 250                 255 ccg gac ggc ggc aac atc ggt atc ggt ttt gct atc ccg agt aac atg    816
Pro Asp Gly Gly Asn Ile Gly Ile Gly Phe Ala Ile Pro Ser Asn Met
        260                 265                 270 gtg aaa aac ctg acc tcg cag atg gtg gaa tac ggc cag gtg aaa cgc    864
Val Lys Asn Leu Thr Ser Gln Met Val Glu Tyr Gly Gln Val Lys Arg
    275                 280                 285 ggt gag ctg ggt att atg ggg act gag ctg aac tcc gaa ctg gcg aaa    912
Gly Glu Leu Gly Ile Met Gly Thr Glu Leu Asn Ser Glu Leu Ala Lys
290                 295                 300 gcg atg aaa gtt gac gcc cag cgc ggt gct ttc gta agc cag gtt ctg    960
Ala Met Lys Val Asp Ala Gln Arg Gly Ala Phe Val Ser Gln Val Leu
305                 310                 315                 320 cct aat tcc tcc gct gca aaa gcg ggc att aaa gcg ggt gat gtg atc   1008
Pro Asn Ser Ser Ala Ala Lys Ala Gly Ile Lys Ala Gly Asp Val Ile
            325                 330                 335 acc tca ctg aac ggt aag ccg atc agc agc ttt gcc gca ctg cgt gct   1056
Thr Ser Leu Asn Gly Lys Pro Ile Ser Ser Phe Ala Ala Leu Arg Ala
        340                 345                 350 cag gtg ggt act atg ccg gta ggc agc aaa ctg acc ctg ggc tta ctg   1104
Gln Val Gly Thr Met Pro Val Gly Ser Lys Leu Thr Leu Gly Leu Leu
    355                 360                 365 cgc gac ggt aag cag gtt aac gtg aac ctg gaa ctg cag cag agc agc   1152
Arg Asp Gly Lys Gln Val Asn Val Asn Leu Glu Leu Gln Gln Ser Ser
370                 375                 380 cag aat cag gtt gat tcc agc tcc atc ttc aac ggc att gaa ggc gct   1200
Gln Asn Gln Val Asp Ser Ser Ser Ile Phe Asn Gly Ile Glu Gly Ala
385                 390                 395                 400 gag atg agc aac aaa ggc aaa gat cag ggc gtg gta gtg aac aac gtg   1248
Glu Met Ser Asn Lys Gly Lys Asp Gln Gly Val Val Val Asn Asn Val
            405                 410                 415 aaa acg ggc act ccg gct gcg cag atc ggc ctg aag aaa ggt gat gtg   1296
Lys Thr Gly Thr Pro Ala Ala Gln Ile Gly Leu Lys Lys Gly Asp Val
        420                 425                 430 att att ggc gcg aac cag cag gca gtg aaa aac atc gct gaa ctg cgt   1344
Ile Ile Gly Ala Asn Gln Gln Ala Val Lys Asn Ile Ala Glu Leu Arg
    435                 440                 445 aaa gtt ctc gac agc aaa ccg tct gtg ctg gca ctc aac att cag cgc   1392
Lys Val Leu Asp Ser Lys Pro Ser Val Leu Ala Leu Asn Ile Gln Arg
450                 455                 460 ggc gac agc acc atc tac ctg tta atg cag taa                        1425
Gly Asp Ser Thr Ile Tyr Leu Leu Met Gln
465                 470

<210> SEQ ID NO 32
<211> LENGTH: 474
<212> TYPE: PRT
<213> ORGANISM: Artificial Sequence
<220> FEATURE:
<223> OTHER INFORMATION: Synthetic Construct

<400> SEQUENCE: 32

Met Lys Lys Thr Thr Leu Ala Leu Ser Ala Leu Ala Leu Ser Leu Gly
1               5                   10                  15

Leu Ala Leu Ser Pro Leu Ser Ala Thr Ala Ala Glu Thr Ser Ser Ala
            20                  25                  30

Thr Thr Ala Gln Gln Met Pro Ser Leu Ala Pro Met Leu Glu Lys Val
        35                  40                  45
```

```
Met Pro Ser Val Val Ser Ile Asn Val Glu Gly Ser Thr Thr Val Asn
 50                  55                  60

Thr Pro Arg Met Pro Arg Asn Phe Gln Gln Phe Phe Gly Asp Asp Ser
 65                  70                  75                  80

Pro Phe Cys Gln Glu Gly Ser Pro Phe Gln Ser Ser Pro Phe Cys Gln
                 85                  90                  95

Gly Gly Gln Gly Gly Asn Gly Gly Gln Gln Gln Lys Phe Met Ala
                100                 105                 110

Leu Gly Ser Gly Val Ile Ile Asp Ala Asp Lys Gly Tyr Val Val Thr
            115                 120                 125

Asn Asn His Val Val Asp Asn Ala Thr Val Ile Lys Val Gln Leu Ser
            130                 135                 140

Asp Gly Arg Lys Phe Asp Ala Lys Met Val Gly Lys Asp Pro Arg Ser
145                 150                 155                 160

Asp Ile Ala Leu Ile Gln Ile Gln Asn Pro Lys Asn Leu Thr Ala Ile
                165                 170                 175

Lys Met Ala Asp Ser Asp Ala Leu Arg Val Gly Asp Tyr Thr Val Ala
            180                 185                 190

Ile Gly Asn Pro Phe Gly Leu Gly Glu Thr Val Thr Ser Gly Ile Val
            195                 200                 205

Ser Ala Leu Gly Arg Ser Gly Leu Asn Ala Glu Asn Tyr Glu Asn Phe
210                 215                 220

Ile Gln Thr Asp Ala Ala Ile Asn Arg Gly Asn Ala Gly Gly Ala Leu
225                 230                 235                 240

Val Asn Leu Asn Gly Glu Leu Ile Gly Ile Asn Thr Ala Ile Leu Ala
            245                 250                 255

Pro Asp Gly Gly Asn Ile Gly Ile Gly Phe Ala Ile Pro Ser Asn Met
            260                 265                 270

Val Lys Asn Leu Thr Ser Gln Met Val Glu Tyr Gly Gln Val Lys Arg
            275                 280                 285

Gly Glu Leu Gly Ile Met Gly Thr Glu Leu Asn Ser Glu Leu Ala Lys
            290                 295                 300

Ala Met Lys Val Asp Ala Gln Arg Gly Ala Phe Val Ser Gln Val Leu
305                 310                 315                 320

Pro Asn Ser Ser Ala Ala Lys Ala Gly Ile Lys Ala Gly Asp Val Ile
                325                 330                 335

Thr Ser Leu Asn Gly Lys Pro Ile Ser Ser Phe Ala Ala Leu Arg Ala
            340                 345                 350

Gln Val Gly Thr Met Pro Val Gly Ser Lys Leu Thr Leu Gly Leu Leu
            355                 360                 365

Arg Asp Gly Lys Gln Val Asn Val Asn Leu Glu Leu Gln Gln Ser Ser
370                 375                 380

Gln Asn Gln Val Asp Ser Ser Ile Phe Asn Gly Ile Glu Gly Ala
385                 390                 395                 400

Glu Met Ser Asn Lys Gly Lys Asp Gln Gly Val Val Val Asn Asn Val
                405                 410                 415

Lys Thr Gly Thr Pro Ala Ala Gln Ile Gly Leu Lys Lys Gly Asp Val
            420                 425                 430

Ile Ile Gly Ala Asn Gln Gln Ala Val Lys Asn Ile Ala Glu Leu Arg
            435                 440                 445

Lys Val Leu Asp Ser Lys Pro Ser Val Leu Ala Leu Asn Ile Gln Arg
450                 455                 460

Gly Asp Ser Thr Ile Tyr Leu Leu Met Gln
```

-continued

```
<210> SEQ ID NO 33
<211> LENGTH: 67
<212> TYPE: DNA
<213> ORGANISM: Artificial Sequence
<220> FEATURE:
<223> OTHER INFORMATION: IGS cassette-1

<400> SEQUENCE: 33
gagctcacca gtaacaaaaa gttttaatag aggagagtgt taatgaagaa gactgctata        60
gcaattg                                                                 67

<210> SEQ ID NO 34
<211> LENGTH: 69
<212> TYPE: DNA
<213> ORGANISM: Artificial Sequence
<220> FEATURE:
<223> OTHER INFORMATION: IGS cassette-2

<400> SEQUENCE: 34
gagctcacca gtaacaaaaa gttttaatag aggggagtgt taaaatgaag aagactgcta        60
tagcaattg                                                               69

<210> SEQ ID NO 35
<211> LENGTH: 81
<212> TYPE: DNA
<213> ORGANISM: Artificial Sequence
<220> FEATURE:
<223> OTHER INFORMATION: IGS cassette-3

<400> SEQUENCE: 35
gagctcacca gtaacaaaaa gctttaatag aggagagtgt tgaggaggaa aaaaaatga         60 agaaaactgc tatagcaatt g                                                 81

<210> SEQ ID NO 36
<211> LENGTH: 81
<212> TYPE: DNA
<213> ORGANISM: Artificial Sequence
<220> FEATURE:
<223> OTHER INFORMATION: IGS cassette-4

<400> SEQUENCE: 36
gagctcacca gtaacaaaaa gttttaatag aggagagtgt tgacgaggat tatataatga        60
agaaaactgc tatagcaatt g                                                 81

<210> SEQ ID NO 37
<211> LENGTH: 954
<212> TYPE: DNA
<213> ORGANISM: Escherichia coli
<220> FEATURE:
<221> NAME/KEY: CDS
<222> LOCATION: (1)..(954)

<400> SEQUENCE: 37 atg cgg gcg aaa ctt ctg gga ata gtc ctg aca acc cct att gcg atc         48
Met Arg Ala Lys Leu Leu Gly Ile Val Leu Thr Thr Pro Ile Ala Ile
1               5                   10                  15 agc tct ttt gct tct acc gag act tta tcg ttt act cct gac aac ata         96
Ser Ser Phe Ala Ser Thr Glu Thr Leu Ser Phe Thr Pro Asp Asn Ile
            20                  25                  30 aat gcg gac att agt ctt gga act ctg agc gga aaa aca aaa gag cgt        144
Asn Ala Asp Ile Ser Leu Gly Thr Leu Ser Gly Lys Thr Lys Glu Arg
```

| | | |
|---|---|---|
| gtt tat cta gcc gaa gaa gga ggc cga aaa gtc agt caa ctc gac tgg<br>Val Tyr Leu Ala Glu Glu Gly Gly Arg Lys Val Ser Gln Leu Asp Trp<br>50                           55                       60 | 192 |
| aaa ttc aat aac gct gca att att aaa ggt gca att aat tgg gat ttg<br>Lys Phe Asn Asn Ala Ala Ile Ile Lys Gly Ala Ile Asn Trp Asp Leu<br>65                      70                       75                     80 | 240 |
| atg ccc cag ata tct atc ggg gct gct ggc tgg aca act ctc ggc agc<br>Met Pro Gln Ile Ser Ile Gly Ala Ala Gly Trp Thr Thr Leu Gly Ser<br>                       85                         90                     95 | 288 |
| cga ggt ggc aat atg gtc gat cag gac tgg atg gat tcc agt aac ccc<br>Arg Gly Gly Asn Met Val Asp Gln Asp Trp Met Asp Ser Ser Asn Pro<br>                100                     105                     110 | 336 |
| gga acc tgg acg gat gaa agt aga cac cct gat aca caa ctc aat tat<br>Gly Thr Trp Thr Asp Glu Ser Arg His Pro Asp Thr Gln Leu Asn Tyr<br>115                      120                     125 | 384 |
| gcc aac gaa ttt gat ctg aat atc aaa ggc tgg ctc ctc aac gaa ccc<br>Ala Asn Glu Phe Asp Leu Asn Ile Lys Gly Trp Leu Leu Asn Glu Pro<br>130                      135                     140 | 432 |
| aat tac cgc ctg gga ctc atg gcc gga tat cag gaa agc cgt tat agc<br>Asn Tyr Arg Leu Gly Leu Met Ala Gly Tyr Gln Glu Ser Arg Tyr Ser<br>145                      150                     155                     160 | 480 |
| ttt aca gcc aga ggt ggt tcc tat atc tac agt tct gag gag gga ttc<br>Phe Thr Ala Arg Gly Gly Ser Tyr Ile Tyr Ser Ser Glu Glu Gly Phe<br>                165                     170                     175 | 528 |
| aga gat gat atc ggc tcc ttc ccg aat gga gaa aga gca atc ggc tac<br>Arg Asp Asp Ile Gly Ser Phe Pro Asn Gly Glu Arg Ala Ile Gly Tyr<br>                180                     185                     190 | 576 |
| aaa caa cgt ttt aaa atg ccc tac att ggc ttg act gga agt tat cgt<br>Lys Gln Arg Phe Lys Met Pro Tyr Ile Gly Leu Thr Gly Ser Tyr Arg<br>                195                     200                     205 | 624 |
| tat gaa gat ttt gaa ctc ggt ggc aca ttt aaa tac agc ggc tgg gtg<br>Tyr Glu Asp Phe Glu Leu Gly Gly Thr Phe Lys Tyr Ser Gly Trp Val<br>210                      215                     220 | 672 |
| gaa tca tct gat aac gat gaa cac tat gac ccg gga aaa aga atc act<br>Glu Ser Ser Asp Asn Asp Glu His Tyr Asp Pro Gly Lys Arg Ile Thr<br>225                      230                     235                     240 | 720 |
| tat cgc agt aag gtc aaa gac caa aat tac tat tct gtt gca gtc aat<br>Tyr Arg Ser Lys Val Lys Asp Gln Asn Tyr Tyr Ser Val Ala Val Asn<br>                       245                     250                     255 | 768 |
| gca ggt tat tac gtc aca cct aac gca aaa gtt tat gtt gaa ggc gca<br>Ala Gly Tyr Tyr Val Thr Pro Asn Ala Lys Val Tyr Val Glu Gly Ala<br>                260                     265                     270 | 816 |
| tgg aat cgg gtt acg aat aaa aaa ggt aat act tca ctt tat gat cac<br>Trp Asn Arg Val Thr Asn Lys Lys Gly Asn Thr Ser Leu Tyr Asp His<br>                275                     280                     285 | 864 |
| aat aat aac act tca gac tac agc aaa aat gga gca ggt ata gaa aac<br>Asn Asn Asn Thr Ser Asp Tyr Ser Lys Asn Gly Ala Gly Ile Glu Asn<br>290                      295                     300 | 912 |
| tat aac ttc atc act act gct ggt ctt aag tac aca ttt taa<br>Tyr Asn Phe Ile Thr Thr Ala Gly Leu Lys Tyr Thr Phe<br>305                      310                     315 | 954 |

<210> SEQ ID NO 38
<211> LENGTH: 317
<212> TYPE: PRT
<213> ORGANISM: Escherichia coli

<400> SEQUENCE: 38

Met Arg Ala Lys Leu Leu Gly Ile Val Leu Thr Thr Pro Ile Ala Ile

```
  1               5                   10                  15
Ser Ser Phe Ala Ser Thr Glu Thr Leu Ser Phe Thr Pro Asp Asn Ile
                 20                  25                  30

Asn Ala Asp Ile Ser Leu Gly Thr Leu Ser Gly Lys Thr Lys Glu Arg
                 35                  40                  45

Val Tyr Leu Ala Glu Glu Gly Arg Lys Val Ser Gln Leu Asp Trp
 50                  55                  60

Lys Phe Asn Asn Ala Ala Ile Ile Lys Gly Ala Ile Asn Trp Asp Leu
 65                  70                  75                  80

Met Pro Gln Ile Ser Ile Gly Ala Ala Gly Trp Thr Thr Leu Gly Ser
                 85                  90                  95

Arg Gly Gly Asn Met Val Asp Gln Asp Trp Met Asp Ser Ser Asn Pro
                100                 105                 110

Gly Thr Trp Thr Asp Glu Ser Arg His Pro Asp Thr Gln Leu Asn Tyr
                115                 120                 125

Ala Asn Glu Phe Asp Leu Asn Ile Lys Gly Trp Leu Leu Asn Glu Pro
130                 135                 140

Asn Tyr Arg Leu Gly Leu Met Ala Gly Tyr Gln Glu Ser Arg Tyr Ser
145                 150                 155                 160

Phe Thr Ala Arg Gly Gly Ser Tyr Ile Tyr Ser Ser Glu Glu Gly Phe
                165                 170                 175

Arg Asp Asp Ile Gly Ser Phe Pro Asn Gly Glu Arg Ala Ile Gly Tyr
                180                 185                 190

Lys Gln Arg Phe Lys Met Pro Tyr Ile Gly Leu Thr Gly Ser Tyr Arg
                195                 200                 205

Tyr Glu Asp Phe Glu Leu Gly Gly Thr Phe Lys Tyr Ser Gly Trp Val
210                 215                 220

Glu Ser Ser Asp Asn Asp Glu His Tyr Asp Pro Gly Lys Arg Ile Thr
225                 230                 235                 240

Tyr Arg Ser Lys Val Lys Asp Gln Asn Tyr Tyr Ser Val Ala Val Asn
                245                 250                 255

Ala Gly Tyr Tyr Val Thr Pro Asn Ala Lys Val Tyr Val Glu Gly Ala
                260                 265                 270

Trp Asn Arg Val Thr Asn Lys Lys Gly Asn Thr Ser Leu Tyr Asp His
                275                 280                 285

Asn Asn Asn Thr Ser Asp Tyr Ser Lys Asn Gly Ala Gly Ile Glu Asn
                290                 295                 300

Tyr Asn Phe Ile Thr Thr Ala Gly Leu Lys Tyr Thr Phe
305                 310                 315
```

<210> SEQ ID NO 39
<211> LENGTH: 954
<212> TYPE: DNA
<213> ORGANISM: Artificial Sequence
<220> FEATURE:
<223> OTHER INFORMATION: knock-out mutant OmpT gene
<220> FEATURE:
<221> NAME/KEY: CDS
<222> LOCATION: (1)..(954)

<400> SEQUENCE: 39

```
att cgg gcg aaa ctt ctg gga ata gtc ctg aca acc cct att gcg atc    48
Ile Arg Ala Lys Leu Leu Gly Ile Val Leu Thr Thr Pro Ile Ala Ile
 1               5                  10                  15 agc tct ttt gct tct acc gag act tta tcg ttt act cct gac aac ata    96
Ser Ser Phe Ala Ser Thr Glu Thr Leu Ser Phe Thr Pro Asp Asn Ile
                 20                  25                  30
```

```
aat gcg gac att agt ctt gga act ctg agc gga aaa aca aaa gag cgt      144
Asn Ala Asp Ile Ser Leu Gly Thr Leu Ser Gly Lys Thr Lys Glu Arg
        35                  40                  45 gtt tat cta gcc gaa gaa gga ggc cga aaa gtc agt caa ctc gac tgg      192
Val Tyr Leu Ala Glu Glu Gly Gly Arg Lys Val Ser Gln Leu Asp Trp
 50                  55                  60 aaa ttc aat aac gct gca att att aaa ggt gca att aat tgg gat ttg      240
Lys Phe Asn Asn Ala Ala Ile Ile Lys Gly Ala Ile Asn Trp Asp Leu
 65                  70                  75                  80 atg ccc cag ata tct atc ggg gct gct ggc tgg aca act ctc ggc agc      288
Met Pro Gln Ile Ser Ile Gly Ala Ala Gly Trp Thr Thr Leu Gly Ser
                 85                  90                  95 cga ggt ggc aat atg gtc gat cag gac tgg atg gat tcc agt aac ccc      336
Arg Gly Gly Asn Met Val Asp Gln Asp Trp Met Asp Ser Ser Asn Pro
            100                 105                 110 gga acc tgg acg gat gaa agt aga cac cct gat aca caa ctc aat tat      384
Gly Thr Trp Thr Asp Glu Ser Arg His Pro Asp Thr Gln Leu Asn Tyr
        115                 120                 125 gcc aac gaa ttt gat ctg aat atc aaa ggc tgg ctc ctc aac gaa ccc      432
Ala Asn Glu Phe Asp Leu Asn Ile Lys Gly Trp Leu Leu Asn Glu Pro
130                 135                 140 aat tac cgc ctg gga ctc atg gcc gga tat cag gaa agc cgt tat agc      480
Asn Tyr Arg Leu Gly Leu Met Ala Gly Tyr Gln Glu Ser Arg Tyr Ser
145                 150                 155                 160 ttt aca gcc aga ggt ggt tcc tat atc tac agt tct gag gag gga ttc      528
Phe Thr Ala Arg Gly Gly Ser Tyr Ile Tyr Ser Ser Glu Glu Gly Phe
                165                 170                 175 aga gat gat atc ggc tcc ttc ccg aat gga gaa aga gca atc ggc tac      576
Arg Asp Asp Ile Gly Ser Phe Pro Asn Gly Glu Arg Ala Ile Gly Tyr
            180                 185                 190 aaa caa cgt ttt aaa atg ccc tac att ggc ttg act gga agt tat cgt      624
Lys Gln Arg Phe Lys Met Pro Tyr Ile Gly Leu Thr Gly Ser Tyr Arg
        195                 200                 205 tat gaa gat ttt gaa ctc ggt ggc aca ttt aaa tac agc ggc tgg gtg      672
Tyr Glu Asp Phe Glu Leu Gly Gly Thr Phe Lys Tyr Ser Gly Trp Val
210                 215                 220 gaa tca tct gat aac gat gaa cac tat gac ccg gga aaa aga atc act      720
Glu Ser Ser Asp Asn Asp Glu His Tyr Asp Pro Gly Lys Arg Ile Thr
225                 230                 235                 240 tat cgc agt aag gtc aaa gac caa aat tac tat tct gtt gca gtc aat      768
Tyr Arg Ser Lys Val Lys Asp Gln Asn Tyr Tyr Ser Val Ala Val Asn
                245                 250                 255 gca ggt tat tac gtc aca cct aac gca aaa gtt tat gtt gaa ggc gca      816
Ala Gly Tyr Tyr Val Thr Pro Asn Ala Lys Val Tyr Val Glu Gly Ala
            260                 265                 270 tgg aat cgg gtt acg aat aaa aaa ggt aat act tca ctt tat gat cac      864
Trp Asn Arg Val Thr Asn Lys Lys Gly Asn Thr Ser Leu Tyr Asp His
        275                 280                 285 aat aat aac act tca gac tac agc aaa aat gga gca ggt ata gaa aac      912
Asn Asn Asn Thr Ser Asp Tyr Ser Lys Asn Gly Ala Gly Ile Glu Asn
290                 295                 300 tat aac ttc atc act act gct ggt ctt aag tac aca ttt taa             954
Tyr Asn Phe Ile Thr Thr Ala Gly Leu Lys Tyr Thr Phe
305                 310                 315

<210> SEQ ID NO 40
<211> LENGTH: 317
<212> TYPE: PRT
<213> ORGANISM: Artificial Sequence
<220> FEATURE:
```

<223> OTHER INFORMATION: Synthetic Construct

<400> SEQUENCE: 40

Ile Arg Ala Lys Leu Leu Gly Ile Val Leu Thr Thr Pro Ile Ala Ile
1               5                   10                  15

Ser Ser Phe Ala Ser Thr Glu Thr Leu Ser Phe Thr Pro Asp Asn Ile
            20                  25                  30

Asn Ala Asp Ile Ser Leu Gly Thr Leu Ser Gly Lys Thr Lys Glu Arg
        35                  40                  45

Val Tyr Leu Ala Glu Glu Gly Arg Lys Val Ser Gln Leu Asp Trp
    50                  55                  60

Lys Phe Asn Asn Ala Ala Ile Ile Lys Gly Ala Ile Asn Trp Asp Leu
65                  70                  75                  80

Met Pro Gln Ile Ser Ile Gly Ala Ala Gly Trp Thr Thr Leu Gly Ser
                85                  90                  95

Arg Gly Gly Asn Met Val Asp Gln Asp Trp Met Asp Ser Ser Asn Pro
                100                 105                 110

Gly Thr Trp Thr Asp Glu Ser Arg His Pro Asp Thr Gln Leu Asn Tyr
            115                 120                 125

Ala Asn Glu Phe Asp Leu Asn Ile Lys Gly Trp Leu Leu Asn Glu Pro
        130                 135                 140

Asn Tyr Arg Leu Gly Leu Met Ala Gly Tyr Gln Glu Ser Arg Tyr Ser
145                 150                 155                 160

Phe Thr Ala Arg Gly Gly Ser Tyr Ile Tyr Ser Ser Glu Glu Gly Phe
                165                 170                 175

Arg Asp Asp Ile Gly Ser Phe Pro Asn Gly Glu Arg Ala Ile Gly Tyr
            180                 185                 190

Lys Gln Arg Phe Lys Met Pro Tyr Ile Gly Leu Thr Gly Ser Tyr Arg
        195                 200                 205

Tyr Glu Asp Phe Glu Leu Gly Gly Thr Phe Lys Tyr Ser Gly Trp Val
    210                 215                 220

Glu Ser Ser Asp Asn Asp Glu His Tyr Asp Pro Gly Lys Arg Ile Thr
225                 230                 235                 240

Tyr Arg Ser Lys Val Lys Asp Gln Asn Tyr Tyr Ser Val Ala Val Asn
                245                 250                 255

Ala Gly Tyr Tyr Val Thr Pro Asn Ala Lys Val Tyr Val Glu Gly Ala
            260                 265                 270

Trp Asn Arg Val Thr Asn Lys Lys Gly Asn Thr Ser Leu Tyr Asp His
        275                 280                 285

Asn Asn Asn Thr Ser Asp Tyr Ser Lys Asn Gly Ala Gly Ile Glu Asn
    290                 295                 300

Tyr Asn Phe Ile Thr Thr Ala Gly Leu Lys Tyr Thr Phe
305                 310                 315

<210> SEQ ID NO 41
<211> LENGTH: 954
<212> TYPE: DNA
<213> ORGANISM: Artificial Sequence
<220> FEATURE:
<223> OTHER INFORMATION: mutated OmpT gene encoding the protein with the
      point mutations D210A and H212A
<220> FEATURE:
<221> NAME/KEY: CDS
<222> LOCATION: (1)..(954)

<400> SEQUENCE: 41 atg cgg gcg aaa ctt ctg gga ata gtc ctg aca acc cct att gcg atc        48

```
            Met Arg Ala Lys Leu Leu Gly Ile Val Leu Thr Thr Pro Ile Ala Ile
            1               5                   10                  15 agc tct ttt gct tct acc gag act tta tcg ttt act cct gac aac ata         96
Ser Ser Phe Ala Ser Thr Glu Thr Leu Ser Phe Thr Pro Asp Asn Ile
            20                  25                  30 aat gcg gac att agt ctt gga act ctg agc gga aaa aca aaa gag cgt        144
Asn Ala Asp Ile Ser Leu Gly Thr Leu Ser Gly Lys Thr Lys Glu Arg
            35                  40                  45 gtt tat cta gcc gaa gaa gga ggc cga aaa gtc agt caa ctc gac tgg        192
Val Tyr Leu Ala Glu Glu Gly Gly Arg Lys Val Ser Gln Leu Asp Trp
50                  55                  60 aaa ttc aat aac gct gca att att aaa ggt gca att aat tgg gat ttg        240
Lys Phe Asn Asn Ala Ala Ile Ile Lys Gly Ala Ile Asn Trp Asp Leu
65                  70                  75                  80 atg ccc cag ata tct atc ggg gct gct ggc tgg aca act ctc ggc agc        288
Met Pro Gln Ile Ser Ile Gly Ala Ala Gly Trp Thr Thr Leu Gly Ser
            85                  90                  95 cga ggt ggc aat atg gtc gat cag gac tgg atg gat tcc agt aac ccc        336
Arg Gly Gly Asn Met Val Asp Gln Asp Trp Met Asp Ser Ser Asn Pro
            100                 105                 110 gga acc tgg acg gat gaa agt aga cac cct gat aca caa ctc aat tat        384
Gly Thr Trp Thr Asp Glu Ser Arg His Pro Asp Thr Gln Leu Asn Tyr
            115                 120                 125 gcc aac gaa ttt gat ctg aat atc aaa ggc tgg ctc ctc aac gaa ccc        432
Ala Asn Glu Phe Asp Leu Asn Ile Lys Gly Trp Leu Leu Asn Glu Pro
130                 135                 140 aat tac cgc ctg gga ctc atg gcc gga tat cag gaa agc cgt tat agc        480
Asn Tyr Arg Leu Gly Leu Met Ala Gly Tyr Gln Glu Ser Arg Tyr Ser
145                 150                 155                 160 ttt aca gcc aga ggt ggt tcc tat atc tac agt tct gag gag gga ttc        528
Phe Thr Ala Arg Gly Gly Ser Tyr Ile Tyr Ser Ser Glu Glu Gly Phe
            165                 170                 175 aga gat gat atc ggc tcc ttc ccg aat gga gaa aga gca atc ggc tac        576
Arg Asp Asp Ile Gly Ser Phe Pro Asn Gly Glu Arg Ala Ile Gly Tyr
            180                 185                 190 aaa caa cgt ttt aaa atg ccc tac att ggc ttg act gga agt tat cgt        624
Lys Gln Arg Phe Lys Met Pro Tyr Ile Gly Leu Thr Gly Ser Tyr Arg
            195                 200                 205 tat gaa gat ttt gaa ctc ggt ggc aca ttt aaa tac agc ggc tgg gtg        672
Tyr Glu Asp Phe Glu Leu Gly Gly Thr Phe Lys Tyr Ser Gly Trp Val
210                 215                 220 gaa tca tct gat aac gct gaa gct tat gac ccg gga aaa aga atc act        720
Glu Ser Ser Asp Asn Ala Glu Ala Tyr Asp Pro Gly Lys Arg Ile Thr
225                 230                 235                 240 tat cgc agt aag gtc aaa gac caa aat tac tat tct gtt gca gtc aat        768
Tyr Arg Ser Lys Val Lys Asp Gln Asn Tyr Tyr Ser Val Ala Val Asn
            245                 250                 255 gca ggt tat tac gtc aca cct aac gca aaa gtt tat gtt gaa ggc gca        816
Ala Gly Tyr Tyr Val Thr Pro Asn Ala Lys Val Tyr Val Glu Gly Ala
            260                 265                 270 tgg aat cgg gtt acg aat aaa aaa ggt aat act tca ctt tat gat cac        864
Trp Asn Arg Val Thr Asn Lys Lys Gly Asn Thr Ser Leu Tyr Asp His
            275                 280                 285 aat aat aac act tca gac tac agc aaa aat gga gca ggt ata gaa aac        912
Asn Asn Asn Thr Ser Asp Tyr Ser Lys Asn Gly Ala Gly Ile Glu Asn
            290                 295                 300 tat aac ttc atc act act gct ggt ctt aag tac aca ttt taa                954
Tyr Asn Phe Ile Thr Thr Ala Gly Leu Lys Tyr Thr Phe
305                 310                 315
```

<210> SEQ ID NO 42
<211> LENGTH: 317
<212> TYPE: PRT
<213> ORGANISM: Artificial Sequence
<220> FEATURE:
<223> OTHER INFORMATION: Synthetic Construct

<400> SEQUENCE: 42

Met Arg Ala Lys Leu Leu Gly Ile Val Leu Thr Thr Pro Ile Ala Ile
1               5                   10                  15

Ser Ser Phe Ala Ser Thr Glu Thr Leu Ser Phe Thr Pro Asp Asn Ile
            20                  25                  30

Asn Ala Asp Ile Ser Leu Gly Thr Leu Ser Gly Lys Thr Lys Glu Arg
        35                  40                  45

Val Tyr Leu Ala Glu Glu Gly Gly Arg Lys Val Ser Gln Leu Asp Trp
    50                  55                  60

Lys Phe Asn Asn Ala Ala Ile Ile Lys Gly Ala Ile Asn Trp Asp Leu
65                  70                  75                  80

Met Pro Gln Ile Ser Ile Gly Ala Ala Gly Trp Thr Thr Leu Gly Ser
                85                  90                  95

Arg Gly Gly Asn Met Val Asp Gln Asp Trp Met Asp Ser Ser Asn Pro
            100                 105                 110

Gly Thr Trp Thr Asp Glu Ser Arg His Pro Asp Thr Gln Leu Asn Tyr
        115                 120                 125

Ala Asn Glu Phe Asp Leu Asn Ile Lys Gly Trp Leu Leu Asn Glu Pro
    130                 135                 140

Asn Tyr Arg Leu Gly Leu Met Ala Gly Tyr Gln Glu Ser Arg Tyr Ser
145                 150                 155                 160

Phe Thr Ala Arg Gly Gly Ser Tyr Ile Tyr Ser Ser Glu Glu Gly Phe
                165                 170                 175

Arg Asp Asp Ile Gly Ser Phe Pro Asn Gly Glu Arg Ala Ile Gly Tyr
            180                 185                 190

Lys Gln Arg Phe Lys Met Pro Tyr Ile Gly Leu Thr Gly Ser Tyr Arg
        195                 200                 205

Tyr Glu Asp Phe Glu Leu Gly Gly Thr Phe Lys Tyr Ser Gly Trp Val
    210                 215                 220

Glu Ser Ser Asp Asn Ala Glu Ala Tyr Asp Pro Gly Lys Arg Ile Thr
225                 230                 235                 240

Tyr Arg Ser Lys Val Lys Asp Gln Asn Tyr Tyr Ser Val Ala Val Asn
                245                 250                 255

Ala Gly Tyr Tyr Val Thr Pro Asn Ala Lys Val Tyr Val Glu Gly Ala
            260                 265                 270

Trp Asn Arg Val Thr Asn Lys Lys Gly Asn Thr Ser Leu Tyr Asp His
        275                 280                 285

Asn Asn Asn Thr Ser Asp Tyr Ser Lys Asn Gly Ala Gly Ile Glu Asn
    290                 295                 300

Tyr Asn Phe Ile Thr Thr Ala Gly Leu Lys Tyr Thr Phe
305                 310                 315

<210> SEQ ID NO 43
<211> LENGTH: 711
<212> TYPE: DNA
<213> ORGANISM: Escherichia coli
<220> FEATURE:
<221> NAME/KEY: CDS
<222> LOCATION: (1)..(711)

```
<400> SEQUENCE: 43 atg aag aaa ggt ttt atg ttg ttt act ttg tta gcg gcg ttt tca ggc      48
Met Lys Lys Gly Phe Met Leu Phe Thr Leu Leu Ala Ala Phe Ser Gly
1               5                   10                  15 ttt gct cag gct gat gac gcg gca att caa caa acg tta gcc aaa atg      96
Phe Ala Gln Ala Asp Asp Ala Ala Ile Gln Gln Thr Leu Ala Lys Met
            20                  25                  30 ggc atc aaa agc agc gat att cag ccc gcg cct gta gct ggc atg aag     144
Gly Ile Lys Ser Ser Asp Ile Gln Pro Ala Pro Val Ala Gly Met Lys
        35                  40                  45 aca gtt ctg act aac agc ggc gtg ttg tac atc acc gat gat ggt aaa     192
Thr Val Leu Thr Asn Ser Gly Val Leu Tyr Ile Thr Asp Asp Gly Lys
    50                  55                  60 cat atc att cag ggg cca atg tat gac gtt agt ggc acg gct ccg gtc     240
His Ile Ile Gln Gly Pro Met Tyr Asp Val Ser Gly Thr Ala Pro Val
65                  70                  75                  80 aat gtc acc aat aag atg ctg tta aag cag ttg aat gcg ctt gaa aaa     288
Asn Val Thr Asn Lys Met Leu Leu Lys Gln Leu Asn Ala Leu Glu Lys
                85                  90                  95 gag atg atc gtt tat aaa gcg ccg cag gaa aaa cac gtc atc acc gtg     336
Glu Met Ile Val Tyr Lys Ala Pro Gln Glu Lys His Val Ile Thr Val
            100                 105                 110 ttt act gat att acc tgt ggt tac tgc cac aaa ctg cat gag caa atg     384
Phe Thr Asp Ile Thr Cys Gly Tyr Cys His Lys Leu His Glu Gln Met
        115                 120                 125 gca gac tac aac gcg ctg ggg atc acc gtg cgt tat ctt gct ttc ccg     432
Ala Asp Tyr Asn Ala Leu Gly Ile Thr Val Arg Tyr Leu Ala Phe Pro
    130                 135                 140 cgc cag ggg ctg gac agc gat gca gag aaa gaa atg aaa gct atc tgg     480
Arg Gln Gly Leu Asp Ser Asp Ala Glu Lys Glu Met Lys Ala Ile Trp
145                 150                 155                 160 tgt gcg aaa gat aaa aac aaa gcg ttt gat gat gtg atg gca ggt aaa     528
Cys Ala Lys Asp Lys Asn Lys Ala Phe Asp Asp Val Met Ala Gly Lys
                165                 170                 175 agc gtc gca cca gcc agt tgc gac gtg gat att gcc gac cat tac gca     576
Ser Val Ala Pro Ala Ser Cys Asp Val Asp Ile Ala Asp His Tyr Ala
            180                 185                 190 ctt ggc gtc cag ctt ggc gtt agc ggt act ccg gca gtt gtg ctg agc     624
Leu Gly Val Gln Leu Gly Val Ser Gly Thr Pro Ala Val Val Leu Ser
        195                 200                 205 aat ggc aca ctt gtt ccg ggt tac cag ccg ccg aaa gag atg aaa gaa     672
Asn Gly Thr Leu Val Pro Gly Tyr Gln Pro Pro Lys Glu Met Lys Glu
    210                 215                 220 ttt ctc gac gaa cac caa aaa atg acc agc ggt aaa taa                 711
Phe Leu Asp Glu His Gln Lys Met Thr Ser Gly Lys
225                 230                 235

<210> SEQ ID NO 44
<211> LENGTH: 236
<212> TYPE: PRT
<213> ORGANISM: Escherichia coli

<400> SEQUENCE: 44

Met Lys Lys Gly Phe Met Leu Phe Thr Leu Leu Ala Ala Phe Ser Gly
1               5                   10                  15

Phe Ala Gln Ala Asp Asp Ala Ala Ile Gln Gln Thr Leu Ala Lys Met
            20                  25                  30

Gly Ile Lys Ser Ser Asp Ile Gln Pro Ala Pro Val Ala Gly Met Lys
        35                  40                  45
```

```
Thr Val Leu Thr Asn Ser Gly Val Leu Tyr Ile Thr Asp Asp Gly Lys
 50                  55                  60

His Ile Ile Gln Gly Pro Met Tyr Asp Val Ser Gly Thr Ala Pro Val
 65                  70                  75                  80

Asn Val Thr Asn Lys Met Leu Leu Lys Gln Leu Asn Ala Leu Glu Lys
                 85                  90                  95

Glu Met Ile Val Tyr Lys Ala Pro Gln Glu Lys His Val Ile Thr Val
            100                 105                 110

Phe Thr Asp Ile Thr Cys Gly Tyr Cys His Lys Leu His Glu Gln Met
        115                 120                 125

Ala Asp Tyr Asn Ala Leu Gly Ile Thr Val Arg Tyr Leu Ala Phe Pro
130                 135                 140

Arg Gln Gly Leu Asp Ser Asp Ala Glu Lys Glu Met Lys Ala Ile Trp
145                 150                 155                 160

Cys Ala Lys Asp Lys Asn Lys Ala Phe Asp Asp Val Met Ala Gly Lys
                165                 170                 175

Ser Val Ala Pro Ala Ser Cys Asp Val Asp Ile Ala Asp His Tyr Ala
            180                 185                 190

Leu Gly Val Gln Leu Gly Val Ser Gly Thr Pro Ala Val Val Leu Ser
        195                 200                 205

Asn Gly Thr Leu Val Pro Gly Tyr Gln Pro Pro Lys Glu Met Lys Glu
210                 215                 220

Phe Leu Asp Glu His Gln Lys Met Thr Ser Gly Lys
225                 230                 235

<210> SEQ ID NO 45
<211> LENGTH: 729
<212> TYPE: DNA
<213> ORGANISM: Artificial Sequence
<220> FEATURE:
<223> OTHER INFORMATION: DsbC comprising his-tag and lacking an EcoRI
      restriction site
<220> FEATURE:
<221> NAME/KEY: CDS
<222> LOCATION: (1)..(729)

<400> SEQUENCE: 45 atg aag aaa ggt ttt atg ttg ttt act ttg tta gcg gcg ttt tca ggc      48
Met Lys Lys Gly Phe Met Leu Phe Thr Leu Leu Ala Ala Phe Ser Gly
 1               5                  10                  15 ttt gct cag gct gat gac gcg gca att caa caa acg tta gcc aaa atg      96
Phe Ala Gln Ala Asp Asp Ala Ala Ile Gln Gln Thr Leu Ala Lys Met
            20                  25                  30 ggc atc aaa agc agc gat att cag ccc gcg cct gta gct ggc atg aag     144
Gly Ile Lys Ser Ser Asp Ile Gln Pro Ala Pro Val Ala Gly Met Lys
        35                  40                  45 aca gtt ctg act aac agc ggc gtg ttg tac atc acc gat gat ggt aaa     192
Thr Val Leu Thr Asn Ser Gly Val Leu Tyr Ile Thr Asp Asp Gly Lys
 50                  55                  60 cat atc att cag ggg cca atg tat gac gtt agt ggc acg gct ccg gtc     240
His Ile Ile Gln Gly Pro Met Tyr Asp Val Ser Gly Thr Ala Pro Val
 65                  70                  75                  80 aat gtc acc aat aag atg ctg tta aag cag ttg aat gcg ctt gaa aaa     288
Asn Val Thr Asn Lys Met Leu Leu Lys Gln Leu Asn Ala Leu Glu Lys
                 85                  90                  95 gag atg atc gtt tat aaa gcg ccg cag gaa aaa cac gtc atc acc gtg     336
Glu Met Ile Val Tyr Lys Ala Pro Gln Glu Lys His Val Ile Thr Val
            100                 105                 110 ttt act gat att acc tgt ggt tac tgc cac aaa ctg cat gag caa atg     384
Phe Thr Asp Ile Thr Cys Gly Tyr Cys His Lys Leu His Glu Gln Met
```

```
                Phe Thr Asp Ile Thr Cys Gly Tyr Cys His Lys Leu His Glu Gln Met
                                115                 120                 125 gca gac tac aac gcg ctg ggg atc acc gtg cgt tat ctt gct ttc ccg         432
Ala Asp Tyr Asn Ala Leu Gly Ile Thr Val Arg Tyr Leu Ala Phe Pro
        130                 135                 140 cgc cag ggg ctg gac agc gat gca gag aaa gaa atg aaa gct atc tgg         480
Arg Gln Gly Leu Asp Ser Asp Ala Glu Lys Glu Met Lys Ala Ile Trp
145                 150                 155                 160 tgt gcg aaa gat aaa aac aaa gcg ttt gat gat gtg atg gca ggt aaa         528
Cys Ala Lys Asp Lys Asn Lys Ala Phe Asp Asp Val Met Ala Gly Lys
                165                 170                 175 agc gtc gca cca gcc agt tgc gac gtg gat att gcc gac cat tac gca         576
Ser Val Ala Pro Ala Ser Cys Asp Val Asp Ile Ala Asp His Tyr Ala
            180                 185                 190 ctt ggc gtc cag ctt ggc gtt agc ggt act ccg gca gtt gtg ctg agc         624
Leu Gly Val Gln Leu Gly Val Ser Gly Thr Pro Ala Val Val Leu Ser
        195                 200                 205 aat ggc aca ctt gtt ccg ggt tac cag ccg ccg aaa gag atg aaa gaa         672
Asn Gly Thr Leu Val Pro Gly Tyr Gln Pro Pro Lys Glu Met Lys Glu
210                 215                 220 ttt ctc gac gaa cac caa aaa atg acc agc ggt aaa cac cat cac cat         720
Phe Leu Asp Glu His Gln Lys Met Thr Ser Gly Lys His His His His
225                 230                 235                 240 cac cac taa                                                             729
His His <210> SEQ ID NO 46
<211> LENGTH: 242
<212> TYPE: PRT
<213> ORGANISM: Artificial Sequence
<220> FEATURE:
<223> OTHER INFORMATION: Synthetic Construct

<400> SEQUENCE: 46

Met Lys Lys Gly Phe Met Leu Phe Thr Leu Leu Ala Ala Phe Ser Gly
1               5                   10                  15

Phe Ala Gln Ala Asp Asp Ala Ala Ile Gln Gln Thr Leu Ala Lys Met
                20                  25                  30

Gly Ile Lys Ser Ser Asp Ile Gln Pro Ala Pro Val Ala Gly Met Lys
            35                  40                  45

Thr Val Leu Thr Asn Ser Gly Val Leu Tyr Ile Thr Asp Asp Gly Lys
        50                  55                  60

His Ile Ile Gln Gly Pro Met Tyr Asp Val Ser Gly Thr Ala Pro Val
65                  70                  75                  80

Asn Val Thr Asn Lys Met Leu Leu Lys Gln Leu Asn Ala Leu Glu Lys
                85                  90                  95

Glu Met Ile Val Tyr Lys Ala Pro Gln Glu Lys His Val Ile Thr Val
                100                 105                 110

Phe Thr Asp Ile Thr Cys Gly Tyr Cys His Lys Leu His Glu Gln Met
            115                 120                 125

Ala Asp Tyr Asn Ala Leu Gly Ile Thr Val Arg Tyr Leu Ala Phe Pro
        130                 135                 140

Arg Gln Gly Leu Asp Ser Asp Ala Glu Lys Glu Met Lys Ala Ile Trp
145                 150                 155                 160

Cys Ala Lys Asp Lys Asn Lys Ala Phe Asp Asp Val Met Ala Gly Lys
                165                 170                 175

Ser Val Ala Pro Ala Ser Cys Asp Val Asp Ile Ala Asp His Tyr Ala
            180                 185                 190
```

```
Leu Gly Val Gln Leu Gly Val Ser Gly Thr Pro Ala Val Val Leu Ser
        195                 200                 205

Asn Gly Thr Leu Val Pro Gly Tyr Gln Pro Pro Lys Glu Met Lys Glu
    210                 215                 220

Phe Leu Asp Glu His Gln Lys Met Thr Ser Gly Lys His His His His
225                 230                 235                 240

His His

<210> SEQ ID NO 47
<211> LENGTH: 24
<212> TYPE: DNA
<213> ORGANISM: Artificial Sequence
<220> FEATURE:
<223> OTHER INFORMATION: Primer 6283 Tsp 3'

<400> SEQUENCE: 47
gcatcataat tttctttta cctc                                              24

<210> SEQ ID NO 48
<211> LENGTH: 24
<212> TYPE: DNA
<213> ORGANISM: Artificial Sequence
<220> FEATURE:
<223> OTHER INFORMATION: Primer 6283 Tsp 5'

<400> SEQUENCE: 48
gggaaatgaa cctgagcaaa acgc                                             24

<210> SEQ ID NO 49
<211> LENGTH: 3120
<212> TYPE: DNA
<213> ORGANISM: Escherichia coli
<220> FEATURE:
<221> NAME/KEY: CDS
<222> LOCATION: (206)..(3091)
<223> OTHER INFORMATION: preprotease III (AA -23 to 939)
<220> FEATURE:
<221> NAME/KEY: sig_peptide
<222> LOCATION: (206)..(274)
<220> FEATURE:
<221> NAME/KEY: mat_peptide
<222> LOCATION: (275)..(3091)
<223> OTHER INFORMATION: protease III (AA 1 - 939)
<300> PUBLICATION INFORMATION:
<308> DATABASE ACCESSION NUMBER: GenBank / X06227
<309> DATABASE ENTRY DATE: 2005-04-18
<313> RELEVANT RESIDUES IN SEQ ID NO: (1)..(3120)

<400> SEQUENCE: 49
ttaccgctgt ttcgctttaa tcagtcatga gtgctgtata aaaattgcgc aatctatccg      60
cttactttat gatgcgcacc agtcacggac tgatggttat ataaacatag gctgactcct     120
gcagcacaag attaaattct ggcagatgat ttgcgttaac gtgttgaatc tggacagaaa     180
attaagttga ttatgaggtc cgtga atg ccc cgc agc acc tgg ttc aaa gca      232
                              Met Pro Arg Ser Thr Trp Phe Lys Ala
                                  -20                 -15 tta ttg ttg tta gtt gcc ctt tgg gca ccc tta agt cag gca gaa acg       280
Leu Leu Leu Leu Val Ala Leu Trp Ala Pro Leu Ser Gln Ala Glu Thr
        -10                 -5              -1  1 gga tgg cag ccg att cag gaa acc atc cgt aaa agt gat aaa gat aac       328
Gly Trp Gln Pro Ile Gln Glu Thr Ile Arg Lys Ser Asp Lys Asp Asn
    5                   10                  15 cgc cag tat cag gct ata cgt ctg gat aac ggt atg gtg gtc ttg ctg       376
Arg Gln Tyr Gln Ala Ile Arg Leu Asp Asn Gly Met Val Val Leu Leu
```

```
              20                  25                  30
gtt tct gat ccg cag gca gtt aaa tcg ctc tcg gcg ctg gtg gtg ccc      424
Val Ser Asp Pro Gln Ala Val Lys Ser Leu Ser Ala Leu Val Val Pro
 35                  40                  45                  50 gtt ggg tcg ctg gaa gat ccc gag gcg tac cag ggg ctg gca cat tac      472
Val Gly Ser Leu Glu Asp Pro Glu Ala Tyr Gln Gly Leu Ala His Tyr
                     55                  60                  65 ctt gaa cat atg agt ctg atg ggg tcg aaa aag tac ccg cag gct gac      520
Leu Glu His Met Ser Leu Met Gly Ser Lys Lys Tyr Pro Gln Ala Asp
         70                  75                  80 agt ctg gcc gaa tat ctc aaa atg cac ggc ggt agt cac aat gcc agc      568
Ser Leu Ala Glu Tyr Leu Lys Met His Gly Gly Ser His Asn Ala Ser
             85                  90                  95 act gcc ccg tat cgc acg gct ttc tat ctg gaa gtt gag aac gac gcc      616
Thr Ala Pro Tyr Arg Thr Ala Phe Tyr Leu Glu Val Glu Asn Asp Ala
    100                 105                 110 ttg cct ggt gcg gta gac cgc ctg gcc gat gct att gct gaa cct ttg      664
Leu Pro Gly Ala Val Asp Arg Leu Ala Asp Ala Ile Ala Glu Pro Leu
115                 120                 125                 130 ctc gac aag aaa tat gcc gaa cgt gag cgt aat gcg gtg aac gct gaa      712
Leu Asp Lys Lys Tyr Ala Glu Arg Glu Arg Asn Ala Val Asn Ala Glu
                    135                 140                 145 tta acc atg gcg cgt acg cgt gac ggg atg cgc atg gca cag gtc agc      760
Leu Thr Met Ala Arg Thr Arg Asp Gly Met Arg Met Ala Gln Val Ser
            150                 155                 160 gca gaa acc att aac ccg gca cac ccc ggt tca aag ttt tct ggt ggt      808
Ala Glu Thr Ile Asn Pro Ala His Pro Gly Ser Lys Phe Ser Gly Gly
        165                 170                 175 aac ctc gaa act tta agc gac aaa cct ggt aat ccg gtg cag cag gcg      856
Asn Leu Glu Thr Leu Ser Asp Lys Pro Gly Asn Pro Val Gln Gln Ala
    180                 185                 190 ctg aaa gat ttc cac gag aag tac tat tcc gcc aat ttg atg aag gcg      904
Leu Lys Asp Phe His Glu Lys Tyr Tyr Ser Ala Asn Leu Met Lys Ala
195                 200                 205                 210 gtt att tac agt aat aaa ccg ctg ccg gag ttg gca aaa atg gcg gcg      952
Val Ile Tyr Ser Asn Lys Pro Leu Pro Glu Leu Ala Lys Met Ala Ala
                    215                 220                 225 gac acc ttt ggt cgc gtg ccg aac aaa gag agc aaa aaa ccg gaa atc     1000
Asp Thr Phe Gly Arg Val Pro Asn Lys Glu Ser Lys Lys Pro Glu Ile
            230                 235                 240 acc gtg ccg gta gtc acc gac gcg caa aag ggc att atc att cat tac     1048
Thr Val Pro Val Val Thr Asp Ala Gln Lys Gly Ile Ile Ile His Tyr
        245                 250                 255 gtc cct gcg ctg ccg cgt aaa gtg ttg cgc gtt gag ttt cgc atc gat     1096
Val Pro Ala Leu Pro Arg Lys Val Leu Arg Val Glu Phe Arg Ile Asp
    260                 265                 270 aac aac tca gcg aag ttc cgt agt aaa acc gat gaa ttg att acc tat     1144
Asn Asn Ser Ala Lys Phe Arg Ser Lys Thr Asp Glu Leu Ile Thr Tyr
275                 280                 285                 290 ctg att ggc aat cgc agc cca ggt aca ctt tct gac tgg ctg caa aag     1192
Leu Ile Gly Asn Arg Ser Pro Gly Thr Leu Ser Asp Trp Leu Gln Lys
                    295                 300                 305 cag gga tta gtt gag ggc att agc gcc aac tcc gat cct atc gtc aac     1240
Gln Gly Leu Val Glu Gly Ile Ser Ala Asn Ser Asp Pro Ile Val Asn
            310                 315                 320 ggc aac agc ggc gta tta gcg atc tct gcg tct tta acc gat aaa ggc     1288
Gly Asn Ser Gly Val Leu Ala Ile Ser Ala Ser Leu Thr Asp Lys Gly
        325                 330                 335 ctg gct aat cgc gat cag gtt gtg gcg gca att ttt agc tat ctc aat     1336
```

```
Leu Ala Asn Arg Asp Gln Val Val Ala Ala Ile Phe Ser Tyr Leu Asn
340                 345                 350 ctg tta cgt gaa aaa ggc att gat aaa caa tac ttc gat gaa ctg gcg      1384
Leu Leu Arg Glu Lys Gly Ile Asp Lys Gln Tyr Phe Asp Glu Leu Ala
355                 360                 365                 370 aat gtg ctg gat atc gac ttc cgt tat ccg tcg atc acc cgt gat atg      1432
Asn Val Leu Asp Ile Asp Phe Arg Tyr Pro Ser Ile Thr Arg Asp Met
            375                 380                 385 gat tac gtc gaa tgg ctg gca gat acc atg att cgc gtt cct gtt gag      1480
Asp Tyr Val Glu Trp Leu Ala Asp Thr Met Ile Arg Val Pro Val Glu
        390                 395                 400 cat acg ctg gat gca gtc aat att gcc gat cgg tac gat gct aaa gca      1528
His Thr Leu Asp Ala Val Asn Ile Ala Asp Arg Tyr Asp Ala Lys Ala
    405                 410                 415 gta aag gaa cgt ctg gcg atg atg acg ccg cag aat gcg cgt atc tgg      1576
Val Lys Glu Arg Leu Ala Met Met Thr Pro Gln Asn Ala Arg Ile Trp
420                 425                 430 tat atc agc ccg aaa gag ccg cac aac aaa acg gct tac ttt gtc gat      1624
Tyr Ile Ser Pro Lys Glu Pro His Asn Lys Thr Ala Tyr Phe Val Asp
435                 440                 445                 450 gcg ccg tat cag gtc gat aaa atc agc gca caa act ttc gcc gac tgg      1672
Ala Pro Tyr Gln Val Asp Lys Ile Ser Ala Gln Thr Phe Ala Asp Trp
            455                 460                 465 cag aaa aaa gcc gcc gac att gcg ctc tct ttg cca gag ctt aac cct      1720
Gln Lys Lys Ala Ala Asp Ile Ala Leu Ser Leu Pro Glu Leu Asn Pro
        470                 475                 480 tat att cct gat gat ttc tcg ctg att aag tca gag aag aaa tac gac      1768
Tyr Ile Pro Asp Asp Phe Ser Leu Ile Lys Ser Glu Lys Lys Tyr Asp
    485                 490                 495 cat cca gag ctg att gtt gat gag tcg aat ctg cgc gtg gtg tat gcg      1816
His Pro Glu Leu Ile Val Asp Glu Ser Asn Leu Arg Val Val Tyr Ala
500                 505                 510 cca agc cgt tat ttt gcc agc gag ccc aaa gct gat gtc agc ctg att      1864
Pro Ser Arg Tyr Phe Ala Ser Glu Pro Lys Ala Asp Val Ser Leu Ile
515                 520                 525                 530 ttg cgt aat ccg aaa gcc atg gac agc gcc cgc aat cag gtg atg ttt      1912
Leu Arg Asn Pro Lys Ala Met Asp Ser Ala Arg Asn Gln Val Met Phe
            535                 540                 545 gcg ctc aat gat tat ctc gca ggg ctg gcg ctt gat cag tta agc aac      1960
Ala Leu Asn Asp Tyr Leu Ala Gly Leu Ala Leu Asp Gln Leu Ser Asn
        550                 555                 560 cag gcg tcg gtt ggt ggc ata agt ttt tcc acc aac gct aac aac ggc      2008
Gln Ala Ser Val Gly Gly Ile Ser Phe Ser Thr Asn Ala Asn Asn Gly
    565                 570                 575 ctt atg gtt aat gct aat ggt tac acc cag cgt ctg ccg cag ctg ttc      2056
Leu Met Val Asn Ala Asn Gly Tyr Thr Gln Arg Leu Pro Gln Leu Phe
580                 585                 590 cag gca ttg ctc gag ggg tac ttt agc tat acc gct acg gaa gat cag      2104
Gln Ala Leu Leu Glu Gly Tyr Phe Ser Tyr Thr Ala Thr Glu Asp Gln
595                 600                 605                 610 ctt gag cag gcg aag tcc tgg tat aac cag atg atg gat tcc gca gaa      2152
Leu Glu Gln Ala Lys Ser Trp Tyr Asn Gln Met Met Asp Ser Ala Glu
            615                 620                 625 aag ggt aaa gcg ttt gag cag gcg att atg ccc gcg cag atg ctc tcg      2200
Lys Gly Lys Ala Phe Glu Gln Ala Ile Met Pro Ala Gln Met Leu Ser
        630                 635                 640 caa gtg ccg tac ttc tcg cga gat gaa cgg cgt aaa att ttg ccc tcg      2248
Gln Val Pro Tyr Phe Ser Arg Asp Glu Arg Arg Lys Ile Leu Pro Ser
    645                 650                 655
```

| | | |
|---|---|---|
| att acg ttg aaa gag gtg ctg gcc tat cgc gac gcc tta aaa tca ggg<br>Ile Thr Leu Lys Glu Val Leu Ala Tyr Arg Asp Ala Leu Lys Ser Gly<br>660                665                  670 | | 2296 |
| gct cga cca gag ttt atg gtt atc ggc aac atg acc gag gcc cag gca<br>Ala Arg Pro Glu Phe Met Val Ile Gly Asn Met Thr Glu Ala Gln Ala<br>675               680            685            690 | | 2344 |
| aca acg ctg gca cgc gat gtg caa aaa cag ttg ggc gct gat ggt tca<br>Thr Thr Leu Ala Arg Asp Val Gln Lys Gln Leu Gly Ala Asp Gly Ser<br>                695                 700                705 | | 2392 |
| gag tgg tgt cga aac aaa gat gta gtg gtc gat aaa aaa caa tcc gtc<br>Glu Trp Cys Arg Asn Lys Asp Val Val Val Asp Lys Lys Gln Ser Val<br>710                715                 720 | | 2440 |
| atc ttt gaa aaa gcc ggt aac agc acc gac tcc gca ctg gca gcg gta<br>Ile Phe Glu Lys Ala Gly Asn Ser Thr Asp Ser Ala Leu Ala Ala Val<br>725                730                 735 | | 2488 |
| ttt gta ccg act ggc tac gat gaa tac acc agc tca gcc tat agc tct<br>Phe Val Pro Thr Gly Tyr Asp Glu Tyr Thr Ser Ser Ala Tyr Ser Ser<br>740                745                 750 | | 2536 |
| ctg ttg ggg cag atc gta cag ccg tgg ttc tac aat cag ttg cgt acc<br>Leu Leu Gly Gln Ile Val Gln Pro Trp Phe Tyr Asn Gln Leu Arg Thr<br>755               760            765            770 | | 2584 |
| gaa gaa caa ttg ggc tat gcc gtg ttt gcg ttt cca atg agc gtg ggg<br>Glu Glu Gln Leu Gly Tyr Ala Val Phe Ala Phe Pro Met Ser Val Gly<br>                775                 780                785 | | 2632 |
| cgt cag tgg ggc atg ggc ttc ctt ttg caa agc aat gat aaa cag cct<br>Arg Gln Trp Gly Met Gly Phe Leu Leu Gln Ser Asn Asp Lys Gln Pro<br>790                795                 800 | | 2680 |
| tca ttc ttg tgg gag cgt tac aag gcg ttt ttc cca acc gca gag gca<br>Ser Phe Leu Trp Glu Arg Tyr Lys Ala Phe Phe Pro Thr Ala Glu Ala<br>805                810                 815 | | 2728 |
| aaa ttg cga gcg atg aag cca gat gag ttt gcg caa atc cag cag gcg<br>Lys Leu Arg Ala Met Lys Pro Asp Glu Phe Ala Gln Ile Gln Gln Ala<br>820                825                 830 | | 2776 |
| gta att acc cag atg ctg cag gca ccg caa acg ctc ggc gaa gaa gca<br>Val Ile Thr Gln Met Leu Gln Ala Pro Gln Thr Leu Gly Glu Glu Ala<br>835                840                 845            850 | | 2824 |
| tcg aag tta agt aaa gat ttc gat cgc ggc aat atg cgc ttc gat tcg<br>Ser Lys Leu Ser Lys Asp Phe Asp Arg Gly Asn Met Arg Phe Asp Ser<br>                855                 860                865 | | 2872 |
| cgt gat aaa atc gtg gcc cag ata aaa ctg ctg acg ccg caa aaa ctt<br>Arg Asp Lys Ile Val Ala Gln Ile Lys Leu Leu Thr Pro Gln Lys Leu<br>870                875                 880 | | 2920 |
| gct gat ttc ttc cat cag gcg gtg gtc gag ccg caa ggc atg gct att<br>Ala Asp Phe Phe His Gln Ala Val Val Glu Pro Gln Gly Met Ala Ile<br>885                890                 895 | | 2968 |
| ctg tcg cag att tcc ggc agc cag aac ggg aaa gcc gaa tat gta cac<br>Leu Ser Gln Ile Ser Gly Ser Gln Asn Gly Lys Ala Glu Tyr Val His<br>900                905                 910 | | 3016 |
| cct gaa ggc tgg aaa gtg tgg gag aac gtc agc gcg ttg cag caa aca<br>Pro Glu Gly Trp Lys Val Trp Glu Asn Val Ser Ala Leu Gln Gln Thr<br>915                920                 925            930 | | 3064 |
| atg ccc ctg atg agt gaa aag aat gag tgatgtcgcc gagacactag<br>Met Pro Leu Met Ser Glu Lys Asn Glu<br>                935 | | 3111 |
| atcctttgc | | 3120 |

<210> SEQ ID NO 50
<211> LENGTH: 962
<212> TYPE: PRT
<213> ORGANISM: Escherichia coli

<400> SEQUENCE: 50

```
Met Pro Arg Ser Thr Trp Phe Lys Ala Leu Leu Leu Val Ala Leu
            -20                 -15                 -10

Trp Ala Pro Leu Ser Gln Ala Glu Thr Gly Trp Gln Pro Ile Gln Glu
 -5              -1   1                   5

Thr Ile Arg Lys Ser Asp Lys Asp Asn Arg Gln Tyr Gln Ala Ile Arg
 10                  15                  20                  25

Leu Asp Asn Gly Met Val Val Leu Val Ser Asp Pro Gln Ala Val
                 30                  35                  40

Lys Ser Leu Ser Ala Leu Val Val Pro Val Gly Ser Leu Glu Asp Pro
                 45                  50                  55

Glu Ala Tyr Gln Gly Leu Ala His Tyr Leu Glu His Met Ser Leu Met
                 60                  65                  70

Gly Ser Lys Lys Tyr Pro Gln Ala Asp Ser Leu Ala Glu Tyr Leu Lys
                 75                  80                  85

Met His Gly Gly Ser His Asn Ala Ser Thr Ala Pro Tyr Arg Thr Ala
 90                  95                 100                 105

Phe Tyr Leu Glu Val Glu Asn Asp Ala Leu Pro Gly Ala Val Asp Arg
                110                 115                 120

Leu Ala Asp Ala Ile Ala Glu Pro Leu Leu Asp Lys Lys Tyr Ala Glu
                125                 130                 135

Arg Glu Arg Asn Ala Val Asn Ala Glu Leu Thr Met Ala Arg Thr Arg
                140                 145                 150

Asp Gly Met Arg Met Ala Gln Val Ser Ala Glu Thr Ile Asn Pro Ala
                155                 160                 165

His Pro Gly Ser Lys Phe Ser Gly Gly Asn Leu Glu Thr Leu Ser Asp
170                 175                 180                 185

Lys Pro Gly Asn Pro Val Gln Gln Ala Leu Lys Asp Phe His Glu Lys
                190                 195                 200

Tyr Tyr Ser Ala Asn Leu Met Lys Ala Val Ile Tyr Ser Asn Lys Pro
                205                 210                 215

Leu Pro Glu Leu Ala Lys Met Ala Ala Asp Thr Phe Gly Arg Val Pro
                220                 225                 230

Asn Lys Glu Ser Lys Lys Pro Glu Ile Thr Val Pro Val Val Thr Asp
                235                 240                 245

Ala Gln Lys Gly Ile Ile His Tyr Val Pro Ala Leu Pro Arg Lys
250                 255                 260                 265

Val Leu Arg Val Glu Phe Arg Ile Asp Asn Asn Ser Ala Lys Phe Arg
                270                 275                 280

Ser Lys Thr Asp Glu Leu Ile Thr Tyr Leu Ile Gly Asn Arg Ser Pro
                285                 290                 295

Gly Thr Leu Ser Asp Trp Leu Gln Lys Gln Gly Leu Val Glu Gly Ile
                300                 305                 310

Ser Ala Asn Ser Asp Pro Ile Val Asn Gly Asn Ser Gly Val Leu Ala
                315                 320                 325

Ile Ser Ala Ser Leu Thr Asp Lys Gly Leu Ala Asn Arg Asp Gln Val
330                 335                 340                 345

Val Ala Ala Ile Phe Ser Tyr Leu Asn Leu Arg Glu Lys Gly Ile
                350                 355                 360

Asp Lys Gln Tyr Phe Asp Glu Leu Ala Asn Val Leu Asp Ile Asp Phe
                365                 370                 375

Arg Tyr Pro Ser Ile Thr Arg Asp Met Asp Tyr Val Glu Trp Leu Ala
```

-continued

```
            380                 385                 390
Asp Thr Met Ile Arg Val Pro Val Glu His Thr Leu Asp Ala Val Asn
395                 400                 405
Ile Ala Asp Arg Tyr Asp Ala Lys Ala Val Lys Glu Arg Leu Ala Met
410                 415                 420                 425
Met Thr Pro Gln Asn Ala Arg Ile Trp Tyr Ile Ser Pro Lys Glu Pro
                430                 435                 440
His Asn Lys Thr Ala Tyr Phe Val Asp Ala Pro Tyr Gln Val Asp Lys
                445                 450                 455
Ile Ser Ala Gln Thr Phe Ala Asp Trp Gln Lys Lys Ala Ala Asp Ile
                460                 465                 470
Ala Leu Ser Leu Pro Glu Leu Asn Pro Tyr Ile Pro Asp Asp Phe Ser
475                 480                 485
Leu Ile Lys Ser Glu Lys Lys Tyr Asp His Pro Glu Leu Ile Val Asp
490                 495                 500                 505
Glu Ser Asn Leu Arg Val Val Tyr Ala Pro Ser Arg Tyr Phe Ala Ser
                510                 515                 520
Glu Pro Lys Ala Asp Val Ser Leu Ile Leu Arg Asn Pro Lys Ala Met
                525                 530                 535
Asp Ser Ala Arg Asn Gln Val Met Phe Ala Leu Asn Asp Tyr Leu Ala
                540                 545                 550
Gly Leu Ala Leu Asp Gln Leu Ser Asn Gln Ala Ser Val Gly Gly Ile
                555                 560                 565
Ser Phe Ser Thr Asn Ala Asn Asn Gly Leu Met Val Asn Ala Asn Gly
570                 575                 580                 585
Tyr Thr Gln Arg Leu Pro Gln Leu Phe Gln Ala Leu Leu Glu Gly Tyr
                590                 595                 600
Phe Ser Tyr Thr Ala Thr Glu Asp Gln Leu Glu Gln Ala Lys Ser Trp
                605                 610                 615
Tyr Asn Gln Met Met Asp Ser Ala Glu Lys Gly Lys Ala Phe Glu Gln
                620                 625                 630
Ala Ile Met Pro Ala Gln Met Leu Ser Gln Val Pro Tyr Phe Ser Arg
                635                 640                 645
Asp Glu Arg Arg Lys Ile Leu Pro Ser Ile Thr Leu Lys Glu Val Leu
650                 655                 660                 665
Ala Tyr Arg Asp Ala Leu Lys Ser Gly Ala Arg Pro Glu Phe Met Val
                670                 675                 680
Ile Gly Asn Met Thr Glu Ala Gln Ala Thr Thr Leu Ala Arg Asp Val
                685                 690                 695
Gln Lys Gln Leu Gly Ala Asp Gly Ser Glu Trp Cys Arg Asn Lys Asp
                700                 705                 710
Val Val Val Asp Lys Lys Gln Ser Val Ile Phe Glu Lys Ala Gly Asn
                715                 720                 725
Ser Thr Asp Ser Ala Leu Ala Ala Val Phe Val Pro Thr Gly Tyr Asp
730                 735                 740                 745
Glu Tyr Thr Ser Ser Ala Tyr Ser Ser Leu Leu Gly Gln Ile Val Gln
                750                 755                 760
Pro Trp Phe Tyr Asn Gln Leu Arg Thr Glu Gln Leu Gly Tyr Ala
                765                 770                 775
Val Phe Ala Phe Pro Met Ser Val Gly Arg Gln Trp Gly Met Gly Phe
                780                 785                 790
Leu Leu Gln Ser Asn Asp Lys Gln Pro Ser Phe Leu Trp Glu Arg Tyr
795                 800                 805
```

```
Lys Ala Phe Phe Pro Thr Ala Glu Ala Lys Leu Arg Ala Met Lys Pro
810                 815                 820                 825

Asp Glu Phe Ala Gln Ile Gln Gln Ala Val Ile Thr Gln Met Leu Gln
            830                 835                 840

Ala Pro Gln Thr Leu Gly Glu Gly Ala Ser Lys Leu Ser Lys Asp Phe
                845                 850                 855

Asp Arg Gly Asn Met Arg Phe Asp Ser Arg Asp Lys Ile Val Ala Gln
            860                 865                 870

Ile Lys Leu Leu Thr Pro Gln Lys Leu Ala Asp Phe Phe His Gln Ala
        875                 880                 885

Val Val Glu Pro Gln Gly Met Ala Ile Leu Ser Gln Ile Ser Gly Ser
890                 895                 900                 905

Gln Asn Gly Lys Ala Glu Tyr Val His Pro Glu Gly Trp Lys Val Trp
                910                 915                 920

Glu Asn Val Ser Ala Leu Gln Gln Thr Met Pro Leu Met Ser Glu Lys
            925                 930                 935

Asn Glu

<210> SEQ ID NO 51
<211> LENGTH: 729
<212> TYPE: DNA
<213> ORGANISM: Artificial Sequence
<220> FEATURE:
<223> OTHER INFORMATION: wild-type DsbC comprising his-tag
<220> FEATURE:
<221> NAME/KEY: CDS
<222> LOCATION: (1)..(729)

<400> SEQUENCE: 51 atg aag aaa ggt ttt atg ttg ttt act ttg tta gcg gcg ttt tca ggc     48
Met Lys Lys Gly Phe Met Leu Phe Thr Leu Leu Ala Ala Phe Ser Gly
1               5                   10                  15 ttt gct cag gct gat gac gcg gca att caa caa acg tta gcc aaa atg     96
Phe Ala Gln Ala Asp Asp Ala Ala Ile Gln Gln Thr Leu Ala Lys Met
            20                  25                  30 ggc atc aaa agc agc gat att cag ccc gcg cct gta gct ggc atg aag    144
Gly Ile Lys Ser Ser Asp Ile Gln Pro Ala Pro Val Ala Gly Met Lys
        35                  40                  45 aca gtt ctg act aac agc ggc gtg ttg tac atc acc gat gat ggt aaa    192
Thr Val Leu Thr Asn Ser Gly Val Leu Tyr Ile Thr Asp Asp Gly Lys
    50                  55                  60 cat atc att cag ggg cca atg tat gac gtt agt ggc acg gct ccg gtc    240
His Ile Ile Gln Gly Pro Met Tyr Asp Val Ser Gly Thr Ala Pro Val
65                  70                  75                  80 aat gtc acc aat aag atg ctg tta aag cag ttg aat gcg ctt gaa aaa    288
Asn Val Thr Asn Lys Met Leu Leu Lys Gln Leu Asn Ala Leu Glu Lys
                85                  90                  95 gag atg atc gtt tat aaa gcg ccg cag gaa aaa cac gtc atc acc gtg    336
Glu Met Ile Val Tyr Lys Ala Pro Gln Glu Lys His Val Ile Thr Val
            100                 105                 110 ttt act gat att acc tgt ggt tac tgc cac aaa ctg cat gag caa atg    384
Phe Thr Asp Ile Thr Cys Gly Tyr Cys His Lys Leu His Glu Gln Met
        115                 120                 125 gca gac tac aac gcg ctg ggg atc acc gtg cgt tat ctt gct ttc ccg    432
Ala Asp Tyr Asn Ala Leu Gly Ile Thr Val Arg Tyr Leu Ala Phe Pro
    130                 135                 140 cgc cag ggg ctg gac agc gat gca gag aaa gaa atg aaa gct atc tgg    480
Arg Gln Gly Leu Asp Ser Asp Ala Glu Lys Glu Met Lys Ala Ile Trp
145                 150                 155                 160
```

```
tgt gcg aaa gat aaa aac aaa gcg ttt gat gat gtg atg gca ggt aaa      528
Cys Ala Lys Asp Lys Asn Lys Ala Phe Asp Asp Val Met Ala Gly Lys
            165                 170                 175 agc gtc gca cca gcc agt tgc gac gtg gat att gcc gac cat tac gca      576
Ser Val Ala Pro Ala Ser Cys Asp Val Asp Ile Ala Asp His Tyr Ala
        180                 185                 190 ctt ggc gtc cag ctt ggc gtt agc ggt act ccg gca gtt gtg ctg agc      624
Leu Gly Val Gln Leu Gly Val Ser Gly Thr Pro Ala Val Val Leu Ser
    195                 200                 205 aat ggc aca ctt gtt ccg ggt tac cag ccg ccg aaa gag atg aaa gaa      672
Asn Gly Thr Leu Val Pro Gly Tyr Gln Pro Pro Lys Glu Met Lys Glu
210                 215                 220 ttc ctc gac gaa cac caa aaa atg acc agc ggt aaa cac cat cac cat      720
Phe Leu Asp Glu His Gln Lys Met Thr Ser Gly Lys His His His His
225                 230                 235                 240 cac cac taa                                                          729
His His
```

<210> SEQ ID NO 52
<211> LENGTH: 242
<212> TYPE: PRT
<213> ORGANISM: Artificial Sequence
<220> FEATURE:
<223> OTHER INFORMATION: Synthetic Construct

<400> SEQUENCE: 52

```
Met Lys Lys Gly Phe Met Leu Phe Thr Leu Leu Ala Ala Phe Ser Gly
1               5                   10                  15

Phe Ala Gln Ala Asp Asp Ala Ala Ile Gln Gln Thr Leu Ala Lys Met
                20                  25                  30

Gly Ile Lys Ser Ser Asp Ile Gln Pro Ala Pro Val Ala Gly Met Lys
            35                  40                  45

Thr Val Leu Thr Asn Ser Gly Val Leu Tyr Ile Thr Asp Asp Gly Lys
        50                  55                  60

His Ile Ile Gln Gly Pro Met Tyr Asp Val Ser Gly Thr Ala Pro Val
65                  70                  75                  80

Asn Val Thr Asn Lys Met Leu Leu Lys Gln Leu Asn Ala Leu Glu Lys
                85                  90                  95

Glu Met Ile Val Tyr Lys Ala Pro Gln Glu Lys His Val Ile Thr Val
            100                 105                 110

Phe Thr Asp Ile Thr Cys Gly Tyr Cys His Lys Leu His Glu Gln Met
        115                 120                 125

Ala Asp Tyr Asn Ala Leu Gly Ile Thr Val Arg Tyr Leu Ala Phe Pro
    130                 135                 140

Arg Gln Gly Leu Asp Ser Asp Ala Glu Lys Glu Met Lys Ala Ile Trp
145                 150                 155                 160

Cys Ala Lys Asp Lys Asn Lys Ala Phe Asp Asp Val Met Ala Gly Lys
                165                 170                 175

Ser Val Ala Pro Ala Ser Cys Asp Val Asp Ile Ala Asp His Tyr Ala
            180                 185                 190

Leu Gly Val Gln Leu Gly Val Ser Gly Thr Pro Ala Val Val Leu Ser
        195                 200                 205

Asn Gly Thr Leu Val Pro Gly Tyr Gln Pro Pro Lys Glu Met Lys Glu
    210                 215                 220

Phe Leu Asp Glu His Gln Lys Met Thr Ser Gly Lys His His His His
225                 230                 235                 240
```

-continued

His His

<210> SEQ ID NO 53
<211> LENGTH: 66
<212> TYPE: DNA
<213> ORGANISM: Escherichia coli
<220> FEATURE:
<221> NAME/KEY: exon
<222> LOCATION: (4)..(66)

<400> SEQUENCE: 53

```
tga atg ccc cgc agc acc tgg ttc aaa gca tta ttg ttg tta gtt gcc    48
    Met Pro Arg Ser Thr Trp Phe Lys Ala Leu Leu Leu Leu Val Ala
    1               5                   10                  15 ctt tgg gca ccc tta agt                                              66
Leu Trp Ala Pro Leu Ser
            20
```

<210> SEQ ID NO 54
<211> LENGTH: 66
<212> TYPE: DNA
<213> ORGANISM: Escherichia coli
<220> FEATURE:
<221> NAME/KEY: exon
<222> LOCATION: (4)..(60)
<220> FEATURE:
<221> NAME/KEY: exon
<222> LOCATION: (64)..(66)

<400> SEQUENCE: 54

```
tga att ccc cgc agc acc tgg ttc aaa gca tta ttg ttg tta gtt gcc    48
    Ile Pro Arg Ser Thr Trp Phe Lys Ala Leu Leu Leu Leu Val Ala
    1               5                   10                  15 ctt tgg gca cat taa tgt                                              66
Leu Trp Ala His     Cys
            20
```

<210> SEQ ID NO 55
<211> LENGTH: 66
<212> TYPE: DNA
<213> ORGANISM: Escherichia coli
<220> FEATURE:
<221> NAME/KEY: exon
<222> LOCATION: (1)..(66)

<400> SEQUENCE: 55

```
atg aac atg ttt ttt agg ctt acc gcg tta gct ggc ctg ctt gca ata    48
Met Asn Met Phe Phe Arg Leu Thr Ala Leu Ala Gly Leu Leu Ala Ile
1               5                   10                  15 gca ggc cag acc ttc gct                                              66
Ala Gly Gln Thr Phe Ala
            20
```

<210> SEQ ID NO 56
<211> LENGTH: 66
<212> TYPE: DNA
<213> ORGANISM: Escherichia coli
<220> FEATURE:
<221> NAME/KEY: exon
<222> LOCATION: (1)..(27)
<220> FEATURE:
<221> NAME/KEY: exon
<222> LOCATION: (31)..(45)
<220> FEATURE:
<221> NAME/KEY: exon
<222> LOCATION: (49)..(60)
<220> FEATURE:
<221> NAME/KEY: exon
<222> LOCATION: (64)..(66)

```
<400> SEQUENCE: 56 atg aat tcg ttt tta ggc tta ccg cgt tag ctg gcc tgc ttg caa tag        48
Met Asn Ser Phe Leu Gly Leu Pro Arg     Leu Ala Cys Leu Gln
1               5                       10 cag gcc aga cat taa ttg                                                66
Gln Ala Arg His     Leu
            15

<210> SEQ ID NO 57
<211> LENGTH: 33
<212> TYPE: DNA
<213> ORGANISM: Escherichia coli
<220> FEATURE:
<221> NAME/KEY: exon
<222> LOCATION: (1)..(33)

<400> SEQUENCE: 57 gat gca gcg atc aac cgt ggt aac tcc ggt ggt                            33
Asp Ala Ala Ile Asn Arg Gly Asn Ser Gly Gly
1               5                   10

<210> SEQ ID NO 58
<211> LENGTH: 33
<212> TYPE: DNA
<213> ORGANISM: Escherichia coli
<220> FEATURE:
<221> NAME/KEY: exon
<222> LOCATION: (1)..(33)

<400> SEQUENCE: 58 gat gca gcg att aat cgt ggt aac gcc ggt ggt                            33
Asp Ala Ala Ile Asn Arg Gly Asn Ala Gly Gly
1               5                   10
```